US007399584B2

(12) United States Patent
Cronin et al.

(10) Patent No.: US 7,399,584 B2
(45) Date of Patent: Jul. 15, 2008

(54) METHOD OF COMPARING A TARGET NUCLEIC ACID AND A REFERENCE NUCLEIC ACID

(75) Inventors: Maureen T. Cronin, Los Altos, CA (US); Charles Garrett Miyada, San Jose, CA (US); Earl A. Hubbell, Mountain View, CA (US); Mark Chee, Palo Alto, CA (US); Stephen P. A. Fodor, Palo Alto, CA (US); Xiaohua C. Huang, Mountain View, CA (US); Robert J. Lipshutz, Palo Alto, CA (US); Peter E. Lobban, Palo Alto, CA (US); MacDonald S. Morris, Felton, CA (US); Edward L. Sheldon, San Diego, CA (US)

(73) Assignee: Affymetrix, Inc., Santa Clara, CA (US)

( * ) Notice: Subject to any disclaimer, the term of this patent is extended or adjusted under 35 U.S.C. 154(b) by 368 days.

(21) Appl. No.: 09/510,378

(22) Filed: Feb. 22, 2000

(65) Prior Publication Data

US 2003/0165823 A1    Sep. 4, 2003

Related U.S. Application Data

(63) Continuation of application No. 08/544,381, filed on Oct. 10, 1995, now Pat. No. 6,027,880, which is a continuation-in-part of application No. 08/510,521, filed on Aug. 2, 1995, now Pat. No. 7,115,364, which is a continuation-in-part of application No. PCT/US94/12305, filed on Oct. 26, 1994, which is a continuation-in-part of application No. 08/284,064, filed on Aug. 2, 1994, now abandoned, which is a continuation-in-part of application No. 08/143,312, filed on Oct. 26, 1993, now abandoned.

(51) Int. Cl.
    C12Q 1/68       (2006.01)
    C12P 19/34      (2006.01)
    C12M 1/34       (2006.01)
    C07H 21/00      (2006.01)

(52) U.S. Cl. .................. 435/6; 435/91.1; 435/287.2; 536/23.1; 536/24.3

(58) Field of Classification Search ............... 436/518, 436/501; 435/71, 6, DIG. 1, DIG. 2, DIG. 14, 435/DIG. 15, DIG. 17, DIG. 22, DIG. 34, 435/DIG. 37, DIG. 40, 69.1, 810, 91.2, 518; 422/50, 681; 536/25.3, 23.1, 24.1, 24.3; 935/77, 78

See application file for complete search history.

(56) References Cited

U.S. PATENT DOCUMENTS

| 4,656,127 | A | * | 4/1987 | Mundy ........................ 435/6 |
| 4,683,195 | A |   | 7/1987 | Mullis et al. .................. 435/6 |
| 5,002,867 | A |   | 3/1991 | Macevicz .................... 435/6 |
| 5,057,410 | A | * | 10/1991 | Kawasaki et al. ............. 435/6 |
| 5,143,854 | A |   | 9/1992 | Pirrung et al. ............. 435/518 |
| 5,202,231 | A |   | 4/1993 | Drmanac et al. ............... 435/6 |
| 5,273,632 | A |   | 12/1993 | Stockham et al. ........ 204/108.1 |
| 5,445,934 | A | * | 8/1995 | Fodor et al. ................... 435/6 |
| 5,527,681 | A |   | 6/1996 | Holmes ........................ 435/6 |
| 5,660,979 | A | * | 8/1997 | Romano et al. ............... 435/5 |
| 5,681,942 | A | * | 10/1997 | Buchwald et al. .......... 536/23.5 |
| 5,700,637 | A | * | 12/1997 | Southern ....................... 435/6 |
| 5,837,832 | A | * | 11/1998 | Chee et al. .................... 435/6 |
| 6,027,880 | A | * | 2/2000 | Cronin et al. ................. 435/6 |
| 6,309,823 | B1 | * | 10/2001 | Cronin et al. ................. 435/6 |

FOREIGN PATENT DOCUMENTS

| WO | WO89/10977 | 11/1989 |
| WO | WO89/11548 | 11/1989 |
| WO | WO90/00626 | 1/1990 |
| WO | WO90/03382 | 4/1990 |
| WO | WO92/10092 | 6/1992 |
| WO | WO92/10588 | 6/1992 |
| WO | WO93/17126 | 9/1993 |
| WO | WO95/00530 | 1/1995 |
| WO | WO95/11995 | 5/1995 |
| WO | WO95/26973 | 10/1995 |

OTHER PUBLICATIONS

Chee et al., "Towards sequencing mitochronidrial DNA polymorphisms by hybridization to a custom oligonucleotide probe array", *American Society of Human Genetics, 43$^{rd}$ Annual Meeting*, Oct. 5-9, 1993; abstract.

Chee et al., "Genetic analysis by hybridization to sequence-specific DNA arrays", *American Society of Human Genetics, 43$^{rd}$ Annual Meeting*, Oct. 5-9, 1993; abstract.

Chee et al., "A new method for rapid sequence analysis: detection of HIV reverse transcriptase mutations", *HIV Drug Resistance Third International Workshop*, Aug. 2-5, ???; abstract.

Chee et al., "Sequence analysis by hybridization: the human mitochondrial genome on a chip", *Genome Sequencing and Analysis Conference V*, Sep. 17-21, 1994; abstract.

Chee et al., "Sequencing mitochondrial DNA polymorphisms by hybridization", *American Society of Human Genetics, 44$^{th}$ Annual Meeting*, Oct. 18-22, 1994; abstract.

Chee, "Resequencing DNA by hybridization to oligonucleotide arrays", *Western Biotech Conference*, Oct. 18-21, 1995; abstract.

Cronin et al., "Hybridization to arrays of oligonucleotides", *Nucleic Acids in Medical Applications Conference sponsored by AACC*, Jan. 1993; abstract.

(Continued)

*Primary Examiner*—Marjorie A. Moran
*Assistant Examiner*—Marina Miller

(57) ABSTRACT

The invention provides methods of comparing a target nucleic acid with a reference nucleic acid using nucleic acid arrays.

13 Claims, 30 Drawing Sheets

OTHER PUBLICATIONS

Cronin et al., "Detection of cystic fibrosis gene mutations by hybridization to GeneChip™ probe arrays", *Nucleic Acids in Medical Applications Conference, sponsored by AACC*, Nov. 1993; abstract.

Cronin et al., "GeneChip™ screening assay for cystic fibrosis mutations", *American Society of Human Genetics Meeting*, Oct. 1994; abstract.

Cronin et al., Detecting cystic fibrosis mutations by hybridization to DNA probe arrays *UCSF School of Medicine Symposium: Molecular Approaches to Laboratory Diagnosis*, Feb. 1995; abstract.

Elder, "Analysis of DNA oligonucleotide hybridization data by maximum entropy", *Maximum Entropy and Bayesian Methods*, 1992, pp. 1-10.

Hagstrom et al., "Maximum likelihood genetic sequence reconstruction from oligo content", *Argonne Nat'l Laboratory Preprint MCS-P309-0592*, Sep. 1992.

Lipschutz, "Likelihood DNA sequencing by hybridization", *Jrnl. Of Biomolecular Structure & Dynamics*, vol. 11, 1993, pp. 637-653.

Lipschutz, "Oligonucleotide arrays for hybridization analysis", *Genome Sequencing and Analysis Conference V*, Oct. 23-27, 1993; abstract.

Lobban et al., "DNA chips for genetic analysis", *Genome Sequencing and Analysis Conference V*, Oct. 23-27, 1993; abstract.

Lockhart et al., "DNA sequencing by hybridization on high-density probe arrays: enzymatic enhancement and sequence reconstruction", *American Society of Human Genetics, 44th Annual Meeting*, Oct. 18-2, 1994; abstract.

Luo et al., "Cellular protein modulates effects of human immunodeficiency virus type 1 rev" *J. Virol.*, vol. 68, 1994, pp. 3850-3856.

Maxam et al., "A new method for sequencing DNA", *Proc. Natl. Acad. Sci. USA*, vol. 74, 1977, pp. 560-564.

Maxam et al., "Sequencing end-labeled DNA with base-specific chemical cleavages", *Methods in Enzymology*, vol. 65, 1980, pp. 449-560.

Miyada et al., "Detection of cystic fibrosis mutations in a GeneChip™ assay format", *Amer. Society of Human. Genetics, 44th Annual Meeting*, Oct. 1994; abstract.

Querat et al., "Nucleotide sequence analysis of SA-OMVV, a Visna-related ovine lentivirus: phylogenetic history of lentiviruses", *Virology*, vol. 175, 1990, pp. 434-447.

Ratner et al., "Complete nucleotide sequence of the AIDS virus, HTLV-III", *Nature*, vol. 313, 1985, pp. 277-284.

Sambrook et al., "Molecular cloning", 1989, pp. 1145-1147.

Sanger et al., "DNA sequencing with chain-terminating inhibitors", *Proc. Natl. Acad. Sci. USA*, vol. 74, 1977, pp. 5463-5467.

Southern et al., "Analyzing and comparing nucleic acid sequences by hybridization to arrays of oligonucleotide: evaluation using experimental models", *Genomics 13*, 1942, pp. 1008-1017.

Stratagene 1988 Catalog, "Gene Characterization Kits", p. 39.

Wain-Hobson et al., "Nucleotide sequence of the AIDS virus, LAV", *Cell*, vol. 40, 1985, pp. 9-17.

\* cited by examiner $n_1 n_2 n_3 n_4 n_5$
A C T G T T A G C T A A T T G G — REF. SEQ.

| | | | | | |
|---|---|---|---|---|---|
| A-LANE | TGAC | GAAA | AGAA | CAAT | AAAG |
| C-LANE | TGCC | GACA | ACCA | CACT | AACG |
| G-LANE | TGGC | GAGA | ACGA | CAGT | AAGG |
| T-LANE | TGTC | GATA | ACTA | CATT | AATG |
| | $I_1$ | $I_2$ | $I_3$ | $I_4$ | $I_5$ |
| WT. LANE | TGAC | GACA | ACAA | CAAT | AATG |

FIG. 4A $m_1\ m_2$
A C T G T T A G C T A A T T G G
  5'T C G A T T A 3'
         I                         CENTRAL INTERROGATION POSITION

5'A A T C G A T 3'
              I                    3' INTERROGATION POSITION

5'T T A A C C 3'
            I                      5' INTERROGATION POSITION

```
                              n CORRESPONDING NUCLEOTIDE
                  A C T G T T A G C T A A T T G G ── REF. SEQ.
                        C A A T C G A ── PROBE FROM FIRST SET
    INTERROGATION       C A A ─ C G A T ── DELETION PROBE
    POSITION            C A A A T C G A  ⎫
                        C A A C T C G A  ⎪ INSERTION
                        C A A G T C G A  ⎬ PROBES
                        C A A T T C G A  ⎭
                          │      └── INTERROGATION
                       INSERTED    POSITION
                       NUCLEOTIDE
```

*FIG. 6*

```
                    n₁  n₂  n₃ ─── CORRESPONDING NUCLEOTIDES
         A C T G T T A G C T A A T T G G ─── REF. SEQ.
                 C A A T C G A ─── PROBE FROM FIRST SET
                 I₁  I₂  I₃ ─── INTERROGATION POSITIONS

C C A T C G A  ⎫  CORRESPONDING PROBES
         C G A T C G A  ⎬  FROM SECOND, THIRD AND
         C T A T C G A  ⎭  FOURTH PROBE SETS
         I₁

C A A A C G A  ⎫  CORRESPONDING PROBES
         C A A C C G A  ⎬  FROM FIFTH, SIXTH AND
         C A A G C G A  ⎭  SEVENTH PROBE SETS
             I₂

C A A T C A A  ⎫  CORRESPONDING PROBES
         C A A T C C A  ⎬  FROM EIGHTH, NINTH AND
         C A A T C T A  ⎭  TENTH PROBE SETS
                 I₃
```

*FIG. 7*

```
         n3  n4 n1    n2
     A C T G T T A G C T A A T T G G ← REF. SEQ.
           C A A T C A A T
           C A C T C C A T
           C A G T C G A T
           C A T T C T A T
             I1    I2  ← INTERROGATION POSITIONS

T G A C T A T
         T G C C G A T
         T G G C C A T
         T G T C A A T
           I3   I4  ← INTERROGATION POSITIONS
```

FIG. 8

```
              n CORRESPONDING NUCLEOTIDE
     A T T C C C G G G A T C
         A G G G C C A T ← PROBE FROM FIRST PROBE SET
         A G G C C C A T ⎫
         A G G A C C A T ⎬ CORRESPONDING PROBES FROM SECOND, THIRD AND
         A G G T C C A T ⎭ FOURTH PROBE SETS
                 I
                   ← HELPER MUTATION
                  INTERROGATION POSITION
```

FIG. 9

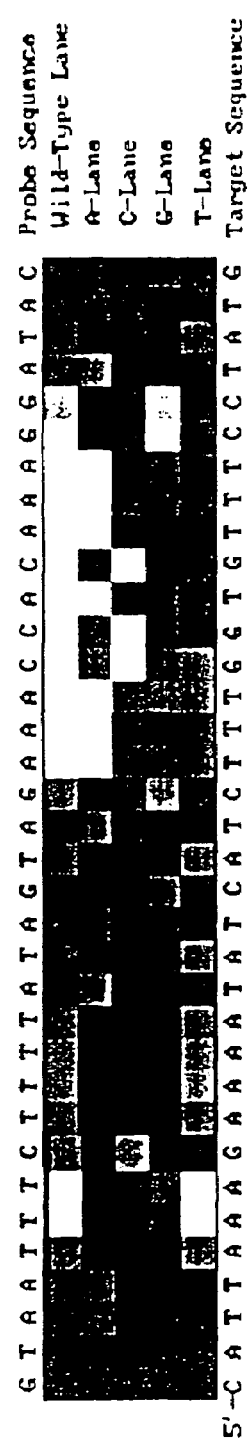
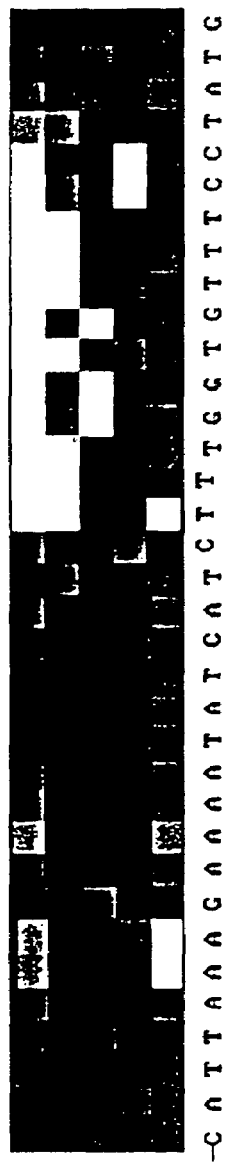
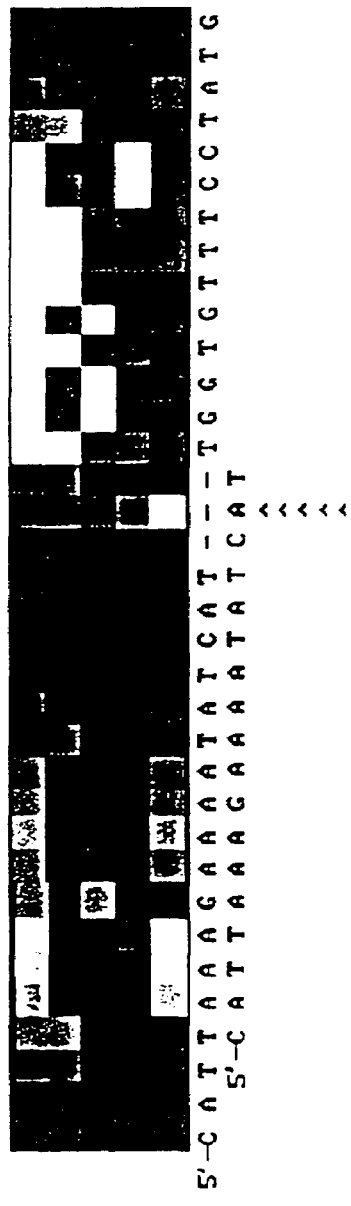
FIG. 12A
FIG. 12B
FIG. 12C

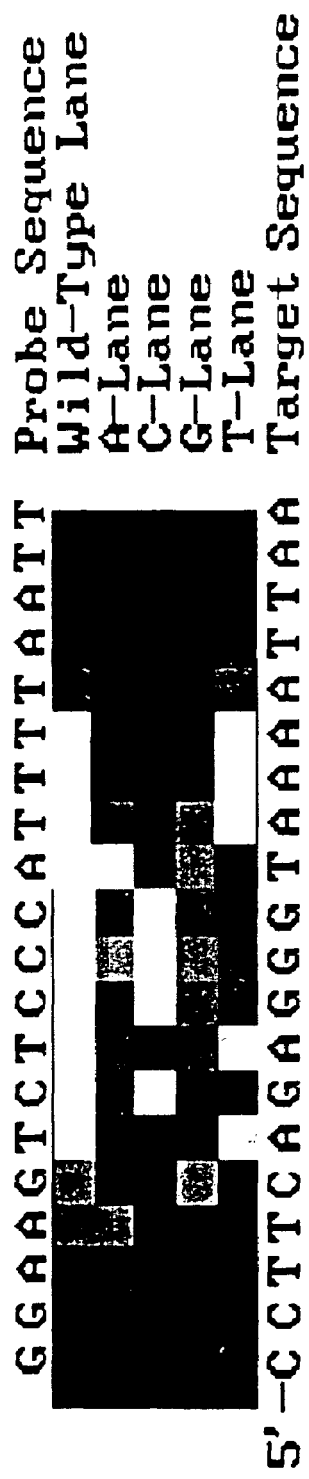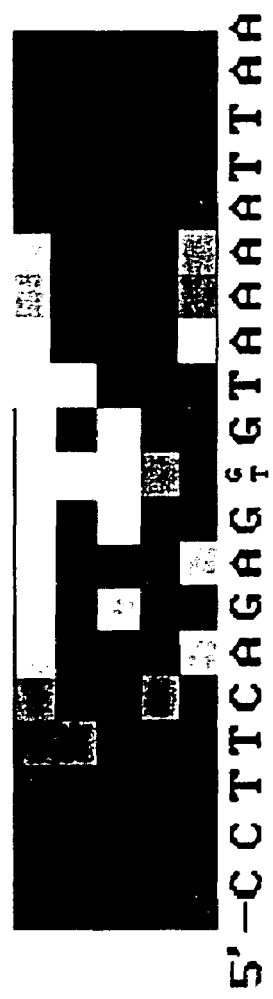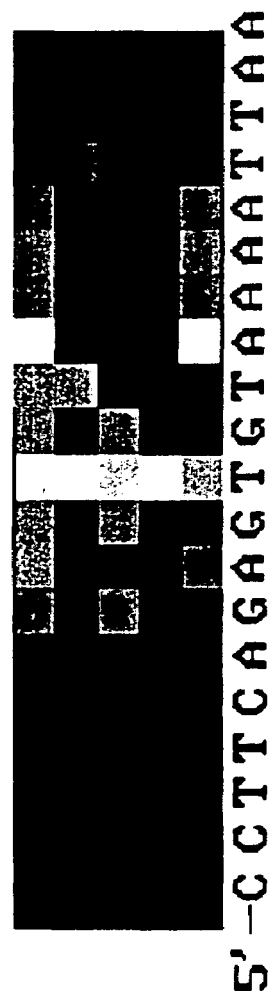
FIG. 14A
FIG. 14B
FIG. 14C (1 of 2)

(2 of 2)

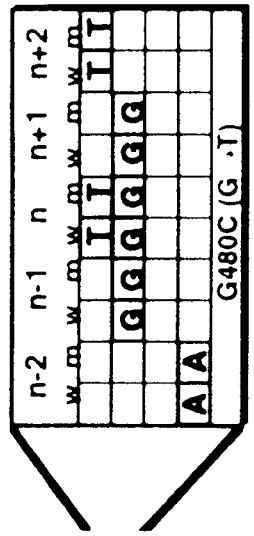
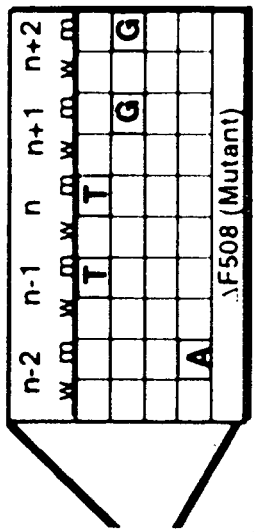
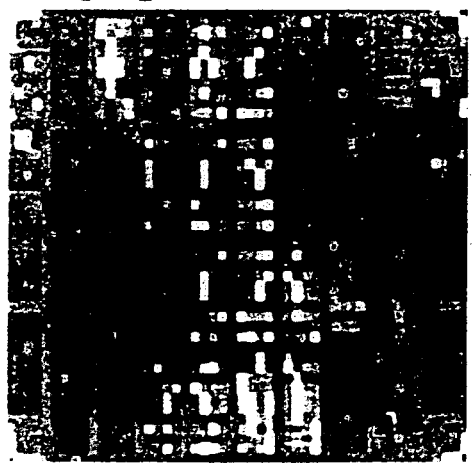
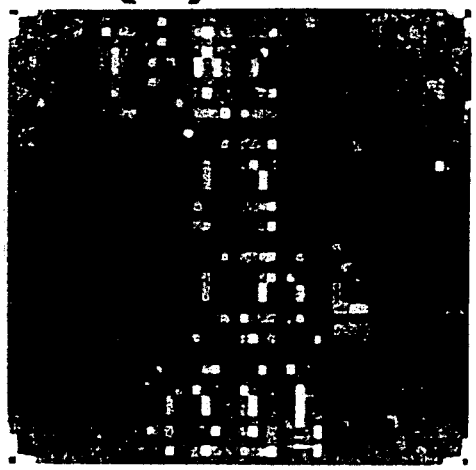
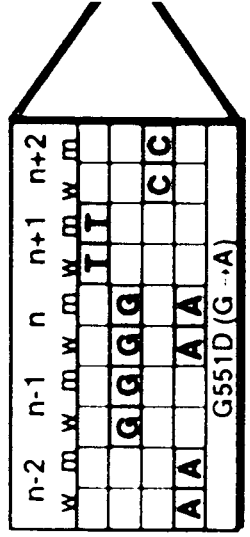
FIG. 20A
FIG. 20B

METHOD OF COMPARING A TARGET NUCLEIC ACID AND A REFERENCE NUCLEIC ACID

CROSS-REFERENCE TO RELATED APPLICATION

This application is a continuation of 08/544,381, filed: Oct. 10, 1995 (now U.S. Pat. No. 6,027,880), which is a continuation-in-part of U.S. Ser. No. 08/510,521, filed Aug. 2, 1995, now U.S. Pat. No. 7,115,364 which is a continuation-in-part of PCT/US94/12305, filed Oct. 26, 1994, which is a continuation-in-part of U.S. Ser. No. 08/284,064, filed Aug. 2, 1994 abandoned in favor of file wrapper continuation 08/781,550 (now U.S. Pat. No. 5,861,242), which is a continuation-in-part of U.S. Ser. No. 08/143,312, filed Oct. 26, 1993 abandoned in favor of file wrapper continuation 08/441,887 now U.S. Pat. No. 5,837,832, each of which is incorporated by reference in its entirety for all purposes.

Research leading to the invention was funded in part by NIH grant No. 1R01HG00813-01, and the government may have certain rights to the invention.

BACKGROUND OF THE INVENTION

1. Field of the Invention

The present invention provides arrays of oligonucleotide probes immobilized in microfabricated patterns on chips for analyzing a cystic fibrosis transmembrane conductance regulator (CFTR) gene.

2. Description of Related Art

There has been considerable interest in developing genetic tests for genes responsible for disorders such as cystic fibrosis. Major pathologies associated with cystic fibrosis occur in the lungs, pancreas, sweat glands, digestive and reproductive organs. The gene associated with cystic fibrosis, CFTR, is a large gene with complex mutation and polymorphism patterns that pose a significant challenge to existing genotyping strategies. The CFTR gene has 27 exons, which span over 250 kb of DNA. Over 500 mutations of various types (transitions, transversions, insertions, deletions and numerous polymorphisms) have been described.

Because the characterized CFTR mutations are widely distributed throughout the gene, existing genotyping assays focus only on the most common mutations. Some methods rely on using PCR to amplify regions surrounding mutations of interest and the characterizing the amplification products in a second analysis step, such as restriction fragment sizing, allele specific oligonucleotide hybridization, denaturing gradient gel electrophoresis, and single stranded conformational analysis. Alternatively, mutations have been analyzed using primers designed to amplify selectively mutant or wildtype sequences. None of these methods readily adopts to monitoring large regions of the CFTR gene, identifying hitherto uncharacterized mutations or simultaneously screening large numbers of mutations with a high degree of accuracy.

The development of VLSIPS™ technology has provided methods for making very large arrays of oligonucleotide probes in very small areas. See U.S. Pat. No. 5,143,854, WO 90/15070 and WO 92/10092, each of which is incorporated herein by reference. U.S. Ser. No. 08/082,937, filed Jun. 25, 1993, describes methods for making arrays of oligonucleotide probes that can be used to provide the complete sequence of a target nucleic acid and to detect the presence of a nucleic acid containing a specific nucleotide sequence. Others have also proposed the use of large numbers of oligonucleotide probes to provide the complete nucleic acid sequence of a target nucleic acid but failed to provide an enabling method for using arrays of immobilized probes for this purpose. See U.S. Pat. Nos. 5,202,231, 5,002,867 and WO 93/17126.

Microfabricated arrays of large numbers of oligonucleotide probes, called "DNA chips" offer great promise for a wide variety of applications. The present application describes the use of such chips for inter alia analysis of the CFTR gene and detection of mutations therein.

SUMMARY OF THE INVENTION

The invention provides several strategies employing immobilized arrays of probes for comparing a reference sequence of known sequence with a target sequence showing substantial similarity with the reference sequence, but differing in the presence of, e.g., mutations. In a first embodiment, the invention provides a tiling strategy employing an array of immobilized oligonucleotide probes comprising at least two sets of probes. A first probe set comprises a plurality of probes, each probe comprising a segment of at least three nucleotides exactly complementary to a subsequence of the reference sequence, the segment including at least one interrogation position complementary to a corresponding nucleotide in the reference sequence. A second probe set comprises a corresponding probe for each probe in the first probe set, the corresponding probe in the second probe set being identical to a sequence comprising the corresponding probe from the first probe set or a subsequence of at least three nucleotides thereof that includes the at least one interrogation position, except that the at least one interrogation position is occupied by a different nucleotide in each of the two corresponding probes from the first and second probe sets. The probes in the first probe set have at least two interrogation positions corresponding to two contiguous nucleotides in the reference sequence. One interrogation position corresponds to one of the contiguous nucleotides, and the other interrogation position to the other.

In a second embodiment, the invention provides a tiling strategy employing an array comprising four probe sets. A first probe set comprises a plurality of probes, each probe comprising a segment of at least three nucleotides exactly complementary to a subsequence of the reference sequence, the segment including at least one interrogation position complementary to a corresponding nucleotide in the reference sequence. Second, third and fourth probe sets each comprise a corresponding probe for each probe in the first probe set. The probes in the second, third and fourth probe sets are identical to a sequence comprising the corresponding probe from the first probe set or a subsequence of at least three nucleotides thereof that includes the at least one interrogation position, except that the at least one interrogation position is occupied by a different nucleotide in each of the four corresponding probes from the four probe sets. The first probe set often has at least 100 interrogation positions corresponding to 100 contiguous nucleotides in the reference sequence. Sometimes the first probe set has an interrogation position corresponding to every nucleotide in the reference sequence. The segment of complementarity within the probe set is usually about 9-21 nucleotides. Although probes may contain leading or trailing sequences in addition to the 9-21 sequences, many probes consist exclusively of a 9-21 segment of complementarity.

In a third embodiment, the invention provides immobilized arrays of probes tiled for multiple reference sequences. One such array comprises at least one pair of first and second probe groups, each group comprising first and second sets of probes as defined in the first embodiment. Each probe in the first probe set from the first group is exactly complementary to a subsequence of a first reference sequence, and each probe in the first probe set from the second group is exactly complementary to a subsequence of a second reference sequence. Thus, the first group of probes are tiled with respect to a first reference sequence and the second group of probes with respect to a second reference sequence. Each group of probes can also include third and fourth sets of probes as defined in the second embodiment. In some arrays of this type, the second reference sequence is a mutated form of the first reference sequence.

In a fourth embodiment, the invention provides arrays for block tiling. Block tiling is a species of the basic tiling strategies described above. The usual unit of a block tiling array is a group of probes comprising a perfectly matched probe, a first set of three mismatched probes and a second set of three mismatched probes. The perfectly matched probe comprises a segment of at least three nucleotides exactly complementary to a subsequence of a reference sequence. The segment has at least first and second interrogation positions corresponding to first and second nucleotides in the reference sequence. The probes in the first set of three mismatched probes are each identical to a sequence comprising the perfectly matched probe or a subsequence of at least three nucleotides thereof including the first and second interrogation positions, except in the first interrogation position, which is occupied by a different nucleotide in each of the three mismatched probes and the perfectly matched probe. The probes in the second set of three mismatched probes are each identical to a sequence comprising the perfectly matched probe or a subsequence of at least three nucleotides thereof including the first and second interrogation positions, except in the second interrogation position, which is occupied by a different nucleotide in each of the three mismatched probes and the perfectly matched probe.

In a fifth embodiment, the invention provides methods of comparing a target sequence with a reference sequence using arrays of immobilized pooled probes. The arrays employed in these methods represent a further species of the basic tiling arrays noted above. In these methods, variants of a reference sequence differing from the reference sequence in at least one nucleotide are identified and each is assigned a designation. An array of pooled probes is provided, with each pool occupying a separate cell of the array. Each pool comprises a probe comprising a segment exactly complementary to each variant sequence assigned a particular designation. The array is then contacted with a target sequence comprising a variant of the reference sequence. The relative hybridization intensities of the pools in the array to the target sequence are determined. The identity of the target sequence is deduced from the pattern of hybridization intensities. Often, each variant is assigned a designation having at least one digit and at least one value for the digit. In this case, each pool comprises a probe comprising a segment exactly complementary to each variant sequence assigned a particular value in a particular digit. When variants are assigned successive numbers in a numbering system of base m having n digits, n×(m−1) pooled probes are used to assign each variant a designation.

In a sixth embodiment, the invention provides a pooled probe for trellis tiling, a further species of the basic tiling strategy. In trellis tiling, the identity of a nucleotide in a target sequence is determined from a comparison of hybridization intensities of three pooled trellis probes. A pooled trellis probe comprises a segment exactly complementary to a subsequence of a reference sequence except at a first interrogation position occupied by a pooled nucleotide N, a second interrogation position occupied by a pooled nucleotide selected from the group of three consisting of (1) M or K, (2) R or Y and (3) S or W, and a third interrogation position occupied by a second pooled nucleotide selected from the group. The pooled nucleotide occupying the second interrogation position comprises a nucleotide complementary to a corresponding nucleotide from the reference sequence when the second pooled probe and reference sequence are maximally aligned, and the pooled nucleotide occupying the third interrogation position comprises a nucleotide complementary to a corresponding nucleotide from the reference sequence when the third pooled probe and the reference sequence are maximally aligned. Standard IUPAC nomenclature is used for describing pooled nucleotides.

In trellis tiling, an array comprises at least first, second and third cells, respectively occupied by first, second and third pooled probes, each according to the generic description above. However, the segment of complementarity, location of interrogation positions, and selection of pooled nucleotide at each interrogation position may or may not differ between the three pooled probes subject to the following constraint. One of the three interrogation positions in each of the three pooled probes must align with the same corresponding nucleotide in the reference sequence. This interrogation position must be occupied by a N in one of the pooled probes, and a different pooled nucleotide in each of the other two pooled probes.

In a seventh embodiment, the invention provides arrays for bridge tiling. Bridge tiling is a species of the basic tiling strategies noted above, in which probes from the first probe set contain more than one segment of complementarity. In bridge tiling, a nucleotide in a reference sequence is usually determined from a comparison of four probes. A first probe comprises at least first and second segments, each of at least three nucleotides and each exactly complementary to first and second subsequences of a reference sequences. The segments including at least one interrogation position corresponding to a nucleotide in the reference sequence. Either (1) the first and second subsequences are noncontiguous in the reference sequence, or (2) the first and second subsequences are contiguous and the first and second segments are inverted relative to the first and second subsequences. The arrays further comprises second, third and fourth probes, which are identical to a sequence comprising the first probe or a subsequence thereof comprising at least three nucleotides from each of the first and second segments, except in the at least one interrogation position, which differs in each of the probes. In a species of bridge tiling, referred to as deletion tiling, the first and second subsequences are separated by one or two nucleotides in the reference sequence.

In an eighth embodiment, the invention provides arrays of probes for multiplex tiling. Multiplex tiling is a strategy, in which the identity of two nucleotides in a target sequence is determined from a comparison of the hybridization intensities of four probes, each having two interrogation positions. Each of the probes comprising a segment of at least 7 nucleotides that is exactly complementary to a subsequence from a reference sequence, except that the segment may or may not be exactly complementary at two interrogation positions. The nucleotides occupying the interrogation positions are selected by the following rules: (1) the first interrogation position is occupied by a different nucleotide in each of the four probes, (2) the second interrogation position is occupied by a different nucleotide in each of the four probes, (3) in first and second probes, the segment is exactly complementary to the subsequence, except at no more than one of the interrogation positions, (4) in third and fourth probes, the segment is exactly complementary to the subsequence, except at both of the interrogation positions.

In a ninth embodiment, the invention provides arrays of immobilized probes including helper mutations. Helper mutations are useful for, e.g., preventing self-annealing of probes having inverted repeats. In this strategy, the identity of a nucleotide in a target sequence is usually determined from a comparison of four probes. A first probe comprises a segment of at least 7 nucleotides exactly complementary to a subsequence of a reference sequence except at one or two positions, the segment including an interrogation position not at the one or two positions. The one or two positions are occupied by helper mutations. Second, third and fourth mutant probes are each identical to a sequence comprising the perfectly matched probe or a subsequence thereof including the interrogation position and the one or two positions, except in the interrogation position, which is occupied by a different nucleotide in each of the four probes.

In a tenth embodiment, the invention provides arrays of probes comprising at least two probe sets, but lacking a probe set comprising probes that are perfectly matched to a reference sequence. Such arrays are usually employed in methods in which both reference and target sequence are hybridized to the array. The first probe set comprising a plurality of probes, each probe comprising a segment exactly complementary to a subsequence of at least 3 nucleotides of a reference sequence except at an interrogation position. The second probe set comprises a corresponding probe for each probe in the first probe set, the corresponding probe in the second probe set being identical to a sequence comprising the corresponding probe from the first probe set or a subsequence of at least three nucleotides thereof that includes the interrogation position, except that the interrogation position is occupied by a different nucleotide in each of the two corresponding probes and the complement to the reference sequence.

In an eleventh embodiment, the invention provides methods of comparing a target sequence with a reference sequence comprising a predetermined sequence of nucleotides using any of the arrays described above. The methods comprise hybridizing the target nucleic acid to an array and determining which probes, relative to one another, in the array bind specifically to the target nucleic acid. The relative specific binding of the probes indicates whether the target sequence is the same or different from the reference sequence. In some such methods, the target sequence has a substituted nucleotide relative to the reference sequence in at least one undetermined position, and the relative specific binding of the probes indicates the location of the position and the nucleotide occupying the position in the target sequence. In some methods, a second target nucleic acid is also hybridized to the array. The relative specific binding of the probes then indicates both whether the target sequence is the same or different from the reference sequence, and whether the second target sequence is the same or different from the reference sequence. In some methods, when the array comprises two groups of probes tiled for first and second reference sequences, respectively, the relative specific binding of probes in the first group indicates whether the target sequence is the same or different from the first reference sequence. The relative specific binding of probes in the second group indicates whether the target sequence is the same or different from the second reference sequence. Such methods are particularly useful for analyzing heterologous alleles of a gene. Some methods entail hybridizing both a reference sequence and a target sequence to any of the arrays of probes described above. Comparison of the relative specific binding of the probes to the reference and target sequences indicates whether the target sequence is the same or different from the reference sequence.

BRIEF DESCRIPTION OF THE FIGURES

FIG. 4A: Exemplary arrangement of lanes on a chip. The chip shows four probe sets, each having five probes and each having a total of five interrogation positions (I1-I5), one per probe.

FIG. 4B: A tiling strategy for analyzing closing spaced mutations.

FIG. 4C: A tiling strategy for avoiding loss of signal due to probe self-annealing. The reference sequence is (SEQ. ID. No. 207).

FIG. 6: Strategies for detecting deletion and insertion mutations. Bases in brackets may or may not be present.

FIG. 7: Block tiling strategy. The perfectly matched probe has three interrogation positions. The probes from the other probe sets have only one of these interrogation positions.

FIG. 8: Multiplex tiling strategy. Each probe has two interrogation positions.

FIG. 9: Helper mutation strategy. The segment of complementarity differs from the complement of the reference sequence (SEQ. ID. No. 214) at a helper mutation as well as the interrogation position.

FIG. 12, in panels A, B, and C, shows an image made from the region of a DNA chip containing CFTR exon 10 probes; in panel A, the chip was hybridized to a wild-type target; in panel C, the chip was hybridized to a mutant ΔF508 target; and in panel B, the chip was hybridized to a mixture of the wild-type and mutant targets (SEQ. ID. Nos. 217-220).

FIG. 14, in panels A (SEQ. ID. No. 226), B (SEQ. ID. Nos. 224,225), and C (SEQ. ID. No. 227), shows an image made from a region of a DNA chip containing CFTR exon 10 probes; in panel A, the chip was hybridized to the wt480 target; in panel C, the chip was hybridized to the mu480 target; and in panel B, the chip was hybridized to a mixture of the wild-type and mutant targets.

FIG. 19 (SEQ. ID. Nos. 249-250): Hybridization of R553X-Specific Array to Wildtype and Mutant Targets.

FIG. 20: Images of a chip containing 37 mutation specific subarrays hybridized to various targets. Fifteen of the subarrays are specific for mutations in exons 10 and 11. FIG. 20A: Hybridization with exon 10 and exon 11 targets multiplexed from a compound heterozygous genomic DNA sample with G551D and G480C mutations. Diagrams of the G551D and G480C mutation subarrays indicating probes fully complementary to the wild type and mutant sequences are at the sides of the image. FIG. 20B: Hybridization with exon 10 and exon 11 targets multiplexed from a genomic DNA sample homozygous for the ΔF508 deletion.

DETAILED DESCRIPTION OF THE INVENTION

Figure 1:
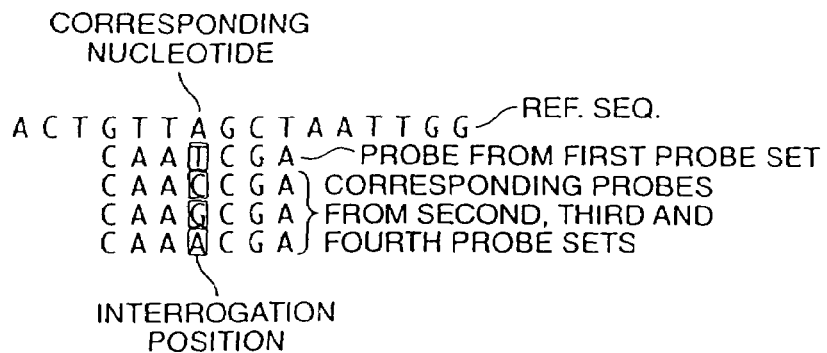
FIG. 1: Basic tiling strategy. The figure illustrates the relationship between an interrogation position (I) and a corresponding nucleotide (n) in the reference sequence (SEQ. ID. No. 192), and between a probe from the first probe set and corresponding probes from second, third and fourth probe sets.

The invention provides a number of strategies for comparing a polynucleotide of known sequence (a reference sequence) with variants of that sequence (target sequences). The comparison can be performed at the level of entire genomes, chromosomes, genes, exons or introns, or can focus on individual mutant sites and immediately adjacent bases. The strategies allow detection of variations, such as mutations or polymorphisms, in the target sequence irrespective whether a particular variant has previously been characterized. The strategies both define the nature of a variant and identify its location in a target sequence.

The strategies employ arrays of oligonucleotide probes immobilized to a solid support. Target sequences are analyzed by determining the extent of hybridization at particular probes in the array. The strategy in selection of probes facilitates distinction between perfectly matched probes and probes showing single-base or other degrees of mismatches. The strategy usually entails sampling each nucleotide of interest in a target sequence several times, thereby achieving a high degree of confidence in its identity. This level of confidence is further increased by sampling of adjacent nucleotides in the target sequence to nucleotides of interest. The present tiling strategies result in sequencing and comparison methods suitable for routine large-scale practice with a high degree of confidence in the sequence output.

I. General Tiling Strategies

A. Selection of Reference Sequence

The chips are designed to contain probes exhibiting complementarity to one or more selected reference sequence whose sequence is known. The chips are used to read a target sequence comprising either the reference sequence itself or variants of that sequence. Target sequences may differ from the reference sequence at one or more positions but show a high overall degree of sequence identity with the reference sequence (e.g., at least 75, 90, 95, 99, 99.9 or 99.99%). Any polynucleotide of known sequence can be selected as a reference sequence. Reference sequences of interest include sequences known to include mutations or polymorphisms associated with phenotypic changes having clinical significance in human patients. For example, the CFTR gene and P53 gene in humans have been identified as the location of several mutations resulting in cystic fibrosis or cancer respectively. Other reference sequences of interest include those that serve to identify pathogenic microorganisms and/or are the site of mutations by which such microorganisms acquire drug resistance (e.g., the HIV reverse transcriptase gene). Other reference sequences of interest include regions where polymorphic variations are known to occur (e.g., the D-loop region of mitochondrial DNA). These reference sequences have utility for, e.g., forensic or epidemiological studies. Other reference sequences of interest include p34 (related to p53), p65 (implicated in breast, prostate and liver cancer), and DNA segments encoding cytochromes P450 and other biotransformation genes (see Meyer et al., *Pharmac. Ther.* 46, 349-355 (1990)). Other reference sequences of interest include those from the genome of pathogenic viruses (e.g., hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus. Other reference sequences of interest are from genomes or episomes of pathogenic bacteria, particularly regions that confer drug resistance or allow phylogenic characterization of the host (e.g., 16S rRNA or corresponding DNA). For example, such bacteria include *chlamydia, rickettsial* bacteria, *mycobacteria, staphylococci, treptocci, pneumonococci, meningococci* and *conococci, klebsiella, proteus, serratia, pseudomonas, legionella, diphtheria, salmonella, bacilli, cholera, tetanus, botulism, anthrax, plague, leptospirosis,* and *Lymes disease* bacteria. Other reference sequences of interest include those in which mutations result in the following autosomal recessive disorders: sickle cell anemia, β-thalassemia, phenylketonuria, galactosemia, Wilson's disease, hemochromatosis, severe combined immunodeficiency, alpha-1-antitrypsin deficiency, albinism, alkaptonuria, lysosomal storage diseases and Ehlers-Danlos syndrome. Other reference sequences of interest include those in which mutations result in X-linked recessive disorders: hemophilia, glucose-6-phosphate dehydrogenase, agammaglobulimenia, diabetes insipidus, Lesch-Nyhan syndrome, muscular dystrophy, Wiskott-Aldrich syndrome, Fabry's disease and fragile X-syndrome. Other reference sequences of interest includes those in which mutations result in the following autosomal dominant disorders: familial hypercholesterolemia, polycystic kidney disease, Huntingdon's disease, hereditary spherocytosis, Marfan's syndrome, von Willebrand's disease, neurofibromatosis, tuberous sclerosis, hereditary hemorrhagic telangiectasia, familial colonic polyposis, Ehlers-Danlos syndrome, myotonic dystrophy, muscular dystrophy, osteogenesis imperfecta, acute intermittent porphyria, and von Hippel-Lindau disease.

The length of a reference sequence can vary widely from a full-length genome, to an individual chromosome, episome, gene, component of a gene, such as an exon, intron or regulatory sequences, to a few nucleotides. A reference sequence of between about 2, 5, 10, 20, 50, 100, 5000, 1000, 5,000 or 10,000, 20,000 or 100,000 nucleotides is common. Sometimes only particular regions of a sequence (e.g., exons of a gene) are of interest. In such situations, the particular regions can be considered as separate reference sequences or can be considered as components of a single reference sequence, as matter of arbitrary choice.

A reference sequence can be any naturally occurring, mutant, consensus or purely hypothetical sequence of nucleotides, RNA or DNA. For example, sequences can be obtained from computer data bases, publications or can be determined or conceived de novo. Usually, a reference sequence is selected to show a high degree of sequence identity to envisaged target sequences. Often, particularly, where a significant degree of divergence is anticipated between target sequences, more than one reference sequence is selected. Combinations of wildtype and mutant reference sequences are employed in several applications of the tiling strategy.

B. Chip Design

1. Basic Tiling Strategy

The basic tiling strategy provides an array of immobilized probes for analysis of target sequences showing a high degree of sequence identity to one or more selected reference sequences. The strategy is first illustrated for an array that is subdivided into four probe sets, although it will be apparent that in some situations, satisfactory results are obtained from only two probe sets. A first probe set comprises a plurality of probes exhibiting perfect complementarity with a selected reference sequence. The perfect complementarity usually exists throughout the length of the probe. However, probes having a segment or segments of perfect complementarity that is/are flanked by leading or trailing sequences lacking complementarity to the reference sequence can also be used. Within a segment of complementarity, each probe in the first probe set has at least one interrogation position that corresponds to a nucleotide in the reference sequence. That is, the interrogation position is aligned with the corresponding nucleotide in the reference sequence, when the probe and reference sequence are aligned to maximize complementarity between the two. If a probe has more than one interrogation position, each corresponds with a respective nucleotide in the reference sequence. The identity of an interrogation position and corresponding nucleotide in a particular probe in the first probe set cannot be determined simply by inspection of the probe in the first set. As will become apparent, an interrogation position and corresponding nucleotide is defined by the comparative structures of probes in the first probe set and corresponding probes from additional probe sets.

In principle, a probe could have an interrogation position at each position in the segment complementary to the reference sequence. Sometimes, interrogation positions provide more accurate data when located away from the ends of a segment of complementarity. Thus, typically a probe having a segment of complementarity of length x does not contain more than x-2 interrogation positions. Since probes are typically 9-21 nucleotides, and usually all of a probe is complementary, a probe typically has 1-19 interrogation positions. Often the probes contain a single interrogation position, at or near the center of probe.

Figure 2:
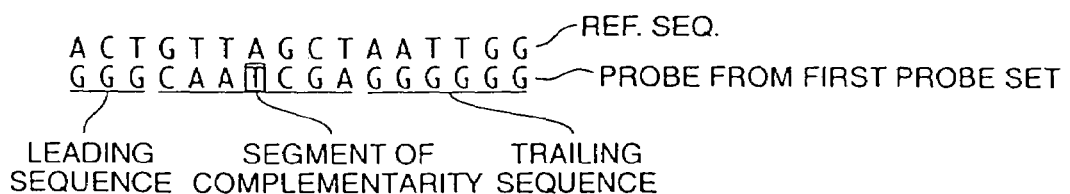
FIG. 2: Segment of complementarity in a probe from the first probe set (SEQ. ID. No. 193).

For each probe in the first set, there are, for purposes of the present illustration, up to three corresponding probes from three additional probe sets. See FIG. 1. Thus, there are four probes corresponding to each nucleotide of interest in the reference sequence. Each of the four corresponding probes has an interrogation position aligned with that nucleotide of interest. Usually, the probes from the three additional probe sets are identical to the corresponding probe from the first probe set with one exception. The exception is that at least one (and often only one) interrogation position, which occurs in the same position in each of the four corresponding probes from the four probe sets, is occupied by a different nucleotide in the four probe sets. For example, for an A nucleotide in the reference sequence, the corresponding probe from the first probe set has its interrogation position occupied by a T, and the corresponding probes from the additional three probe sets have their respective interrogation positions occupied by A, C, or G, a different nucleotide in each probe. Of course, if a probe from the first probe set comprises trailing or flanking sequences lacking complementarity to the reference sequences (see FIG. 2), these sequences need not be present in corresponding probes from the three additional sets. Likewise corresponding probes from the three additional sets can contain leading or trailing sequences outside the segment of complementarity that are not present in the corresponding probe from the first probe set. Occasionally, the probes from the additional three probe set are identical (with the exception of interrogation position(s)) to a contiguous subsequence of the full complementary segment of the corresponding probe from the first probe set. In this case, the subsequence includes the interrogation position and usually differs from the full-length probe only in the omission of one or both terminal nucleotides from the termini of a segment of complementarity. That is, if a probe from the first probe set has a segment of complementarity of length n, corresponding probes from the other sets will usually include a subsequence of the segment of at least length n-2. Thus, the subsequence is usually at least 3, 4, 7, 9, 15, 21, or 25 nucleotides long, most typically, in the range of 9-21 nucleotides. The subsequence should be sufficiently long to allow a probe to hybridize detectably more strongly to a variant of the reference sequence mutated at the interrogation position than to the reference sequence.

The probes can be oligodeoxyribonucleotides or oligoribonucleotides, or any modified forms of these polymers that are capable of hybridizing with a target nucleic sequence by complementary base-pairing. Complementary base pairing means sequence-specific base pairing which includes e.g., Watson-Crick base pairing as well as other forms of base pairing such as Hoogsteen base pairing. Modified forms include 2'-O-methyl oligoribonucleotides and so-called PNAs, in which oligodeoxyribonucleotides are linked via peptide bonds rather than phophodiester bonds. The probes can be attached by any linkage to a support (e.g., 3', 5' or via the base). 3' attachment is more usual as this orientation is compatible with the preferred chemistry for solid phase synthesis of oligonucleotides.

The number of probes in the first probe set (and as a consequence the number of probes in additional probe sets) depends on the length of the reference sequence, the number of nucleotides of interest in the reference sequence and the number of interrogation positions per probe. In general, each nucleotide of interest in the reference sequence requires the same interrogation position in the four sets of probes. Consider, as an example, a reference sequence of 100 nucleotides, 50 of which are of interest, and probes each having a single interrogation position. In this situation, the first probe set requires fifty probes, each having one interrogation position corresponding to a nucleotide of interest in the reference sequence. The second, third and fourth probe sets each have a corresponding probe for each probe in the first probe set, and so each also contains a total of fifty probes. The identity of each nucleotide of interest in the reference sequence is determined by comparing the relative hybridization signals at four probes having interrogation positions corresponding to that nucleotide from the four probe sets.

In some reference sequences, every nucleotide is of interest. In other reference sequences, only certain portions in which variants (e.g., mutations or polymorphisms) are concentrated are of interest. In other reference sequences, only particular mutations or polymorphisms and immediately adjacent nucleotides are of interest. Usually, the first probe set has interrogation positions selected to correspond to at least a nucleotide (e.g., representing a point mutation) and one immediately adjacent nucleotide. Usually, the probes in the first set have interrogation positions corresponding to at least 3, 10, 50, 100, 1000, or 20,000 contiguous nucleotides. The probes usually have interrogation positions corresponding to at least 5, 10, 30, 50, 75, 90, 99 or sometimes 100% of the nucleotides in a reference sequence. Frequently, the probes in the first probe set completely span the reference sequence and overlap with one another relative to the reference sequence. For example, in one common arrangement each probe in the first probe set differs from another probe in that set by the omission of a 3' base complementary to the reference sequence and the acquisition of a 5' base complementary to the reference sequence. See FIGS. 3A and 3B.

The number of probes on the chip can be quite large (e.g., $10^5$-$10^6$). However, often only a relatively small proportion (i.e., less than about 50%, 25%, 10%, 5% or 1%) of the total number of probes of a given length are selected to pursue a particular tiling strategy. For example, a complete set of octomer probes comprises 65,536 probes; thus, an array of the invention typically has fewer than 32,768 octomer probes. A complete array of decamer probes comprises 1,048,576 probes; thus, an array of the invention typically has fewer than about 500,000 decamer probes. Often arrays have a lower limit of 25, 50 or 100 probes and an upper limit of 1,000,000, 100,000, 10,000 or 1000 probes. The arrays can have other components besides the probes such as linkers attaching the probes to a support.

Some advantages of the use of only a proportion of all possible probes of a given length include: (i) each position in the array is highly informative, whether or not hybridization occurs; (ii) nonspecific hybridization is minimized; (iii) it is straightforward to correlate hybridization differences with sequence differences, particularly with reference to the hybridization pattern of a known standard; and (iv) the ability to address each probe independently during synthesis, using high resolution photolithography, allows the array to be designed and optimized for any sequence. For example the length of any probe can be varied independently of the others.

Figure 3A:
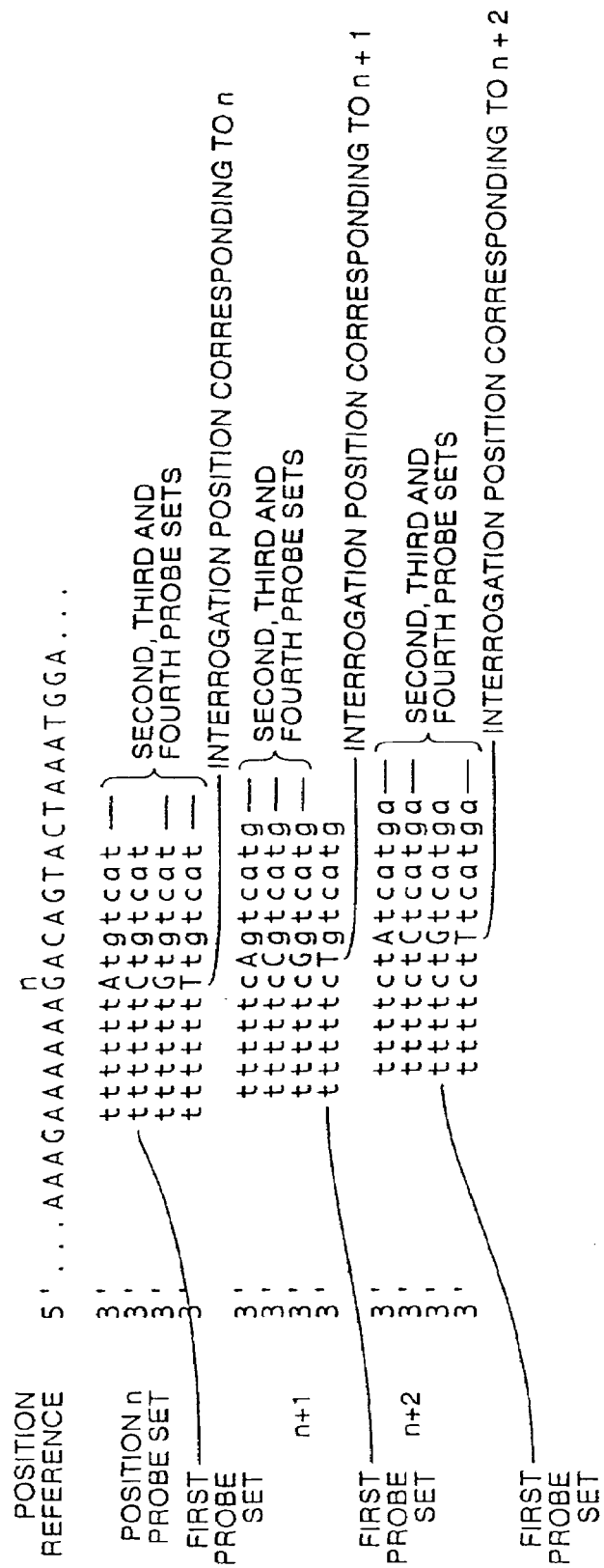
FIG. 3A: Incremental succession of probes in a basic tiling strategy. The figure shows four probe sets, each having three probes. Note that each probe differs from its predecessor in the same set by the acquisition of a 5' nucleotide and the loss of a 3' nucleotide, as well as in the nucleotide occupying the interrogation position.
Figure 3B:
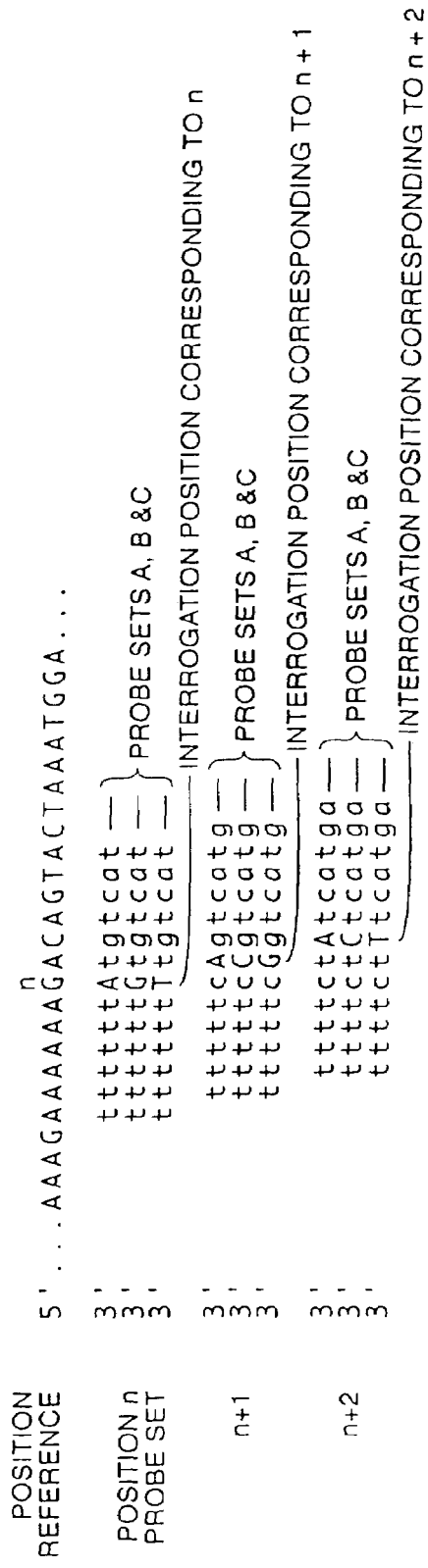
FIG. 3B: Arrangement of probe sets in tiling arrays lacking a perfectly matched probe set.
Figure 5:
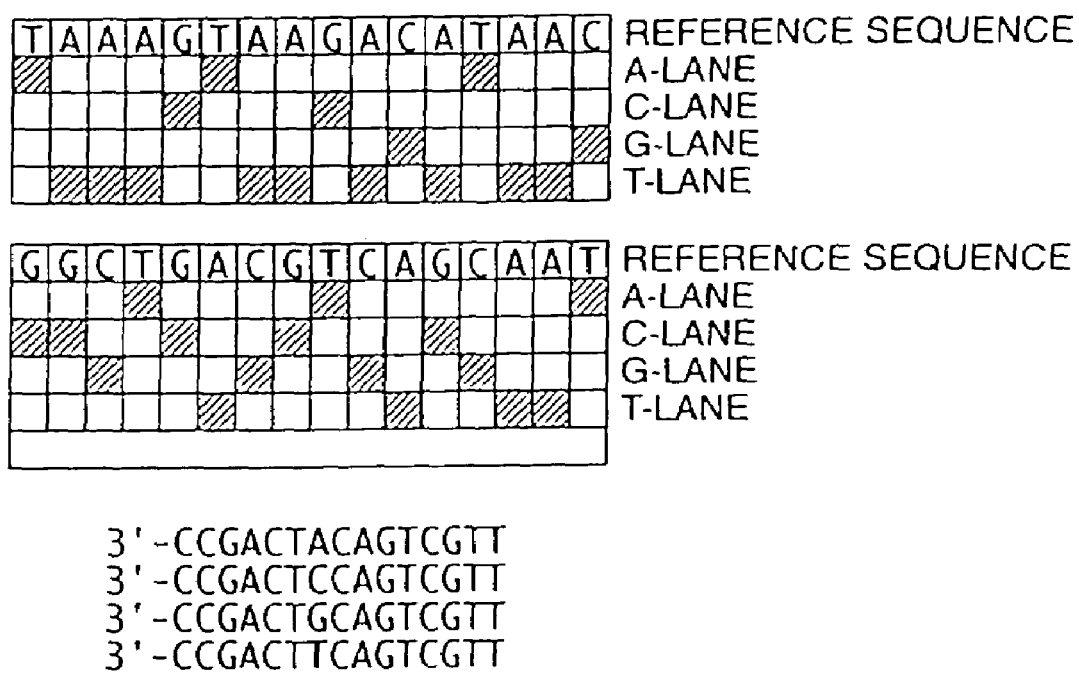
FIG. 5: Hybridization pattern of chip having probes laid down in lanes. Dark patches indicate hybridization. The probes in the lower part of the figure (SEQ. ID. Nos. 210-213) occur at the column of the array indicated by the arrow when the probes length is 15 and the interrogation position 7. The reference sequences are (SEQ. ID. Nos. 208-209).

For conceptual simplicity, the probes in a set are usually arranged in order of the sequence in a lane across the chip. A lane contains a series of overlapping probes, which represent or tile across, the selected reference sequence (see FIGS. 3A and 3B). The components of the four sets of probes are usually laid down in four parallel lanes, collectively constituting a row in the horizontal direction and a series of 4-member columns in the vertical direction. Corresponding probes from the four probe sets (i.e., complementary to the same subsequence of the reference sequence) occupy a column. Each probe in a lane usually differs from its predecessor in the lane by the omission of a base at one end and the inclusion of additional base at the other end as shown in FIGS. 3A and 3B. However, this orderly progression of probes can be interrupted by the inclusion of control probes or omission of probes in certain columns of the array. Such columns serve as controls to orient the chip, or gauge the background, which can include target sequence nonspecifically bound to the chip.

The probes sets are usually laid down in lanes such that all probes having an interrogation position occupied by an A form an A-lane, all probes having an interrogation position occupied by a C form a C-lane, all probes having an interrogation position occupied by a G form a G-lane, and all probes having an interrogation position occupied by a T (or U) form a T lane (or a U lane). Note that in this arrangement there is not a unique correspondence between probe sets and lanes. Thus, the probe from the first probe set is laid down in the A-lane, C-lane, A-lane, A-lane and T-lane for the five columns in FIG. 4A. The interrogation position on a column of probes corresponds to the position in the target sequence whose identity is determined from analysis of hybridization to the probes in that column. Thus, $I_1$-$I_5$ respectively correspond to $N_1$-$N_5$ in FIG. 4A. The interrogation position can be anywhere in a probe but is usually at or near the central position of the probe to maximize differential hybridization signals between a perfect match and a single-base mismatch. For example, for an 11 mer probe, the central position is the sixth nucleotide.

Although the array of probes is usually laid down in rows and columns as described above, such a physical arrangement of probes on the chip is not essential. Provided that the spatial location of each probe in an array is known, the data from the probes can be collected and processed to yield the sequence of a target irrespective of the physical arrangement of the probes on a chip. In processing the data, the hybridization signals from the respective probes can be reassorted into any conceptual array desired for subsequent data reduction whatever the physical arrangement of probes on the chip.

A range of lengths of probes can be employed in the chips. As noted above, a probe may consist exclusively of a complementary segments, or may have one or more complementary segments juxtaposed by flanking, trailing and/or intervening segments. In the latter situation, the total length of complementary segment(s) is more important that the length of the probe. In functional terms, the complementary segment(s) of the first probe sets should be sufficiently long to allow the probe to hybridize detectably more strongly to a reference sequence compared with a variant of the reference including a single base mutation at the nucleotide corresponding to the interrogation position of the probe. Similarly, the complementary segment(s) in corresponding probes from additional probe sets should be sufficiently long to allow a probe to hybridize detectably more strongly to a variant of the reference sequence having a single nucleotide substitution at the interrogation position relative to the reference sequence. A probe usually has a single complementary segment having a length of at least 3 nucleotides, and more usually at least 5, 6, 7, 8, 9, 10, 11, 12, 13, 14, 15, 16, 17, 18, 19, 20, 21, 22, 23, 24, 25 or 30 bases exhibiting perfect complementarity (other than possibly at the interrogation position(s) depending on the probe set) to the reference sequence. In bridging strategies, where more than one segment of complementarity is present, each segment provides at least three complementary nucleotides to the reference sequence and the combined segments provide at least two segments of three or a total of six complementary nucleotides. As in the other strategies, the combined length of complementary segments is typically from 6-30 nucleotides, and preferably from about 9-21 nucleotides. The two segments are often approximately the same length. Often, the probes (or segment of complementarity within probes) have an odd number of bases, so that an interrogation position can occur in the exact center of the probe.

In some chips, all probes are the same length. Other chips employ different groups of probe sets, in which case the probes are of the same size within a group, but differ between different groups. For example, some chips have one group comprising four sets of probes as described above in which all the probes are 11 mers, together with a second group comprising four sets of probes in which all of the probes are 13 mers. Of course, additional groups of probes can be added. Thus, some chips contain, e.g., four groups of probes having sizes of 11 mers, 13 mers, 15 mers and 17 mers. Other chips have different size probes within the same group of four probe sets. In these chips, the probes in the first set can vary in length independently of each other. Probes in the other sets are usually the same length as the probe occupying the same column from the first set. However, occasionally different lengths of probes can be included at the same column position in the four lanes. The different length probes are included to equalize hybridization signals from probes irrespective of whether A-T or C-G bonds are formed at the interrogation position.

The length of probe can be important in distinguishing between a perfectly matched probe and probes showing a single-base mismatch with the target sequence. The discrimination is usually greater for short probes. Shorter probes are usually also less susceptible to formation of secondary structures. However, the absolute amount of target sequence bound, and hence the signal, is greater for larger probes. The probe length representing the optimum compromise between these competing considerations may vary depending on inter alia the GC content of a particular region of the target DNA sequence, secondary structure, synthesis efficiency and cross-hybridization. In some regions of the target, depending on hybridization conditions, short probes (e.g., 11 mers) may provide information that is inaccessible from longer probes (e.g., 19 mers) and vice versa. Maximum sequence information can be read by including several groups of different sized probes on the chip as noted above. However, for many regions of the target sequence, such a strategy provides redundant information in that the same sequence is read multiple times from the different groups of probes. Equivalent information can be obtained from a single group of different sized probes in which the sizes are selected to maximize readable sequence at particular regions of the target sequence. The strategy of customizing probe length within a single group of probe sets minimizes the total number of probes required to read a particular target sequence. This leaves ample capacity for the chip to include probes to other reference sequences.

The invention provides an optimization block which allows systematic variation of probe length and interrogation position to optimize the selection of probes for analyzing a particular nucleotide in a reference sequence. The block comprises alternating columns of probes complementary to the wildtype target and probes complementary to a specific mutation. The interrogation position is varied between columns and probe length is varied down a column. Hybridization of the chip to the reference sequence or the mutant form of the reference sequence identifies the probe length and interrogation position providing the greatest differential hybridization signal.

Variation of interrogation position in probes for analyzing different regions of a target sequence offers a number of advantages. If a segment of a target sequence contains two closely spaced mutations, m1, and m2, and probes for analyzing that segment have an interrogation position at or near the middle, then no probe has an interrogation position aligned with one of the mutations without overlapping the other mutation (see first probe in FIG. 4B). Thus, the presence of a mutation would have to be detected by comparing the hybridization signal of a single-mismatched probe with a double-mismatched probe. By contrast, if the interrogation position is near the 3' end of the probes, probes can have their interrogation position aligned with m1 without overlapping m2 (second probe in FIG. 4B). Thus, the mutation can be detected by a comparison of a perfectly matched probe with single based mismatched probes. Similarly, if the interrogation position is near the 5' end of the probes, probes can have their interrogation position aligned with m2 without overlapping m1 (third probe in FIG. 4B).

Variation of the interrogation position also offers the advantage of reducing loss of signal due to self-annealing of certain probes. FIG. 4C shows a target sequence having a nucleotide X, which can be read either from the relative signals of the four probes having a central interrogation position (shown at the left of the figure) or from the four probes having the interrogation position near the three prime end (shown at the right of the figure). Only the probes having the central interrogation position are capable of self-annealing. Thus, a higher signal is obtained from the probes having the interrogation position near the terminus.

The probes are designed to be complementary to either strand of the reference sequence (e.g., coding or non-coding). Some chips contain separate groups of probes, one complementary to the coding strand, the other complementary to the noncoding strand. Independent analysis of coding and noncoding strands provides largely redundant information. However, the regions of ambiguity in reading the coding strand are not always the same as those in reading the noncoding strand. Thus, combination of the information from coding and noncoding strands increases the overall accuracy of sequencing.

Some chips contain additional probes or groups of probes designed to be complementary to a second reference sequence. The second reference sequence is often a subsequence of the first reference sequence bearing one or more commonly occurring mutations or interstrain variations. The second group of probes is designed by the same principles as described above except that the probes exhibit complementarity to the second reference sequence. The inclusion of a second group is particular useful for analyzing short subsequences of the primary reference sequence in which multiple mutations are expected to occur within a short distance commensurate with the length of the probes (i.e., two or more mutations within 9 to 21 bases). Of course, the same principle can be extended to provide chips containing groups of probes for any number of reference sequences. Alternatively, the chips may contain additional probe(s) that do not form part of a tiled array as noted above, but rather serves as probe(s) for a conventional reverse dot blot. For example, the presence of mutation can be detected from binding of a target sequence to a single oligomeric probe harboring the mutation. Preferably, an additional probe containing the equivalent region of the wildtype sequence is included as a control.

Although only a subset of probes is required to analyze a particular target sequence, it is quite possible that other probes superfluous to the contemplated analysis are also included on the chip. In the extreme case, the chip could can a complete set of all probes of a given length notwithstanding that only a small subset is required to analyze the particular reference sequence of interest. Although such a situation might appear wasteful of resources, a chip including a complete set of probes offers the advantage of including the appropriate subset of probes for analyzing any reference sequence. Such a chip also allows simultaneous analysis of a reference sequence from different subsets of probes (e.g., subsets having the interrogation site at different positions in the probe).

In its simplest terms, the analysis of a chip reveals whether the target sequence is the same or different from the reference sequence. If the two are the same, all probes in the first probe set show a stronger hybridization signal than corresponding probes from other probe sets. If the two are different, most probes from the first probe set still show a stronger hybridization signal than corresponding probes from the other probe sets, but some probes from the first probe set do not. Thus, when a probe from another probe sets light up more strongly than the corresponding probe from the first probe set, this provides a simple visual indication that the target sequence and reference sequence differ.

The chips also reveal the nature and position of differences between the target and reference sequence. The chips are read by comparing the intensities of labelled target bound to the probes in an array. Specifically, for each nucleotide of interest in the target sequence, a comparison is performed between probes having an interrogation position aligned with that position. These probes form a column (actual or conceptual) on the chip. For example, a column often contains one probe from each of A, C, G and T lanes. The nucleotide in the target sequence is identified as the complement of the nucleotide occupying the interrogation position in the probe showing the highest hybridization signal from a column. FIG. 6 shows the hybridization pattern of a chip hybridized to its reference sequence. The dark square in each column represents the probe from the column having the highest hybridization signal. The sequence can be read by following the pattern of dark squares from left to right across the chip. The first dark square is in the A lane indicating that the nucleotide occupying the interrogation position of the probe represented by this square is an A. The first nucleotide in the reference sequence is the complement of nucleotide occupying the interrogation position of this probe (i.e., a T). Similarly, the second dark square is in the T-lane, from which it can be deduced that the second nucleotide in the reference sequence is an A. Likewise the third dark square is in the T-lane, from which it can be deduced that the third nucleotide in the reference sequence is also an A, and so forth. By including probes in the first probe set (and by implication in the other probe sets) with interrogation positions corresponding to every nucleotide in a reference sequence, it is possible to read substantially every nucleotide in a target sequence, thereby revealing the complete or nearly complete sequence of the target.

Of the four probes in a column, only one can exhibit a perfect match to the target sequence whereas the others usually exhibit at least a one base pair mismatch. The probe exhibiting a perfect match usually produces a substantially greater hybridization signal than the other three probes in the column and is thereby easily identified. However, in some regions of the target sequence, the distinction between a perfect match and a one-base mismatch is less clear. Thus, a call ratio is established to define the ratio of signal from the best hybridizing probes to the second best hybridizing probe that must be exceeded for a particular target position to be read from the probes. A high call ratio ensures that few if any errors are made in calling target nucleotides, but can result in some nucleotides being scored as ambiguous, which could in fact be accurately read. A lower call ratio results in fewer ambiguous calls, but can result in more erroneous calls. It has been found that at a call ratio of 1.2 virtually all calls are accurate.

However, a small but significant number of bases (e.g., up to about 10%) may have to be scored as ambiguous.

Although small regions of the target sequence can sometimes be ambiguous, these regions usually occur at the same or similar segments in different target sequences. Thus, for precharacterized mutations, it is known in advance whether that mutation is likely to occur within a region of unambiguously determinable sequence.

An array of probes is most useful for analyzing the reference sequence from which the probes were designed and variants of that sequence exhibiting substantial sequence similarity with the reference sequence (e.g., several single-base mutants spaced over the reference sequence). When an array is used to analyze the exact reference sequence from which it was designed, one probe exhibits a perfect match to the reference sequence, and the other three probes in the same column exhibits single-base mismatches. Thus, discrimination between hybridization signals is usually high and accurate sequence is obtained. High accuracy is also obtained when an array is used for analyzing a target sequence comprising a variant of the reference sequence that has a single mutation relative to the reference sequence, or several widely spaced mutations relative to the reference sequence. At different mutant loci, one probe exhibits a perfect match to the target, and the other three probes occupying the same column exhibit single-base mismatches, the difference (with respect to analysis of the reference sequence) being the lane in which the perfect match occurs.

For target sequences showing a high degree of divergence from the reference strain or incorporating several closely spaced mutations from the reference strain, a single group of probes (i.e., designed with respect to a single reference sequence) will not always provide accurate sequence for the highly variant region of this sequence. At some particular columnar positions, it may be that no single probe exhibits perfect complementarity to the target and that any comparison must be based on different degrees of mismatch between the four probes. Such a comparison does not always allow the target nucleotide corresponding to that columnar position to be called. Deletions in target sequences can be detected by loss of signal from probes having interrogation positions encompassed by the deletion. However, signal may also be lost from probes having interrogation positions closely proximal to the deletion resulting in some regions of the target sequence that cannot be read. Target sequence bearing insertions will also exhibit short regions including and proximal to the insertion that usually cannot be read.

The presence of short regions of difficult-to-read target because of closely spaced mutations, insertions or deletions, does not prevent determination of the remaining sequence of the target as different regions of a target sequence are determined independently. Moreover, such ambiguities as might result from analysis of diverse variants with a single group of probes can be avoided by including multiple groups of probe sets on a chip. For example, one group of probes can be designed based on a full-length reference sequence, and the other groups on subsequences of the reference sequence incorporating frequently occurring mutations or strain variations.

A particular advantage of the present sequencing strategy over conventional sequencing methods is the capacity simultaneously to detect and quantify proportions of multiple target sequences. Such capacity is valuable, e.g., for diagnosis of patients who are heterozygous with respect to a gene or who are infected with a virus, such as HIV, which is usually present in several polymorphic forms. Such capacity is also useful in analyzing targets from biopsies of tumor cells and surrounding tissues. The presence of multiple target sequences is detected from the relative signals of the four probes at the array columns corresponding to the target nucleotides at which diversity occurs. The relative signals of the four probes for the mixture under test are compared with the corresponding signals from a homogeneous reference sequence. An increase in a signal from a probe that is mismatched with respect to the reference sequence, and a corresponding decrease in the signal from the probe which is matched with the reference sequence, signal the presence of a mutant strain in the mixture. The extent in shift in hybridization signals of the probes is related to the proportion of a target sequence in the mixture. Shifts in relative hybridization signals can be quantitatively related to proportions of reference and mutant sequence by prior calibration of the chip with seeded mixtures of the mutant and reference sequences. By this means, a chip can be used to detect variant or mutant strains constituting as little as 1, 5, 20, or 25% of a mixture of stains.

Similar principles allow the simultaneous analysis of multiple target sequences even when none is identical to the reference sequence. For example, with a mixture of two target sequences bearing first and second mutations, there would be a variation in the hybridization patterns of probes having interrogation positions corresponding to the first and second mutations relative to the hybridization pattern with the reference sequence. At each position, one of the probes having a mismatched interrogation position relative to the reference sequence would show an increase in hybridization signal, and the probe having a matched interrogation position relative to the reference sequence would show a decrease in hybridization signal. Analysis of the hybridization pattern of the mixture of mutant target sequences, preferably in comparison with the hybridization pattern of the reference sequence, indicates the presence of two mutant target sequences, the position and nature of the mutation in each strain, and the relative proportions of each strain.

In a variation of the above method, several target sequences target sequences are differentially labelled before being simultaneously applied to the array. For example, each different target sequence can be labelled with a fluorescent labels emitting at different wavelength. After applying a mixtures of target sequence to the arrays, the individual target sequences can be distinguished and independently analyzed by virtue of the differential labels. For example, the methods target sequences obtained from a patient at different stages of a disease can be differently labelled and analyzed simultaneously, facilitating identification of new mutations.

2. Omission of Probes

The basic strategy outlined above employs four probes to read each nucleotide of interest in a target sequence. One probe (from the first probe set) shows a perfect match to the reference sequence and the other three probes (from the second, third and fourth probe sets) exhibit a mismatch with the reference sequence and a perfect match with a target sequence bearing a mutation at the nucleotide of interest. The provision of three probes from the second, third and fourth probe sets allows detection of each of the three possible nucleotide substitutions of any nucleotide of interest. However, in some reference sequences or regions of reference sequences, it is known in advance that only certain mutations are likely to occur. Thus, for example, at one site it might be known that an A nucleotide in the reference sequence may exist as a T mutant in some target sequences but is unlikely to exist as a C or G mutant. Accordingly, for analysis of this region of the reference sequence, one might include only the first and second probe sets, the first probe set exhibiting perfect complementarity to the reference sequence, and the second probe set having an interrogation position occupied by an invariant A residue (for detecting the T mutant). In other situations, one might include the first, second and third probes sets (but not the fourth) for detection of a wildtype nucleotide in the reference sequence and two mutant variants thereof in target sequences. In some chips, probes that would detect silent mutations (i.e., not affecting amino acid sequence) are omitted.

Some chips effectively contain the second, third and optionally, the fourth probes sets described in the basic tiling strategy (i.e., the mismatched probe sets) but omit some or all of the probes from the first probe set (i.e., perfectly matched probes). Therefore, such chips comprise at least two probe sets, which will arbitrarily be referred to as probe sets A and B (to avoid confusion with the nomenclature used to describe the four probe sets in the basic tiling strategy). Probe set A has a plurality of probes. Each probe comprises a segment exactly complementary to a subsequence of a reference sequence except in at least one interrogation position. The interrogation position corresponds to a nucleotide in the reference sequence juxtaposed with the interrogation position when the reference sequence and probe are maximally aligned. Probe set B has a corresponding probe for each probe in the first probe set. The corresponding probe in probe set B is identical to a sequence comprising the corresponding probe from the first probe set or a subsequence thereof that includes the at least one (and usually only one) interrogation position except that the at least one interrogation position is occupied by a different nucleotide in each of the two corresponding probes from the probe sets A and B. An additional probe set C, if present, also comprises a corresponding probe for each probe in the probe set A except in the at least one interrogation position, which differs in the corresponding probes from probe sets A, B and C. The arrangement of probe sets A, B and C is shown in FIG. 3B. FIG. 3B is the same as FIG. 3A except that the first probe set has been omitted and the second, third and fourth probe sets in FIG. 3A have been relabelled as probe sets A, B and C in FIG. 3B.

Chips lacking perfectly matched probes are preferably analyzed by hybridization to both target and reference sequences. The hybridizations can be performed sequentially, or, if the target and reference are differentially labelled, concurrently. The hybridization data are then analyzed in two ways. First, considering only the hybridization signals of the probes to the target sequence, one compares the signals of corresponding probes for each position of interest in the target sequence. For a position of mismatch with the reference sequence, one of the probes having an interrogation position aligned with that position in the target sequence shows a substantially higher signal than other corresponding probes. The nucleotide occupying the position of mismatch in the target sequence is the complement of the nucleotide occupying the interrogation position of the corresponding probe showing the highest signal. For a position where target and reference sequence are the same, none of the corresponding probes having an interrogation position aligned with that position in the target sequence is matched, and corresponding probes generally show weak signals, which may vary somewhat from each other.

In a second level of analysis, the ratio of hybridization signals to the target and reference sequences is determined for each probe in the array. For most probes in the array the ratio of hybridization signals is about the same. For such a probe, it can be deduced that the interrogation position of the probe corresponds to a nucleotide that is the same in target and reference sequences. A few probes show a much higher ratio of target hybridization to reference hybridization than the majority of probes. For such a probe, it can be deduced that the interrogation position of the probe corresponds to a nucleotide that differs between target and reference sequences, and that in the target, this nucleotide is the complement of the nucleotide occupying the interrogation position of the probe. The second level of analysis serves as a control to confirm the identification of differences between target and reference sequence from the first level of analysis.

3. Wildtype Probe Lane

When the chips comprise four probe sets, as discussed supra, and the probe sets are laid down in four lanes, an A lane, a C-lane, a G lane and a T or U lane, the probe having a segment exhibiting perfect complementarity to a reference sequence varies between the four lanes from one column to another. This does not present any significant difficulty in computer analysis of the data from the chip. However, visual inspection of the hybridization pattern of the chip is sometimes facilitated by provision of an extra lane of probes, in which each probe has a segment exhibiting perfect complementarity to the reference sequence. See FIG. 4A. This extra lane of probes is called the wildtype lane and contains only probes from the first probe set. Each wildtype lane probe has a segment that is identical to a segment from one of the probes in the other four lanes (which lane depending on the column position). The wildtype lane hybridizes to a target sequence at all nucleotide positions except those in which deviations from the reference sequence occurs. The hybridization pattern of the wildtype lane thereby provides a simple visual indication of mutations.

4. Deletion, Insertion and Multiple-Mutation Probes

Some chips provide an additional probe set specifically designed for analyzing deletion mutations. The additional probe set comprises a probe corresponding to each probe in the first probe set as described above. However, a probe from the additional probe set differs from the corresponding probe in the first probe set in that the nucleotide occupying the interrogation position is deleted in the probe from the additional probe set. See FIG. 6. Optionally, the probe from the additional probe set bears an additional nucleotide at one of its termini relative to the corresponding probe from the first probe set (shown in brackets in FIG. 6). The probe from the additional probe set will hybridize more strongly than the corresponding probe from the first probe set to a target sequence having a single base deletion at the nucleotide corresponding to the interrogation position. Additional probe sets are provided in which not only the interrogation position, but also an adjacent nucleotide is deleted.

Similarly, other chips provide additional probe sets for analyzing insertions. For example, one additional probe set has a probe corresponding to each probe in the first probe set as described above. However, the probe in the additional probe set has an extra T nucleotide inserted adjacent to the interrogation position. See FIG. 6 (the extra T is shown in a square box). Optionally, the probe has one fewer nucleotide at one of its termini relative to the corresponding probe from the first probe set (shown in brackets). The probe from the additional probe set hybridizes more strongly than the corresponding probe from the first probe set to a target sequence having an A insertion to the left of nucleotide "n" the reference sequence in FIG. 6. Similar additional probe sets can be constructed having C, G or A nucleotides inserted adjacent to the interrogation position.

Usually, four such additional probe sets, one for each nucleotide, are used in combination. Comparison of the hybridization signal of the probes from the additional probe sets with the corresponding probe from the first probe set indicates whether the target sequence contains and insertion.

For example, if a probe from one of the additional probe sets shows a higher hybridization signal than a corresponding probe from the first probe set, it is deduced that the target sequence contains an insertion adjacent to the corresponding nucleotide (n) in the target sequence. The inserted base in the target is the complement of the inserted base in the probe from the additional probe set showing the highest hybridization signal. If the corresponding probe from the first probe set shows a higher hybridization signal than the corresponding probes from the additional probe sets, then the target sequence does not contain an insertion to the left of corresponding position (("n" in FIG. 6)) in the target sequence.

Other chips provide additional probes (multiple-mutation probes) for analyzing target sequences having multiple closely spaced mutations. A multiple-mutation probe is usually identical to a corresponding probe from the first set as described above, except in the base occupying the interrogation position, and except at one or more additional positions, corresponding to nucleotides in which substitution may occur in the reference sequence. The one or more additional positions in the multiple mutation probe are occupied by nucleotides complementary to the nucleotides occupying corresponding positions in the reference sequence when the possible substitutions have occurred.

5. Block Tiling

In block tiling, a perfectly matched (or wildtype) probe is compared with multiple sets of mismatched or mutant probes. The perfectly matched probe and the multiple sets of mismatched probes with which it is compared collectively form a group or block of probes on the chip. Each set comprises at least one, and usually, three mismatched probes. FIG. 7 shows a perfectly matched probe (CAATCGA) having three interrogation positions ($I_1$, $I_2$ and $I_3$). The perfectly matched probe is compared with three sets of probes (arbitrarily designated A, B and C), each having three mismatched probes. In set A, the three mismatched probes are identical to a sequence comprising the perfectly matched probe or a subsequence thereof including the interrogation positions, except at the first interrogation position. That is, the mismatched probes in the set A differ from the perfectly matched probe set at the first interrogation position. Thus, the relative hybridization signals of the perfectly matched probe and the mismatched probes in the set A indicates the identity of the nucleotide in a target sequence corresponding to the first interrogation position. This nucleotide is the complement of the nucleotide occupying the interrogation position of the probe showing the highest signal. Similarly, set B comprises three mismatched probes, that differ from the perfectly matched probe at the second interrogation position. The relative hybridization intensities of the perfectly matched probe and the three mismatched probes of set B reveal the identity of the nucleotide in the target sequence corresponding to the second interrogation position (i.e., n2 in FIG. 7). Similarly, the three mismatched probes in set C in FIG. 7 differ from the perfectly matched probe at the third interrogation position. Comparison of the hybridization intensities of the perfectly matched probe and the mismatched probes in the set C reveals the identity of the nucleotide in the target sequence corresponding to the third interrogation position (n3).

As noted above, a perfectly matched probe may have seven or more interrogation positions. If there are seven interrogation positions, there are seven sets of three mismatched probe, each set serving to identify the nucleotide corresponding to one of the seven interrogation positions. Similarly, if there are 20 interrogation positions in the perfectly matched probe, then 20 sets of three mismatched probes are employed. As in other tiling strategies, selected probes can be omitted if it is known in advance that only certain types of mutations are likely to arise.

Each block of probes allows short regions of a target sequence to be read. For example, for a block of probes having seven interrogation positions, seven nucleotides in the target sequence can be read. Of course, a chip can contain any number of blocks depending on how many nucleotides of the target are of interest. The hybridization signals for each block can be analyzed independently of any other block. The block tiling strategy can also be combined with other tiling strategies, with different parts of the same reference sequence being tiled by different strategies.

The block tiling strategy is a species of the basic tiling strategy discussed above, in which the probe from the first probe set has more than one interrogation position. The perfectly matched probe in the block tiling strategy is equivalent to a probe from the first probe set in the basic tiling strategy. The three mismatched probes in set A in block tiling are equivalent to probes from the second, third and fourth probe sets in the basic tiling strategy. The three mismatched probes in set B of block tiling are equivalent to probes from additional probe sets in basic tiling arbitrarily designated the fifth, sixth and seventh probe sets. The three mismatched probes in set C of blocking tiling are equivalent to probes from three further probe sets in basic tiling arbitrarily designated the eighth, ninth and tenth probe sets.

The block tiling strategy offers two advantages over a basic strategy in which each probe in the first set has a single interrogation position. One advantage is that the same sequence information can be obtained from fewer probes. A second advantage is that each of the probes constituting a block (i.e., a probe from the first probe set and a corresponding probe from each of the other probe sets) can have identical 3' and 5' sequences, with the variation confined to a central segment containing the interrogation positions. The identity of 3' sequence between different probes simplifies the strategy for solid phase synthesis of the probes on the chip and results in more uniform deposition of the different probes on the chip, thereby in turn increasing the uniformity of signal to noise ratio for different regions of the chip.

6. Multiplex Tiling

In the block tiling strategy discussed above, the identity of a nucleotide in a target or reference sequence is determined by comparison of hybridization patterns of one probe having a segment showing a perfect match with that of other probes (usually three other probes) showing a single base mismatch. In multiplex tiling, the identity of at least two nucleotides in a reference or target sequence is determined by comparison of hybridization signal intensities of four probes, two of which have a segment showing perfect complementarity or a single base mismatch to the reference sequence, and two of which have a segment showing perfect complementarity or a double-base mismatch to a segment. The four probes whose hybridization patterns are to be compared each have a segment that is exactly complementary to a reference sequence except at two interrogation positions, in which the segment may or may not be complementary to the reference sequence. The interrogation positions correspond to the nucleotides in a reference or target sequence which are determined by the comparison of intensities. The nucleotides occupying the interrogation positions in the four probes are selected according to the following rule. The first interrogation position is occupied by a different nucleotide in each of the four probes. The second interrogation position is also occupied by a different nucleotide in each of the four probes. In two of the four probes, designated the first and second probes, the segment is exactly complementary to the reference sequence except at not more than one of the two interrogation positions. In other words, one of the interrogation positions is occupied by a nucleotide that is complementary to the corresponding nucleotide from the reference sequence and the other interrogation position may or may not be so occupied. In the other two of the four probes, designated the third and fourth probes, the segment is exactly complementary to the reference sequence except that both interrogation positions are occupied by nucleotides which are noncomplementary to the respective corresponding nucleotides in the reference sequence.

There are number of ways of satisfying these conditions depending on whether the two nucleotides in the reference sequence corresponding to the two interrogation positions are the same or different. If these two nucleotides are different in the reference sequence (probability 3/4), the conditions are satisfied by each of the two interrogation positions being occupied by the same nucleotide in any given probe. For example, in the first probe, the two interrogation positions would both be A, in the second probe, both would be C, in the third probe, each would be G, and in the fourth probe each would be T or U. If the two nucleotides in the reference sequence corresponding to the two interrogation positions are different, the conditions noted above are satisfied by each of the interrogation positions in any one of the four probes being occupied by complementary nucleotides. For example, in the first probe, the interrogation positions could be occupied by A and T, in the second probe by C and G, in the third probe by G and C, and in the four probe, by T and A. See (FIG. 8).

When the four probes are hybridized to a target that is the same as the reference sequence or differs from the reference sequence at one (but not both) of the interrogation positions, two of the four probes show a double-mismatch with the target and two probes show a single mismatch. The identity of probes showing these different degrees of mismatch can be determined from the different hybridization signals. From the identity of the probes showing the different degrees of mismatch, the nucleotides occupying both of the interrogation positions in the target sequence can be deduced.

For ease of illustration, the multiplex strategy has been initially described for the situation where there are two nucleotides of interest in a reference sequence and only four probes in an array. Of course, the strategy can be extended to analyze any number of nucleotides in a target sequence by using additional probes. In one variation, each pair of interrogation positions is read from a unique group of four probes. In a block variation, different groups of four probes exhibit the same segment of complementarity with the reference sequence, but the interrogation positions move within a block. The block and standard multiplex tiling variants can of course be used in combination for different regions of a reference sequence. Either or both variants can also be used in combination with any of the other tiling strategies described.

7. Helper Mutations

Occasionally, small regions of a reference sequence give a low hybridization signal as a result of annealing of probes. The self-annealing reduces the amount of probe effectively available for hybridizing to the target. Although such regions of the target are generally small and the reduction of hybridization signal is usually not so substantial as to obscure the sequence of this region, this concern can be avoided by the use of probes incorporating helper mutations. A helper mutation refers to a position of mismatch in a probe other than at an interrogation position. The helper mutation(s) serve to break-up regions of internal complementarity within a probe and thereby prevent annealing. Usually, one or two helper mutations are quite sufficient for this purpose. The inclusion of helper mutations can be beneficial in any of the tiling strategies noted above. In general each probe having a particular interrogation position has the same helper mutation(s). Thus, such probes have a segment in common which shows perfect complementarity with a reference sequence, except that the segment contains at least one helper mutation (the same in each of the probes) and at least one interrogation position (different in all of the probes). For example, in the basic tiling strategy, a probe from the first probe set comprises a segment containing an interrogation position and showing perfect complementarity with a reference sequence except for one or two helper mutations. The corresponding probes from the second, third and fourth probe sets usually comprise the same segment (or sometimes a subsequence thereof including the helper mutation(s) and interrogation position), except that the base occupying the interrogation position varies in each probe. See FIG. 9.

Usually, the helper mutation tiling strategy is used in conjunction with one of the tiling strategies described above. The probes containing helper mutations are used to tile regions of a reference sequence otherwise giving low hybridization signal (e.g., because of self-complementarity), and the alternative tiling strategy is used to tile intervening regions.

8. Pooling Strategies

Pooling strategies also employ arrays of immobilized probes. Probes are immobilized in cells of an array, and the hybridization signal of each cell can be determined independently of any other cell. A particular cell may be occupied by pooled mixture of probes. Although the identity of each probe in the mixture is known, the individual probes in the pool are not separately addressable. Thus, the hybridization signal from a cell is the aggregate of that of the different probes occupying the cell. In general, a cell is scored as hybridizing to a target sequence if at least one probe occupying the cell comprises a segment exhibiting perfect complementarity to the target sequence.

A simple strategy to show the increased power of pooled strategies over a standard tiling is to create three cells each containing a pooled probe having a single pooled position, the pooled position being the same in each of the pooled probes. At the pooled position, there are two possible nucleotide, allowing the pooled probe to hybridize to two target sequences. In tiling terminology, the pooled position of each probe is an interrogation position. As will become apparent, comparison of the hybridization intensities of the pooled probes from the three cells reveals the identity of the nucleotide in the target sequence corresponding to the interrogation position (i.e., that is matched with the interrogation position when the target sequence and pooled probes are maximally aligned for complementarity).

The three cells are assigned probe pools that are perfectly complementary to the target except at the pooled position, which is occupied by a different pooled nucleotide in each probe as follows:

[AC]=M, [GT]=K, [AG]=R as substitutions in the probe
 IUPAC standard ambiguity notation)

```
                     X - interrogation position

Target:   TAACCACTCACGGGAGCA
```

```
                  -continued
Pool 1     ATTGGMGAGTGCCC
(SEQ. ID.  =ATTGGaGAGTGCCC    (complement to mutant 't')
Nos.
2-4):      +ATTGGcGAGTGCCC    (complement to mutant 'g')

Pool 2     ATTGGKGAGTGCCC
(SEQ. ID.  =ATTGGgGAGTGCCC    (complement to mutant 'C')
Nos.
5-7):      +ATTGGtGAGTGCCC    (complement to wild type 'a')

Pool 3     ATTGGRGAGTGCCC
(SEQ. ID.  =ATTGGaGAGTGCCC    (complement to mutant 't')
No.
8):        +ATTGGgGAGTGCCC    (complement to mutant 'c')
```

With 3 pooled probes, all 4 possible single base pair states (wild and 3 mutants) are detected. A pool hybridizes with a target if some probe contained within that pool is complementary to that target.

|  |  | Hybridization? | | |
|---|---|---|---|---|
| Pool: |  | 1 | 2 | 3 |
| Target: | TAACCACTCACGGGAGCA | n | y | n |
| Mutant (SEQ. ID. No. 9): | TAACCcCTCACGGGAGCA | n | y | y |
| Mutant (SEQ. ID. No. 10): | TAACCgCTCACGGGAGCA | y | n | n |
| Mutant (SEQ. ID. No. 11): | TAACCtCTCACGGGAGCA | y | n | y |

A cell containing a pair (or more) of oligonucleotides lights up when a target complementary to any of the oligonucleotide in the cell is present. Using the simple strategy, each of the four possible targets (wild and three mutants) yields a unique hybridization pattern among the three cells.

Since a different pattern of hybridizing pools is obtained for each possible nucleotide in the target sequence corresponding to the pooled interrogation position in the probes, the identity of the nucleotide can be determined from the hybridization pattern of the pools. Whereas, a standard tiling requires four cells to detect and identify the possible single-base substitutions at one location, this simple pooled strategy only requires three cells.

A more efficient pooling strategy for sequence analysis is the 'Trellis' strategy. In this strategy, each pooled probe has a segment of perfect complementarity to a reference sequence except at three pooled positions. One pooled position is an N pool (IUPAC standard ambiguity code). The three pooled positions may or may not be contiguous in a probe. The other two pooled positions are selected from the group of three pools consisting of (1) M or K, (2) R or Y and (3) W or S, where the single letters are IUPAC standard ambiguity codes. The sequence of a pooled probe is thus, of the form XXXN [((M/K) or (R/Y) or (W/S)] [(M/K) or (R/Y) or (W/S)] XXXXX, where XXX represents bases complementary to the reference sequence. The three pooled positions may be in any order, and may be contiguous or separated by intervening nucleotides. For, the two positions occupied by [(M/K) or (R/Y) or (W/S)], two choices must be made. First, one must select one of the following three pairs of pooled nucleotides (1) M/K, (2) R/Y and (3) W/S. The one of three pooled nucleotides selected may be the same or different at the two pooled positions. Second, supposing, for example, one selects M/K at one position, one must then choose between M or K. This choice should result in selection of a pooled nucleotide comprising a nucleotide that complements the corresponding nucleotide in a reference sequence, when the probe and reference sequence are maximally aligned. The same principle governs the selection between R and Y, and between W and S. A trellis pool probe has one pooled position with four possibilities, and two pooled positions, each with two possibilities. Thus, a trellis pool probe comprises a mixture of 16 (4×2×2) probes. Since each pooled position includes one nucleotide that complements the corresponding nucleotide from the reference sequence, one of these 16 probes has a segment that is the exact complement of the reference sequence. A target sequence that is the same as the reference sequence (i.e., a wildtype target) gives a hybridization signal to each probe cell. Here, as in other tiling methods, the segment of complementarity should be sufficiently long to permit specific hybridization of a pooled probe to a reference sequence be detected relative to a variant of that reference sequence. Typically, the segment of complementarity is about 9-21 nucleotides.

A target sequence is analyzed by comparing hybridization intensities at three pooled probes, each having the structure described above. The segments complementary to the reference sequence present in the three pooled probes show some overlap. Sometimes the segments are identical (other than at the interrogation positions). However, this need not be the case. For example, the segments can tile across a reference sequence in increments of one nucleotide (i.e., one pooled probe differs from the next by the acquisition of one nucleotide at the 5' end and loss of a nucleotide at the 3' end). The three interrogation positions may or may not occur at the same relative positions within each pooled probe (i.e., spacing from a probe terminus). All that is required is that one of the three interrogation positions from each of the three pooled probes aligns with the same nucleotide in the reference sequence, and that this interrogation position is occupied by a different pooled nucleotide in each of the three probes. In one of the three probes, the interrogation position is occupied by an N. In the other two pooled probes the interrogation position is occupied by one of (M/K) or (R/Y) or (W/S).

In the simplest form of the trellis strategy, three pooled probes are used to analyze a single nucleotide in the reference sequence. Much greater economy of probes is achieved when more pooled probes are included in an array. For example, consider an array of five pooled probes each having the general structure outlined above. Three of these pooled probes have an interrogation position that aligns with the same nucleotide in the reference sequence and are used to read that nucleotide. A different combination of three probes have an interrogation position that aligns with a different nucleotide in the reference sequence. Comparison of these three probe intensities allows analysis of this second nucleotide. Still another combination of three pooled probes from the set of five have an interrogation position that aligns with a third nucleotide in the reference sequence and these probes are used to analyze that nucleotide. Thus, three nucleotides in the reference sequence are fully analyzed from only five pooled probes. By comparison, the basic tiling strategy would require 12 probes for a similar analysis.

As an example, a pooled probe for analysis of a target sequence by the trellis strategy is shown below:

```
Target (SEQ. ID. No. 12):   ATTAACCACTCACGGGAGCTCT

Pool (SEQ. ID. No. 13):             TGGTGNKYGCCCT
```

The pooled probe actually comprises 16 individual probes:
The pooled probe actually comprises 16 individual probes (SEQ. ID. Nos. 14-29):

```
                 TGGTGAGcGCCCT
                +TGGTGcGcGCCCT
                +TGGTGgGcGCCCT
                +TGGTGtGcGCCCT
                +TGGTGAtcGCCCT
                +TGGTGctcGCCCT
                +TGGTGgtcGCCCT
                +TGGTGttcGCCCT
                +TGGTGAGTGCCCT
                +TGGTGcGTGCCCT
                +TGGTGgGTGCCCT
                +TGGTGtGTGCCCT
                +TGGTGAtTGCCCT
                +TGGTGctTGCCCT
                +TGGTGgtTGCCCT
                +TGGTGttTGCCCT
```

The trellis strategy employs an array of probes having at least three cells, each of which is occupied by a pooled probe as described above.

Consider the use of three such pooled probes for analyzing a target sequence, of which one position may contain any single base substitution to the reference sequence (i.e, there are four possible target sequences to be distinguished). Three cells are occupied by pooled probes having a pooled interrogation position corresponding to the position of possible substitution in the target sequence, one cell with an 'N', one cell with one of 'M' or 'K', and one cell with 'R' or 'Y'. An interrogation position corresponds to a nucleotide in the target sequence if it aligns adjacent with that nucleotide when the probe and target sequence are aligned to maximize complementarity. Note that although each of the pooled probes has two other pooled positions, these positions are not relevant for the present illustration. The positions are only relevant when more than one position in the target sequence is to be read, a circumstance that will be considered later. For present purposes, the cell with the 'N' in the interrogation position lights up for the wildtype sequence and any of the three single base substitutions of the target sequence. The cell with M/K in the interrogation position lights up for the wild-type sequence and one of the single-base substitutions. The cell with R/Y in the interrogation position lights up for the wildtype sequence and a second of the single-base substitutions. Thus, the four possible target sequences hybridize to the three pools of probes in four distinct patterns, and the four possible target sequences can be distinguished.

To illustrate further, consider four possible target sequences (differing at a single position) and a pooled probe having three pooled positions, N, K and Y with the Y position as the interrogation position (i.e., aligned with the variable position in the target sequence):

```
                      Target

Wild:           ATTAACCACTCACGGGAGCTCT          (w)

Mutants         ATTAACCACTCcCGGGAGCTCT          (c)
(SEQ. ID.
No. 30):

Mutants         ATTAACCACTCgCGGGAGCTCT          (g)
(SEQ. ID.
No. 31):

Mutants         ATTAACCACTCtCGGGAGCTCT          (t)
(SEQ. ID.
No. 32):

TGGTGNKYGCCCT         (pooled probe).
```

The sixteen individual component probes of the pooled probe hybridize to the four possible target sequences as follows:

|               | TARGET |   |   |   |
|---------------|---|---|---|---|
|               | w | c | g | t |
| TGGTGAGcGCCCT | n | n | y | n |
| TGGTGcGcGCCCT | n | n | n | n |
| TGGTGgGcGCCCT | n | n | n | n |
| TGGTGtGcGCCCT | n | n | n | n |
| TGGTGAtcGCCCT | n | n | n | n |
| TGGTGctcGCCCT | n | n | n | n |
| TGGTGgtcGCCCT | n | n | n | n |
| TGGTGttcGCCCT | n | n | n | n |
| TGGTGAGTGCCCT | y | n | n | n |
| TGGTGcGTGCCCT | n | n | n | n |
| TGGTGgGTGCCCT | n | n | n | n |
| TGGTGtGTGCCCT | n | n | n | n |
| TGGTGAtTGCCCT | n | n | n | n |
| TGGTGctTGCCCT | n | n | n | n |
| TGGTGgtTGCCCT | n | n | n | n |
| TGGTGttTGCCCT | n | n | n | n |

The pooled probe hybridizes according to the aggregate of its components:

| Pool: | TGGTGNKYGCCCT | y | n | y | n |
|---|---|---|---|---|---|

Thus, as stated above, it can be seen that a pooled probe having a y at the interrogation position hybridizes to the wildtype target and one of the mutants. Similar tables can be drawn to illustrate the hybridization patterns of probe pools having other pooled nucleotides at the interrogation position.

The above strategy of using pooled probes to analyze a single base in a target sequence can readily be extended to analyze any number of bases. At this point, the purpose of including three pooled positions within each probe will become apparent. In the example that follows, ten pools of probes (SEQ. ID. Nos. 33-41), each containing three pooled probe positions, can be used to analyze a each of a contiguous sequence of eight nucleotides in a target sequence.

```
           ATTAACCACTCACGGGAGCTCT  Reference sequence
                   --------        Readable nucleotides
Pools:
4       TAATTNKYGAGTG  - (SEQ. ID. No. 33)
5        AATTGNKRAGTGC - (SEQ. ID. No. 34)
6         ATTGGNKRGTGCC - (SEQ. ID. No. 35)
7          TTGGTNMRTGCCC - (SEQ. ID. No. 36)
8           TGGTNGKYGCCCT
9            GGTGANKRCCCTC - (SEQ. ID. No. 37)
10            GTGAGNKYCCTCG - (SEQ. ID. No. 38)
11             TGAGTNMYCTCGA - (SEQ. ID. No. 39)
12              GAGTGNMYTCGAG - (SEQ. ID. No. 40)
13               AGTGCNMYCGAGA - (SEQ. ID. No. 41)
```

In this example, the different pooled probes tile across the reference sequence, each pooled probe differing from the next by increments of one nucleotide. For each of the readable nucleotides in the reference sequence, there are three probe pools having a pooled interrogation position aligned with the readable nucleotide. For example, the 12th nucleotide from the left in the reference sequence is aligned with pooled interrogation positions in pooled probes 8, 9, and 10. Comparison of the hybridization intensities of these pooled probes reveals the identity of the nucleotide occupying position 12 in a target sequence.

|   |   | Pools |   |   |
|---|---|---|---|---|
|   | Targets | 8 | 9 | 10 |
| Wild: | ATTAACCACTCACGGGAGCTCT | Y | Y | Y |
| Mutants: | ATTAACCACTCCCGGGAGCTCT | N | Y | Y |
| Mutants: | ATTAACCACTCgCGGGAGCTCT | Y | N | Y |
| Mutants: | ATTAACCACTCtCGGGAGCTCT | N | N | Y |

EXAMPLE INTENSITIES

|   |   |
|---|---|
| = lit cell | Wild |
| = blank cell | 'C' |
|   | 'G' |
|   | 'T' |
|   | None |

Thus, for example, if pools 8, 9 and 10 all light up, one knows the target sequence is wildtype, If pools, 9 and 10 light up, the target sequence has a C mutant at position 12. If pools 8 and 10 light up, the target sequence has a G mutant at position 12. If only pool 10 lights up, the target sequence has a t mutant at position 12.

The identity of other nucleotides in the target sequence is determined by a comparison of other sets of three pooled probes. For example, the identity of the 13th nucleotide in the target sequence is determined by comparing the hybridization patterns of the probe pools designated 9, 10 and 11. Similarly, the identity of the 14th nucleotide in the target sequence is determined by comparing the hybridization patterns of the probe pools designated 10, 11, and 12.

In the above example, successive probes tile across the reference sequence in increments of one nucleotide, and each probe has three interrogation positions occupying the same positions in each probe relative to the terminus of the probe (i.e., the 7, 8 and 9th positions relative to the 3' terminus). However, the trellis strategy does not require that probes tile in increments of one or that the interrogation position positions occur in the same position in each probe. In a variant of trellis tiling referred to as "loop" tiling, a nucleotide of interest in a target sequence is read by comparison of pooled probes, which each have a pooled interrogation position corresponding to the nucleotide of interest, but in which the spacing of the interrogation position in the probe differs from probe to probe. Analogously to the block tiling approach, this allows several nucleotides to be read from a target sequence from a collection of probes that are identical except at the interrogation position. The identity in sequence of probes, particularly at their 3' termini, simplifies synthesis of the array and result in more uniform probe density per cell.

To illustrate the loop strategy, consider reference sequence of which the 4, 5, 6, 7 and 8th nucleotides (from the 3' termini are to be read. All of the four possible nucleotides at each of these positions can be read from comparison of hybridization intensities of five pooled probes (SEQ. ID. Nos. 42-46). Note that the pooled positions in the probes are different (for example in probe 55, the pooled positions are 4, 5 and 6 and in probe 56, 5, 6 and 7).

```
        TAACCACTCACGGGAGCA Reference sequence
55      ATTNKYGAGTGCC - (SEQ. ID. No. 42)
56      ATTGNKRAGTGCC - (SEQ. ID. No. 43)
57      ATTGGNKRGTGCC - (SEQ. ID. No. 44)
58      ATTRGTNMGTGCC - (SEQ. ID. No. 45)
59      ATTKRTGNGTGCC - (SEQ. ID. No. 46)
```

Each position of interest in the reference sequence is read by comparing hybridization intensities for the three probe pools that have an interrogation position aligned with the nucleotide of interest in the reference sequence. For example, to read the fourth nucleotide in the reference sequence, probes 55, 58 and 59 provide pools at the fourth position. Similarly, to read the fifth nucleotide in the reference sequence, probes 55, 56 and 59 provide pools at the fifth position. As in the previous trellis strategy, one of the three probes being compared has an N at the pooled position and the other two have M or K, and (2) R or Y and (3) W or S.

The hybridization pattern of the five pooled probes to target sequences representing each possible nucleotide substitution at five positions in the reference sequence is shown below. Each possible substitution results in a unique hybridization pattern at three pooled probes, and the identity of the nucleotide at that position can be deduced from the hybridization pattern.

|  |  | Pools |  |  |  |  |
|---|---|---|---|---|---|---|
|  | Targets | 55 | 56 | 57 | 58 | 59 |
| Wild: | TAACCACTCACGGGAGCA | Y | Y | Y | Y | Y |
| Mutant (SEQ. ID. No. 47): | TAAgCACTCACGGGAGCA | Y | N | N | N | N |
| Mutant (SEQ. ID. No. 48): | TAAtCACTCACGGGAGCA | Y | N | N | Y | N |
| Mutant (SEQ. ID. No. 49): | TAAaCACTCACGGGAGCA | Y | N | N | N | Y |
| Mutant (SEQ. ID. No. 50): | TAACgACTCACGGGAGCA | N | Y | N | N | N |
| Mutant (SEQ. ID. No. 51): | TAACtACTCACGGGAGCA | N | Y | N | N | Y |
| Mutant (SEQ. ID. No. 52): | TAACaACTCACGGGAGCA | Y | Y | N | N | N |
| Mutant: | TAACCcCTCACGGGAGCA | N | Y | Y | N | N |
| Mutant: | TAACCgCTCACGGGAGCA | Y | N | Y | N | N |
| Mutant: | TAACCtCTCACGGGAGCA | N | N | Y | N | N |
| Mutant (SEQ. ID. No. 53): | TAACCAgTCACGGGAGCA | N | N | N | Y | N |
| Mutant (SEQ. ID. No. 54): | TAACCAtTCACCGGAGCA | N | Y | N | Y | N |
| Mutant (SEQ. ID. No. 55): | TAACCAaTCACGGGAGCA | N | N | Y | Y | N |
| Mutant (SEQ. ID. No. 56): | TAACCACaCACGGGAGCA | N | N | N | N | Y |
| Mutant (SEQ. ID. No. 57): | TAACCACcCACGGGAGCA | N | N | Y | N | Y |
| Mutant (SEQ. ID. No. 58): | TAACCACgCACGGGAGCA | N | N | N | Y | Y |

Many variations on the loop and trellis tilings can be created. All that is required is that each position in sequence must have a probe with a 'N', a probe containing one of R/Y, M/K or W/S, and a probe containing a different pool from that set, complementary to the wild type target at that position, and at least one probe with no pool at all at that position. This combination allows all mutations at that position to be uniquely detected and identified.

A further class of strategies involving pooled probes are termed coding strategies. These strategies assign code words from some set of numbers to variants of a reference sequence. Any number of variants can be coded. The variants can include multiple closely spaced substitutions, deletions or insertions. The designation letters or other symbols assigned to each variant may be any arbitrary set of numbers, in any order. For example, a binary code is often used, but codes to other bases are entirely feasible. The numbers are often assigned such that each variant has a designation having at least one digit and at least one nonzero value for that digit. For example, in a binary system, a variant assigned the number 101, has a designation of three digits, with one possible nonzero value for each digit.

The designation of the variants are coded into an array of pooled probes comprising a pooled probe for each nonzero value of each digit in the numbers assigned to the variants. For example, if the variants are assigned successive number in a numbering system of base m, and the highest number assigned to a variant has n digits, the array would have about n×(m−1) pooled probes. In general, $\log_m (3N+1)$ probes are required to analyze all variants of N locations in a reference sequence, each having three possible mutant substitutions. For example, 10 base pairs of sequence may be analyzed with only 5 pooled probes using a binary coding system. Each pooled probe has a segment exactly complementary to the reference sequence except that certain positions are pooled. The segment should be sufficiently long to allow specific hybridization of the pooled probe to the reference sequence relative to a mutated form of the reference sequence. As in other tiling strategies, segments lengths of 9-21 nucleotides are typical. Often the probe has no nucleotides other than the 9-21 nucleotide segment. The pooled positions comprise nucleotides that allow the pooled probe to hybridize to every variant assigned a particular nonzero value in a particular digit. Usually, the pooled positions further comprises a nucleotide that allows the pooled probe to hybridize to the reference sequence. Thus, a wildtype target (or reference sequence) is immediately recognizable from all the pooled probes being lit.

When a target is hybridized to the pools, only those pools comprising a component probe having a segment that is exactly complementary to the target light up. The identity of the target is then decoded from the pattern of hybridizing pools. Each pool that lights up is correlated with a particular value in a particular digit. Thus, the aggregate hybridization patterns of each lighting pool reveal the value of each digit in the code defining the identity of the target hybridized to the array.

As an example, consider a reference sequence having four positions, each of which can be occupied by three possible mutations. Thus, in total there are 4×3 possible variant forms of the reference sequence. Each variant is assigned a binary number 0001-1100 and the wildtype reference sequence is assigned the binary number 1111.

| Positions | X | X | X | X - 4 |
|---|---|---|---|---|
| Target: TAAC CACGGGAGCA (SEQ. ID. No. 59) | C = 1111<br>G = 0001<br>T = 0101<br>A = 1001 | A = 1111<br>C = 0010<br>G = 0110<br>T = 1010 | C = 1111<br>G = 0011<br>T = 0111<br>A = 1011 | T = 1111<br>A = 0100<br>C = 1000<br>G = 1100 |

A first pooled probe is designed by including probes that complement exactly each variant having a 1 in the first digit.

```
target  (1111): TAAC C       A    C    T CACGGGAGCA
Mutant  (0001): TAAC    g    A    C    T CACGGGAGCA
Mutant  (0101): TAAC       t A    C    T CACGGGAGCA
Mutant  (1001): TAAC         a A  C    T CACGGGAGCA
Mutant  (0011): TAAC C       A    g    T CACGGGAGCA
Mutant  (0111): TAAC C       A       t T CACGGGAGCA
Mutant  (1101): TAAC C       A         a T CACGGGAGCA
```

```
                      -continued
First pooled probe
           =  ATTG [GCAT]   T [GCAT]   A GTGCCC
           =  ATTG N        T N        A GTGCCC
                                         (SEQ. ID.
                                         No. 60)
```

Second, third and fourth pooled probes are then designed respectively including component probes that hybridize to each variant having a 1 in the second, third and fourth digit.

```
                         XXXX - 4 positions examined

Target:          TAACCACTCACGGGAGCA

Pool 1(1):       ATTGnTnAGTGCCC      =     16 probes           (4 x 1 x 4 x 1)

Pool 2(2)        ATTGGnnAGTGCCC      =     16 probes           (1 x 4 x 4 x 1)
(SEQ. ID.
No. 61):

Pool 3(4         ATTGyrydGTGCCC      =     24 probes           (2 x 2 x 2 x 3)
(SEQ. ID.
No. 62):

Pool 4(8)        ATTGmwmbGTGCCC      =     24 probes           (2 x 2 x 2 x 3)
(SEQ. ID.
No. 63):
```

The pooled probes hybridize to variant targets as follows:

Hybridization pattern:

```
                                   Pools
             Targets         1   2   3   4
```

```
Wild(1111)        TAACCACTCACGGGAGCA   Y  Y  Y  Y
Mutant(0001):     TAACgACTCACGGGAGCA   Y  N  N  N
Mutant(0101):     TAACtACTCACGGGAGCA   Y  N  Y  N
Mutant(1001):     TAACaACTCACGGGAGCA   Y  N  N  Y Mutant(0010):     TAACCcCTCACGGGAGCA   N  Y  N  N
Mutant(0110):     TAACCgCTCACGGGAGCA   N  Y  Y  N
Mutant(1010):     TAACCtCTCACGGGAGCA   N  Y  N  Y
Mutant(0011):     TAACCAgTCACGGGAGCA   Y  Y  N  N
Mutant(0111):     TAACCAtTCACGGGAGCA   Y  Y  Y  N
Mutant(1101):     TAACCAaTCACGGGAGCA   Y  N  Y  Y Mutant(0100):     TAACCACaCACGGGAGCA   N  N  Y  N
Mutant(1000):     TAACCACcCACGGGAGCA   N  N  N  Y
Mutant(1100):     TAACCACgCACGGGAGCA   N  N  Y  Y
```

The identity of a variant (i.e., mutant) target is read directly from the hybridization pattern of the pooled probes. For example the mutant assigned the number 0001 gives a hybridization pattern of NNNY with respect to probes 4, 3, 2 and 1 respectively.

In the above example, variants are assigned successive numbers in a numbering system. In other embodiments, sets of numbers can be chosen for their properties. If the codewords are chosen from an error-control code, the properties of that code carry over to sequence analysis. An error code is a numbering system in which some designations are assigned to variants and other designations serve to indicate errors that may have occurred in the hybridization process. For example, if all codewords have an odd number of nonzero digits ('binary coding+error detection'), any single error in hybridization will be detected by having an even number of pools lit.

```
Wild
Target           TAACCACTCACGGGAGCA
(SEQ. ID.
No. 1):

Pool 1(1):       ATTGnAnAGTGCCC =     16 Probes  (4 x 1 x 4 x 1)

Pool 2(2):       ATTGGnnAGTGCCC =     16 Probes  (1 x 4 x 4 x 1)

Pool 3(4):       ATTGyrhGTGCCC  =     24 Probes  (2 x 2 x 2 x 3)

Pool 4(8):       ATTGkwkvGTGCCC =     24 Probes  (2 x 2 x 2 x 3)
```

A fifth probe can be added to make the number of pools that hybridize to any single mutation odd.

Pool 5(c): ATTGdhsmGTGCCC=36 probes (2×2×3×3)

Hybridization of pooled probes to targets

```
                                                        Pool
                 Target               1  2  3  4  5

Target (11111):  TAACCACTCACGGGAGCA   Y  Y  Y  Y  Y
Mutant (00001):  TAACgACTCACGGGAGCA   Y  N  N  N  N
Mutant (10101):  TAACtACTCACGGGAGCA   Y  N  N  N  N
Mutant (11001):  TAACaACTCACGGGAGCA   Y  N  N  Y  Y Mutant (00010):  TAACCcCTCACGGGAGCA   N  Y  N  N  N
Mutant (10110):  TAACCgCTCACGGGAGCA   N  Y  Y  N  Y
Mutant (11010):  TAACCtCTCACGGGAGCA   N  Y  N  Y  Y Mutant (10011):  TAACCAgTCACGGGAGCA   Y  Y  N  N  Y
Mutant (00111):  TAACAtTCACGGGAGCA    Y  Y  Y  N  N
```

```
Mutant (01101):      TAACCAaTCACGGGAGCA  Y  N  Y  Y  N

Mutant (00100):      TAACCACaCACGGGAGCA  N  N  Y  N  N
Mutant (01000):      TAACCAcCCACGGGAGCA  N  N  N  Y  N
Mutant (11100):      TAACCACgCACGGGAGCA  N  N  Y  Y  Y
```

9. Bridging Strategy

Probes that contain partial matches to two separate (i.e., non contiguous) subsequences of a target sequence sometimes hybridize strongly to the target sequence. In certain instances, such probes have generated stronger signals than probes of the same length which are perfect matches to the target sequence. It is believed (but not necessary to the invention) that this observation results from interactions of a single target sequence with two or more probes simultaneously. This invention exploits this observation to provide arrays of probes having at least first and second segments, which are respectively complementary to first and second subsequences of a reference sequence. Optionally, the probes may have a third or more complementary segments. These probes can be employed in any of the strategies noted above. The two segments of such a probe can be complementary to disjoint subsequences of the reference sequences or contiguous subsequences. If the latter, the two segments in the probe are inverted relative to the order of the complement of the reference sequence. The two subsequences of the reference sequence each typically comprises about 3 to 30 contiguous nucleotides. The subsequences of the reference sequence are sometimes separated by 0, 1, 2 or 3 bases. Often the sequences, are adjacent and nonoverlapping.

For example, a wildtype probe is created by complementing two sections of a reference sequence (indicated by subscript and superscript) and reversing their order. The interrogation position is designated (*) and is apparent from comparison of the structure of the wildtype probe with the three mismatched probes. The corresponding nucleotide in the reference sequence is the "a" in the superscripted segment.

```
Reference           5' T_GGCTA^CGAGG AATCATCTGTTA
(SEQ. ID. No. 65):

*
Probes              3' GCTCC CCGAT
(SEQ. ID. Nos.         (Probe from first probe set)
66-69):             3' GCACC CCGAT
                    3' GCCCC CCGAT
                    3' GCGCC CCGAT The expected hybridizations are:

Match:
                    GCTCCCCGAT
                ... TGGCTACGAGGAATCATCTGTTA
                         GCTCCCCGAT Mismatch:
                    GCTCCCCGAT
                ... TGGCTACGAGGAATCATCTGTTA
                         GCGCCCCGAT
```

Bridge tilings are specified using a notation which gives the length of the two constituent segments and the relative position of the interrogation position. The designation n/m indicates a segment complementary to a region of the reference sequence which extends for n bases and is located such that the interrogation position is in the mth base from the 5' end. If m is larger than n, this indicates that the entire segment is to the 5' side of the interrogation position. If m is negative, it indicates that the interrogation position is the absolute value of m bases 5' of the first base of the segment (m cannot be zero). Probes comprising multiple segments, such as n/m+a/b+. . . have a first segment at the 3' end of the probe and additional segments added 5' with respect to the first segment. For example, a 4/8 tiling consists of (from the 3' end of the probe) a 4 base complementary segment, starting 7 bases 5' of the interrogation position, followed by a 6 base region in which the interrogation position is located at the third base. Between these two segments, one base from the reference sequence is omitted. By this notation, the set shown above is a 5/3+5/8 tiling. Many different tilings are possible with this method, since the lengths of both segments can be varied, as well as their relative position (they may be in either order and there may be a gap between them) and their location relative to the interrogation position.

As an example, a 16 mer oligo target was hybridized to a chip containing all $4^{10}$ probes of length 10. The chip includes short tilings of both standard and bridging types. The data from a standard 10/5 tiling was compared to data from a 5/3+5/8 bridge tiling (see Table 1). Probe intensities (mean count/pixel) are displayed along with discrimination ratios (correct probe intensity/highest incorrect probe intensity). Missing intensity values are less than 50 counts. Note that for each base displayed the bridge tiling has a higher discrimination value.

TABLE 1

Comparison of Standard and Bridge Tilings

| TILING | PROBE BASE: | CORRECT PROBE BASE | | | |
|---|---|---|---|---|---|
| | | C | A | C | C |
| STANDARD | A | 92 | 496 | 294 | 299 |
| (10/5) | C | 536 | 148 | 532 | 534 |
| | G | 69 | 167 | 72 | 52 |
| | T | 146 | 95 | 212 | 126 |
| DISCRIMINATION: | | 3.7 | 3.0 | 1.8 | 1.8 |
| BRIDGING | A | — | 404 | — | 156 |
| 5/3 + 5/8 | C | 276 | — | 345 | 379 |
| | G | — | 80 | — | — |
| | T | — | — | — | 58 |
| DISCRIMINATION: | | >5.5 | 5.1 | 2.4 | 1.26 |

The bridging strategy offers the following advantages:

(1) Higher discrimination between matched and mismatched probes, (2) The possibility of using longer probes in a bridging tiling, thereby increasing the specificity of the hybridization, without sacrificing discrimination, (3) The use of probes in which an interrogation position is located very off-center relative to the regions of target complementarity. This may be of particular advantage when, for example, when a probe centered about one region of the target gives low hybridization signal. The low signal is overcome by using a probe centered about an adjoining region giving a higher hybridization signal.

(4) Disruption of secondary structure that might result in annealing of certain probes (see previous discussion of helper mutations).

10. Deletion Tiling

Deletion tiling is related to both the bridging and helper mutant strategies described above. In the deletion strategy, comparisons are performed between probes sharing a common deletion but differing from each other at an interrogation position located outside the deletion. For example, a first probe comprises first and second segments, each exactly complementary to respective first and second subsequences of a reference sequence, wherein the first and second subsequences of the reference sequence are separated by a short distance (e.g., 1 or 2 nucleotides). The order of the first and second segments in the probe is usually the same as that of the complement to the first and second subsequences in the reference sequence. The interrogation position is usually separated from The comparison is performed with three other probes, which are identical to the first probe except at an interrogation position, which is different in each probe.

Reference (SEQ. ID. No. 70): . . . AGTACCAGATCTCT AA . . .

Probe set (SEQ. ID. No. 71): CATGGNC AGAGA (N=interrogation position).

Such tilings sometimes offer superior discrimination in hybridization intensities between the probe having an interrogation position complementary to the target and other probes. Thermodynamically, the difference between the hybridizations to matched and mismatched targets for the probe set shown above is the difference between a single-base bulge, and a large asymmetric loop (e.g., two bases of target, one of probe). This often results in a larger difference in stability than the comparison of a perfectly matched probe with a probe showing a single base mismatch in the basic tiling strategy.

The superior discrimination offered by deletion tiling is illustrated by Table 2, which compares hybridization data from a standard 10/5 tiling with a (4/8+6/3) deletion tiling of the reference sequence. (The numerators indicate the length of the segments and the denominators, the spacing of the deletion from the far termini of the segments.) Probe intensities (mean count/pixel) are displayed along with discrimination ratios (correct probe intensity/highest incorrect probe intensity). Note that for each base displayed the deletion tiling has a higher discrimination value than either standard tiling shown.

TABLE 2

Comparison of Standard and Deletion Tilings

| TILING | PROBE BASE: | CORRECT PROBE BASE | | | |
|---|---|---|---|---|---|
| | | C | A | C | C |
| STANDARD | A | 92 | 496 | 294 | 299 |
| (10/5) | C | 536 | 148 | 532 | 534 |
| | G | 69 | 167 | 72 | 52 |
| | T | 146 | 95 | 212 | 126 |
| DISCRIMINATION: | | 3.7 | 3.0 | 1.8 | 1.8 |
| DELETION | A | 6 | 412 | 29 | 48 |
| 4/8 + 6/3 | C | 297 | 32 | 465 | 160 |
| | G | 8 | 77 | 10 | 4 |
| | T | 8 | 26 | 31 | 5 |
| DISCRIMINATION: | | 37.1 | 5.4 | 15 | 3.3 |
| STANDARD | A | 347 | 533 | 228 | 277 |
| (10/7) | C | 729 | 194 | 536 | 496 |
| | G | 232 | 231 | 102 | 89 |
| | T | 344 | 133 | 163 | 150 |
| DISCRIMINATION: | | 2.1 | 2.3 | 2.3 | 1.8 |

The use of deletion or bridging probes is quite general. These probes can be used in any of the tiling strategies of the invention. As well as offering superior discrimination, the use of deletion or bridging strategies is advantageous for certain probes to avoid self-hybridization (either within a probe or between two probes of the same sequence)

11. Nucleotide Repeats

Recently a new form of human mutation, expansion of trinucleotide repeats, has been found to cause the diseases of fragile X-syndrome, spinal and bulbar atrophy, myotonic dystrophy and Huntington's disease. See Ross et al., *TINS* 16, 254-259 (1993). Long lengths of trinucleotide repeats are associated with the mutant form of a gene. The longer the length, the more severe the consequences of the mutation and the earlier the age of onset. The invention provides arrays and methods for analyzing the length of such repeats.

The different probes in such an array comprise different numbers of repeats of the complement of the trinucleotide repeat of interest. For example, one probe might be a trimer, having one copy of the repeat, a second probe might be a sixmer, having two copies of the repeat, and a third probe might be a ninmer having three copies, and so forth. The largest probes can have up to about sixty bases or 20 trinucleotide repeats.

The hybridization signal of such probes to a target of trinucleotide repeats is related to the length of the target. It has been found that on increasing the target size up to about the length of the probe, the hybridization signal shows a relatively large increase for each complete trinucleotide repeat unit in the target, and a small increase for each additional base in the target that does not complete a trinucleotide repeat. Thus, for example, the hybridization signals for different target sizes to a 20 mer probe show small increases as the target size is increased from 6-8 nucleotides and a larger increase as the target size is increased to 9 nucleotides.

Arrays of probes having different numbers of repeats are usually calibrated using known amounts of target of different length. For each target of known length, the hybridization intensity is recorded for each probe. Thus, each target size is defined by the relative hybridization signals of a series of probes of different lengths. The array is then hybridized to an unknown target sequence and the relative hybridization signals of the different sized probes are determined. Comparison of the relative hybridization intensity profile for different probes with comparable data for targets of known size allows interpolation of the size of the unknown target. Optionally, hybridization of the unknown target is performed simultaneously with hybridization of a target of known size labelled with a different color.

C. Preparation of Target Samples

The target polynucleotide, whose sequence is to be determined, is usually isolated from a tissue sample. If the target is genomic, the sample may be from any tissue (except exclusively red blood cells). For example, whole blood, peripheral blood lymphocytes or PBMC, skin, hair or semen are convenient sources of clinical samples. These sources are also suitable if the target is RNA. Blood and other body fluids are also a convenient source for isolating viral nucleic acids. If the target is mRNA, the sample is obtained from a tissue in which the mRNA is expressed. If the polynucleotide in the sample is RNA, it is usually reverse transcribed to DNA. DNA samples or cDNA resulting from reverse transcription are usually amplified, e.g., by PCR. Depending on the selection of primers and amplifying enzyme(s), the amplification product can be RNA or DNA. Paired primers are selected to flank the borders of a target polynucleotide of interest. More than one target can be simultaneously amplified by multiplex PCR in which multiple paired primers are employed. The target can be labelled at one or more nucleotides during or after amplification. For some target polynucleotides (depending on size of sample), e.g., episomal DNA, sufficient DNA is present in the tissue sample to dispense with the amplification step.

When the target strand is prepared in single-stranded form as in preparation of target RNA, the sense of the strand should of course be complementary to that of the probes on the chip. This is achieved by appropriate selection of primers. The target is preferably fragmented before application to the chip to reduce or eliminate the formation of secondary structures in the target. The average size of targets segments following hybridization is usually larger than the size of probe on the chip.

II. Cystic Fibrosis Chips

A number of years ago, cystic fibrosis, the most common severe autosomal recessive disorder in humans, was shown to be associated with mutations in a gene thereafter named the Cystic Fibrosis Transmembrane Conductance Regulator (CFTR) gene. The CFTR gene is about 250 kb in size and has 27 exons. It is processed into a 6.5 kilobase mRNA that encodes a 1480 amino acid glycosylated, transmembrane protein with two intracellular ATP binding domains. Wild-type genomic sequence is available for all exonic regions and exons/intron boundaries (Zielenski et al., *Genomics* 10, 214-228 (1991). The full-length wildtype cDNA sequence has also been described (see Riordan et al., *Science* 245, 1059-1065 (1989). Over 500 mutations have been mapped (see, e.g., Tsui et al, *Hu. Mutat.* 1, 197-203 (1992). Some of the more common mutations that have been analyzed by the present arrays are shown in Table 3.

About 90% of all mutations having phenotypic effects occur in coding regions. Other mutations occur in splice site consensus sequences, introns and the promoter region. The most common cystic fibrosis mutation is a three-base deletion resulting in the omission of amino acid #508 from the CFTR protein. The frequency of mutations varies widely in populations of different geographic or ethnic origin (see column 4 of Table 3). Another 15 mutations each represent from 1% to 4% of reported CFTR mutations and another 16 each account for 0.2% to 1% of CFTR mutations. Together these 32 mutations account for approximately 90% of the North American and Western European CF mutations. For CF testing to be effective, a test must either be generic (include all reasonably frequent mutations) or be tailored to the test population.

Detection of CFTR mutations is useful in a number of respects. For example, screening of populations can identify asymptomatic heterozygous individuals. Such individuals are at risk of giving rise to affected offspring suffering from CF if they reproduce with other such individuals. In utero screening of fetuses is also useful in identifying fetuses bearing 2 CFTR mutations. Identification of such mutations offers the possibility of abortion, or gene therapy. For couples known to be at risk of giving rise to affected progeny, diagnosis can be combined with in vitro reproduction procedures to identify an embryo having at least one wildtype CF allele before implantation. Screening children shortly after birth is also of value in identifying those having 2 copies of the defective gene. Early detection allows administration of appropriate treatment (e.g., Pulmozyme Antibiotics, Pertussive Therapy) thereby improving the quality of life and perhaps prolonging the life expectancy of an individual.

The source of target DNA for detecting of CFTR mutations is usually genomic. In adults, samples can conveniently be obtained from blood or mouthwash epithelial cells. In fetuses, samples can be obtained by several conventional techniques such as amniocentesis, chorionic villus sampling or fetal blood sampling. At birth, blood from the amniotic chord is a useful tissue source.

The target DNA is usually amplified by PCR. Some appropriate pairs of primers for amplifying segments of DNA including the sites of known mutations are listed in Tables 3 and 4.

TABLE 4

| OLIGO NUMBER | SEQUENCE (SEQ. ID. Nos. 72-102) |
|---|---|
| 787 | TCTCCTTGGATATACTTGTGTGAATCAA |
| 788 | TCACCAGATTTCGTAGTCTTTTCATA |
| 851 | GTCTTGTGTTGAAATTCTCAGGGTAT |
| 769 | CTTGTACCAGCTCACTACCTAAT |
| 887 | ACCTGAGAAGATAGTAAGCTAGATGAA |
| 888 | AACTCCGCCTTTCCAGTTGTAT |
| 934 | TTAGTTTCTAGGGGTGGAAGATACA |
| 935 | TTAATGACACTGAAGATCACTGTTCTAT |
| 789 | CCATTCCAAGATCCCTGATATTTGAA |
| 790 | GCACATTTTTGCAAAGTTCATTAGA |
| 891 | TCATGGGCCATGTGCTTTTCAA |
| 892 | ACCTTCCAGCACTACAAACTAGAA |
| 760 | CAAGTGAATCCTGAGCGTGATTT |
| 850 | GGTAGTGTGAAGGGTTCATATGCATA |
| 762 | GATTACATTAGAAGGAAGATGTGCCTTT |
| 763 | ACATGAATGACATTTACAGCAAATGCTT |
| 931 | GTGACCATATTGTAATGCATGTAGTGA |
| 932 | ATGGTGAACATATTTCTCAAGAGGTAA |
| 955 | TGT CTC TGT AAA CTG ATG GCT AAC A |
| 884 | TCGTATAGAGTTGATTGGATTGAGAA |
| 885 | CCATTAACTTAATGTGGTCTCATCACAA |
| 886 | CTACCATAATGCTTGGGAGAAATGAA |
| 782 | TCAAAGAATGGCACCAGTGTGAAA |
| 901 | TGCTTAGCTAAAGTTAATGAGTTCAT |
| 784 | AATTGTGAAATTGTCTGCCATTCTTAA |
| 785 | GATTCACTTACTGAACACAGTCTAACAA |
| 791 | AGGCTTCTCAGTGATCTGTTG |
| 792 | GAATCATTCAGTGGGTATAAGCA |
| 1013 | GCCATGGTACCTATATGTCACAGAA |
| 1012 | TGCAGAGTAATATGAATTTCTTGAGTACA |
| 766 | GGGACTCCAAATATTGCTGTAGTAT |
| 1065 | GTACCTGTTGCTCCAGGTATGTT |

Other primers can be readily devised from the known genomic and cDNA sequences of CFTR. The selection of primers, of course, depends on the areas of the target sequence that are to be screened. The choice of primers also depends on the strand to be amplified. For some regions of the CFTR gene, it makes little difference to the hybridization signal whether the coding or noncoding strand is used. In other regions, one strand may give better discrimination in hybridization signals between matched and mismatched probes than the other. Thus, some chips may for example tile some exons based on the coding sequence and other exons based on the noncoding sequence. The selection is determined by the relative quality of mutation discrimination by the alternative probe sets and by the degree of cross hybridization seen with the final target complexity in the assay. The upper limit in the length of a segment that can be amplified from one pair of PCR primers is about 50 kb. Thus, for analysis of mutants through all or much of the CFTR gene, it is often desirable to amplify several segments from several paired primers. The different segments may be amplified sequentially or simultaneously by multiplex PCR. For example, the following groups of exons have been multiplexed: 21, 4, 10, 20 and 11; 19, 7, 19, 3 and 5; and 17, 9, 14, 13, 6, and 12. A multiplex of exons 4, 10, 11, 20 and 21 accounts for approximately 90% of all mutant CF chromosomes. This multiplex hybridization gives excellent results when exon 4, 11 and 20 coding strands are combined with exon 10 and 21 noncoding strands.

The primers and amplification conditions are preferably selected to generate DNA targets. An asymmetric labelling strategy incorporating fluorescently labelled dNTPs for random labelling and dUTP for target fragmentation to an average length of less than 60 bases is preferred. The use of dUTP and fragmentation with uracil N-glycosylase has the added advantage of eliminating carry over between samples.

Mutations in the CFTR gene can be detected by any of the tiling strategies noted above. The block tiling strategy is one particularly useful approach. In this strategy, a group (or block) of probes is used to analyze a short segment of contiguous nucleotides (e.g., 3, 5, 7 or 9) from a CFTR gene centered around the site of a mutation. The probes in a group are sometimes referred to as constituting a block because all probes in the group are usually identical except at their interrogation positions. As noted above, the probes may also differ in the presence of leading or trailing sequences flanking regions of complementarity. However, for ease of illustration, it will be assumed that such sequences are not present. As an example, to analyze a segment of five contiguous nucleotides from the CFTR gene, including the site of a mutation (such as one of the mutations in Table 3), a block of probes usually contains at least one perfectly matched probe and five sets of mismatched probes, each set having three probes.

The perfectly matched probe has five interrogation positions corresponding to the five nucleotides being analyzed from the reference sequence. However, the identity of the interrogation positions is only apparent when the structure of the perfectly matched probe is compared with that of the probes in the five mismatched probe sets. The first mismatched probe set comprises three probes, each being identical to the perfectly matched probe, except in the first interrogation position, which differs in each of the three mismatched probes and the perfectly matched probe. The second through fifth mismatched probe sets are similarly comprised except that the differences from the perfectly matched probe occur in the second through fifth interrogation position respectively.

Note that in practice, each set of mismatched probes is sometimes laid down on the chip juxtaposed with an associated perfectly matched probe. In this situation, a block comprises five perfectly matched probes, each effectively providing the same information. However, visual inspection and level of confidence are facilitated by the largely redundant information provided by five perfectly matched probes.

After hybridization to labelled target, the relative hybridization signals are read from the probes. Comparison of the intensities of the three probes in the first mismatched probe set with that of the perfectly matched probe indicates the identity of the nucleotide in the target sequence corresponding to the first interrogation position. This nucleotide is the complement of the nucleotide occupying the interrogation position in the probe having the highest signal. Comparison of the intensities of the three probes in the second mismatched probe set with that of the perfectly matched probe indicates the identity of the nucleotide in the target sequence corresponding to the second interrogation position (again the complement of the nucleotide occupying the interrogation position in the probe showing the highest signal), and so forth. Collectively, the relative hybridization intensities indicate the identity of each of the five contiguous nucleotides in the reference sequence.

In a preferred embodiment, a first group (or block) of probes is tiled based on a wildtype reference sequence and a second group is tiled based a mutant version of the wildtype reference sequence. The mutation can be a point mutation, insertion or deletion or any combination of these. The combination of first and second groups of probes facilitates analysis when multiple target sequences are simultaneously applied to the chip, as is the case when a patient being diagnosed is heterozygous for the CFTR allele.

Figure 10:
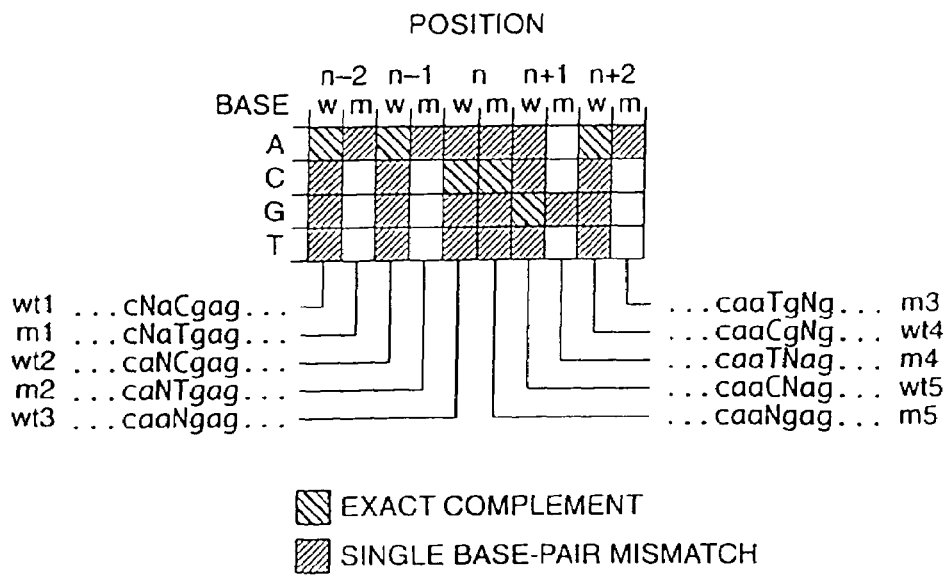
FIG. 10: Block tiling array of probes for analyzing a CFTR point mutation. Each probe shown actually represents four probes, with one probe having each of A, C, G or T at the interrogation position N. In the order shown, the first probe shown on the left is tiled from the wildtype reference sequence (SEQ. ID. No. 215), the second probe from the mutant sequence (SEQ. ID. No. 216), and so on in alternating fashion. Note that all of the probes are identical except at the interrogation position, which shifts one position between successive probes tiled from the same reference sequence (e.g., the first, third and fifth probes in the left hand column.) The grid shows the hybridization intensities when the array is hybridized to the reference sequence.

The above strategy is illustrated in FIG. 10, which shows two groups of probes tiled for a wildtype reference sequence and a point mutation thereof. The five mismatched probe sets for the wildtype reference sequence are designated wt1-5, and the five mismatched probe sets for the mutant reference sequence are designated m1-5. The letter N indicates the interrogation position, which shifts by one position in successive probe sets from the same group. The figure illustrates the hybridization pattern obtained when the chip is hybridized with a homozygous wildtype target sequence comprising nucleotides n−2 to n+2, where n is the site of a mutation. For the group of probes tiled based on the reference sequence, four probes are compared at each interrogation position. At each position, one of the four probes exhibits a perfect match with the target, and the other three exhibit a single-base mismatch. For the group of probes tiled based on the mutant reference sequence, again four probes are compared at each interrogation position. At position, n, one probe exhibits a perfect match, and three probes exhibit a single base mismatch. At other positions, no probe exhibits a perfect match.

Hybridization to a homozygous mutant yields an analogous pattern, except that the respective hybridization patterns of probes tiled on the wildtype and mutant reference sequences are reversed.

Figure 11:
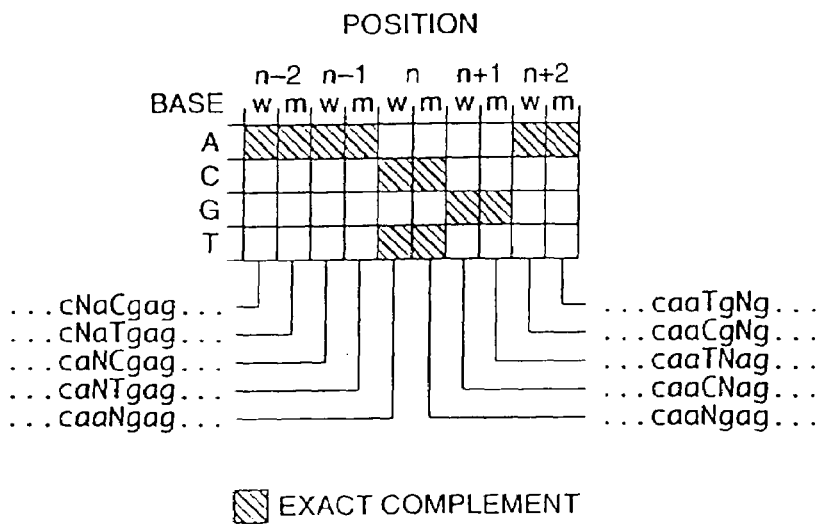
FIG. 11: Hybridization pattern for heterozygous target. The figure shows the hybridization pattern when the array of the previous figure is hybridized to a mixture of mutant and wildtype reference sequences.

The hybridization pattern is very different when the chip is hybridized with a sample from a patient who is heterozygous for the mutant allele (see FIG. 11). For the group of probes tiled based on the wildtype sequence, at all positions but n, one probe exhibits a perfect match at each interrogation position, and the other three probes exhibit a one base mismatch. At position n, two probes exhibit a perfect match (one for each allele), and the other probes exhibit single-base mismatches. For the group of probes tiled on the mutant sequence, the same result is obtained. Thus, the heterozygote point mutant is easily distinguished from both the homozygous wildtype and mutant forms by the identity of hybridization patterns from the two groups of probes.

Typically, a chip comprises several paired groups of probes, each pair for detecting a particular mutation. For example, some chips contain 5, 10, 20, 40 or 100 paired groups of probes for detecting the corresponding numbers of mutations. Some chips are customized to include paired groups of probes for detecting all mutations common in particular populations (see Table 3).

Chips usually also contain control probes for verifying that correct amplification has occurred and that the target is properly labelled. Control probes include a probe for the 5' PCR primer, a probe for a sequence in each exon target that is 3' to the mutations in that exon together with probes used as alignment guides to delineate the different zones on the chip.

The goal of the tiling strategy described above is to focus on short regions of the CTFR region flanking the sites of known mutation. Other tiling strategies analyze much larger regions of the CFTR gene, and are appropriate for locating and identifying hitherto uncharacterized mutations. For example, the entire genomic CFTR gene (250 kb) can be tiled by the basic tiling strategy from an array of about one million probes. Synthesis and scanning of such an array of probes is entirely feasible. Other tiling strategies, such as the block tiling, multiplex tiling or pooling can cover the entire gene with fewer probes. Some tiling strategies analyze some or all of components of the CFTR gene, such as the cDNA coding sequence or individual exons. Analysis of exons 10 and 11 is particularly informative because these are location of many common mutations including the ΔF508 mutation.

Exemplary CFTR chips
(a) Exon 10 Chip

One illustrative chip bears an array of 1296 probes covering the full length of exon 10 of the CFTR gene arranged in a 36×36 array of 356 μm elements. The probes in the array can have any length, preferably in the range of from 10 to 18 residues and can be used to detect and sequence any single-base substitution and any deletion within the 192-base exon, including the three-base deletion known as ΔF508. As described in detail below, hybridization of nanomolar concentrations of wild-type and ΔF508 oligonucleotide target nucleic acids labeled with fluorescein to these arrays produces highly specific signals (detected with confocal scanning fluorescence microscopy) that permit discrimination between mutant and wild-type target sequences in both homozygous and heterozygous cases.

Sets of probes of a selected length in the range of from 10 to 18 bases and complementary to subsequences of the known wild-type CFTR sequence are synthesized starting at a position a few bases into the intron on the 5'-side of exon 10 and ending a few bases into the intron on the 3'-side. There is a probe for each possible subsequence of the given segment of the gene, and the probes are organized into a "lane" in such a way that traversing the lane from the upper left-hand corner of the chip to the lower righthand corner corresponded to traversing the gene segment base-by-base from the 5'-end. The lane containing that set of probes is, as noted above, called the "wild-type lane."

Relative to the wild-type lane, a "substitution" lane, called the "A-lane", was synthesized on the chip. The A-lane probes were identical in sequence to an adjacent (immediately below the corresponding) wild-type probe but contained, regardless of the sequence of the wild-type probe, a dA residue at position 7 (counting from the 3'-end). In similar fashion, substitution lanes with replacement bases dC, dG, and dT were placed onto the chip in a "C-lane," a "G-lane," and a "T-lane," respectively. A sixth lane on the chip consisted of probes identical to those in the wild-type lane but for the deletion of the base in position 7 and restoration of the original probe length by addition to the 5'-end the base complementary to the gene at that position.

The four substitution lanes enable one to deduce the sequence of a target exon 10 nucleic acid from the relative intensities with which the target hybridizes to the probes in the various lanes. Various versions of such exon 10 DNA chips were made as described above with probes 15 bases long, as well as chips with probes 10, 14, and 18 bases long. For the results described below, the probes were 15 bases long, and the position of substitution was 7 from the 3'-end.

The sequences of several important probes are shown below (SEQ. ID. Nos. 103-111). In each case, the letter "X" stands for the interrogation position in a given column set, so each of the sequences actually represents four probes, with A, C, G, and T, respectively, taking the place of the "X." Sets of shorter probes derived from the sets shown below by removing up to five bases from the 5'-end of each probe and sets of longer probes made from this set by adding up to three bases from the exon 10 sequence to the 5'-end of each probe, are also useful and provided by the invention.

```
3'-TTTATAXTAGAAACC

3'-  TTATAGXAGAAACCA

3'-   TATAGTXGAAACCAC

3'-    ATAGTAXAAACCACA

3'-     TAGTAGXAACCACAA

3'-      AGTAGAXACCACAAA

3'-       GTAGAAXCCACAAAG

3'-        TAGAAAXCACAAAGG

3'-         AGAAACXACAAAGGA
```

To demonstrate the ability of the chip to distinguish the ΔF508 mutation from the wild-type, two synthetic target nucleic acids were made. The first, a 39-mer complementary to a subsequence of exon 10 of the CFTR gene having the three bases involved in the ΔF508 mutation near its center, is called the "wild-type" or wt508 target, corresponds to positions 111-149 of the exon, and has the sequence shown below (SEQ. ID.No. 112): 5'-CATTAAAGAAAATAT-CATCTTTGGTGTTTCCTATGATGA.

The second, a 36-mer probe derived from the wild-type target by removing those same three bases, is called the "mutant" target or mu508 target and has the sequence shown below, first with dashes to indicate the deleted bases, and then without dashes but with one base underlined (to indicate the base detected by the T-lane probe, as discussed below) (SEQ. ID. No. 113):

```
5'-CATTAAAGAAAATATCAT---TGGTGTTTCCTATGATGA;

5'-CATTAAAGAAAATATCATTGGTGTTTCCTATGATGA.
```

Both targets were labeled with fluorescein at the 5'-end.

In three separate experiments, the wild-type target, the mutant target, and an equimolar mixture of both targets was exposed (0.1 nM wt508, 0.1 nM mu508, and 0.1 nM wt508 plus 0.1 nM mu508, respectively, in a solution compatible with nucleic acid hybridization) to a CF chip. The hybridization mixture was incubated overnight at room temperature, and then the chip was scanned on a reader (a confocal fluorescence microscope in photon-counting mode); images of the chip were constructed from the photon counts) at several successively higher temperatures while still in contact with the target solution. After each temperature change, the chip was allowed to equilibrate for approximately one-half hour before being scanned. After each set of scans, the chip was exposed to denaturing solvent and conditions to wash, i.e., remove target that had bound, the chip so that the next experiment could be done with a clean chip.

Figure 13A:
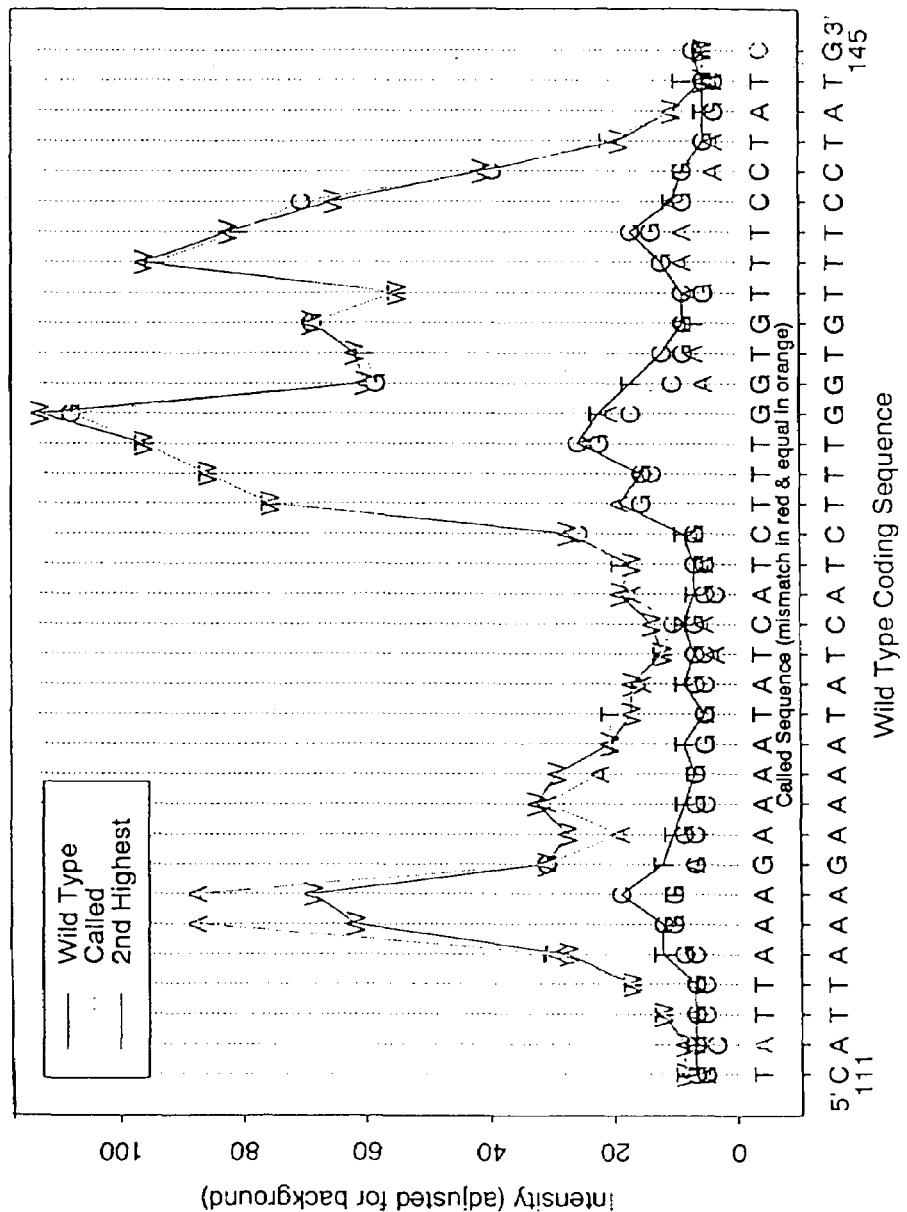
FIG. 13, in sheets 1-3, corresponding to panels A, B, and C of FIG. 12, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest"). The called sequences in A, B and C are (SEQ. ID. Nos. 22 1-223).
Figure 13B:
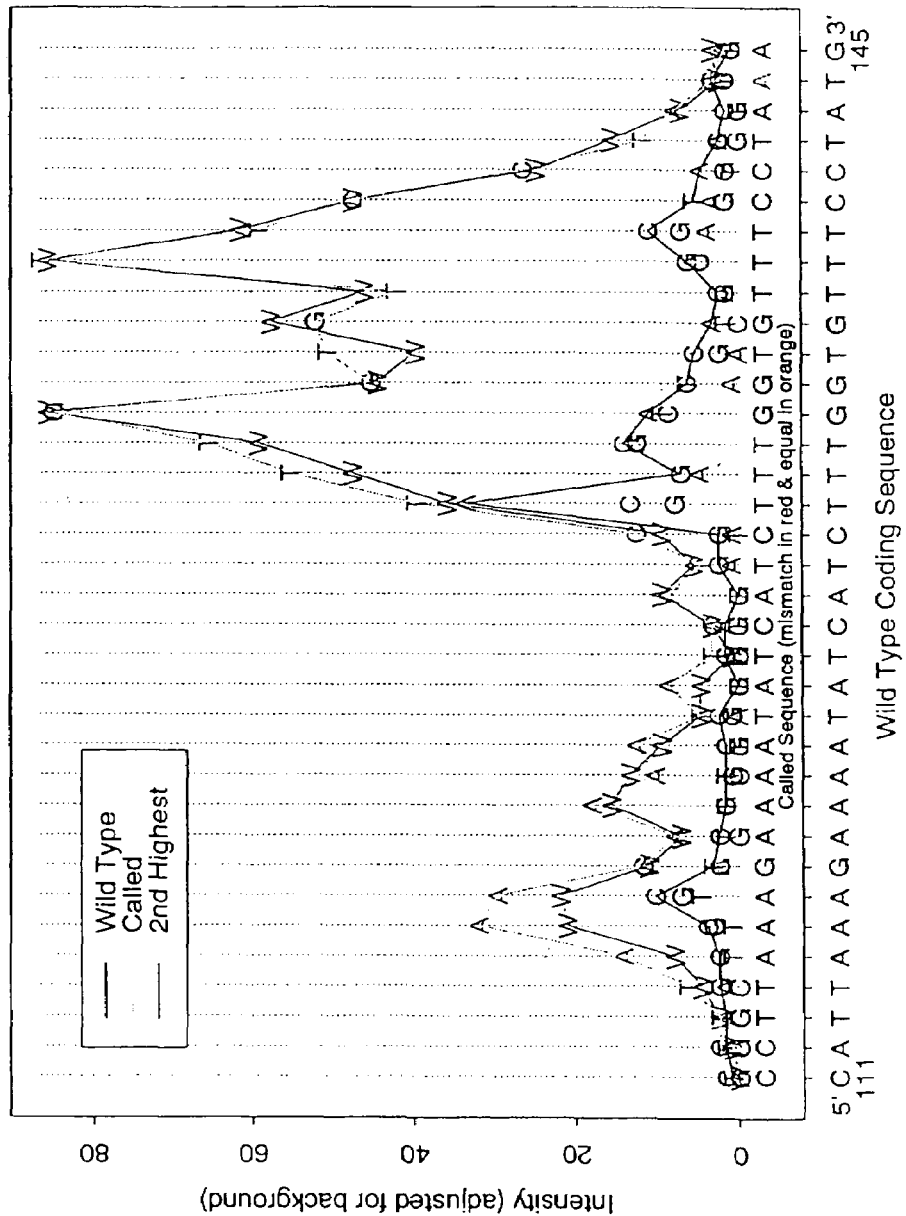
Figure 13C:
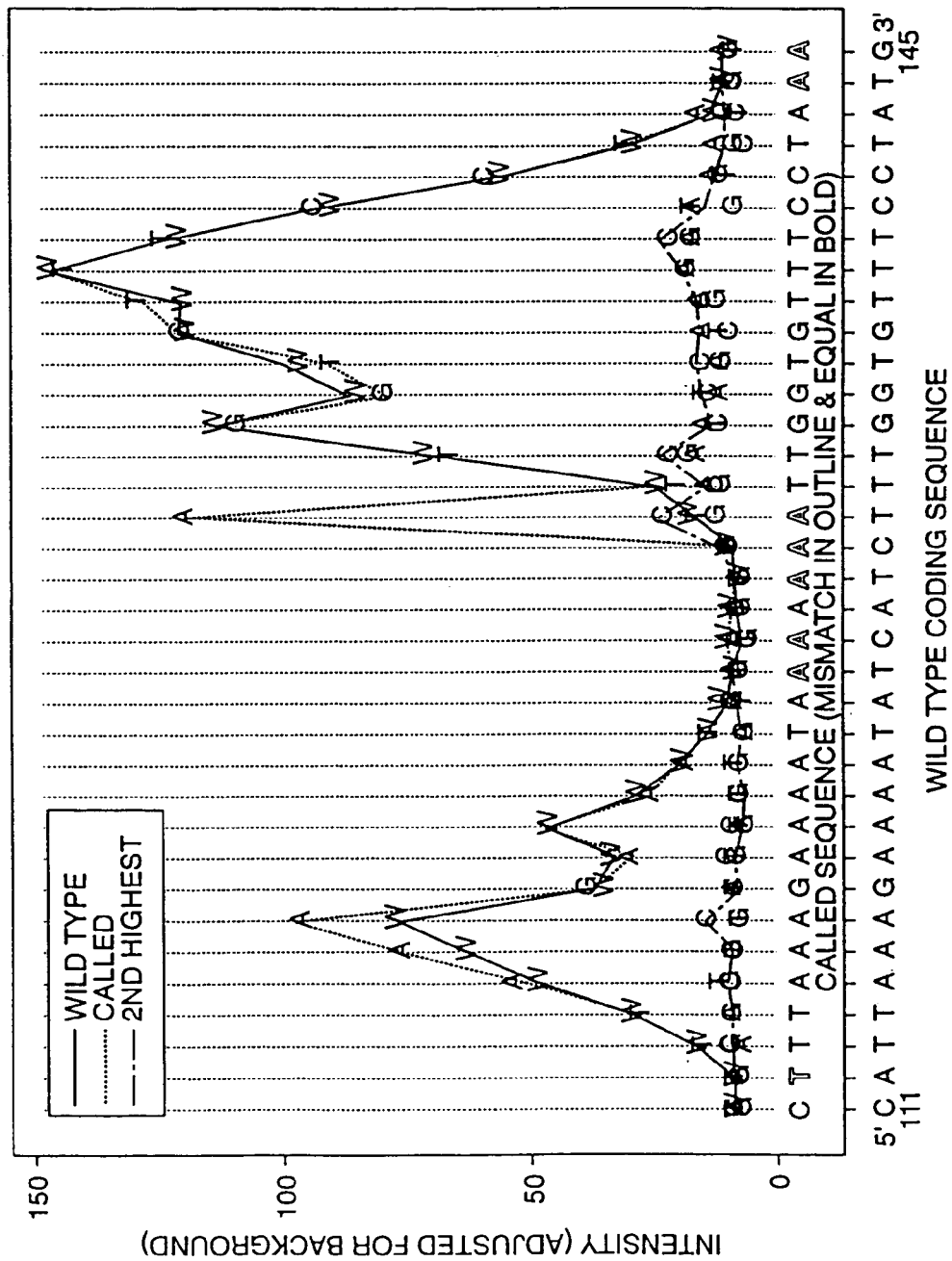

The results of the experiments are shown in FIGS. 12, 13, 14, and 15. FIG. 12, in panels A, B, and C, shows an image made from the region of a DNA chip containing CFTR exon 10 probes; in panel A, the chip was hybridized to a wild-type target; in panel C, the chip was hybridized to a mutant ΔF508 target; and in panel B, the chip was hybridized to a mixture of the wild-type and mutant targets. FIG. 13, in sheets 1-3, corresponding to panels A, B, and C of FIG. 12, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest").

These figures show that, for the wild-type target and the equimolar mixture of targets, the substitution probe with a nucleotide sequence identical to the corresponding wild-type probe bound the most target, allowing for an unambiguous assignment of target sequence as shown by letters near the points on the curve. The target wt508 thus hybridized to the probes in the wild-type lane of the chip, although the strength of the hybridization varied from probe-to-probe, probably due to differences in melting temperature. The sequence of most of the target can thus be read directly from the chip, by inference from the pattern of hybridization in the lanes of substitution probes (if the target hybridizes most intensely to the probe in the A-lane, then one infers that the target has a T in the position of substitution, and so on).

For the mutant target, the sequence could similarly be called on the 3'-side of the deletion. However, the intensity of binding declined precipitously as the point of substitution approached the site of the deletion from the 3'-end of the target, so that the binding intensity on the wild-type probe whose point of substitution corresponds to the T at the 3'-end of the deletion was very close to background. Following that pattern, the wild-type probe whose point of substitution corresponds to the middle base (also a T) of the deletion bound still less target. However, the probe in the T-lane of that column set bound the target very well. Examination of the sequences of the two targets reveals that the deletion places an A at that position when the sequences are aligned at their 3'-ends and that the T-lane probe is complementary to the mutant target with but two mismatches near an end (shown below in lower-case letters, with the position of substitution underlined):

```
Target:   5'-CATTAAAGAAAATATCATTGGTGTTTCCTATGATGA

Probe                    3'-TagTAGTAACCACAA
(SEQ. ID. No. 114):
```

Thus the T-lane probe in that column set calls the correct base from the mutant sequence. Note that, in the graph for the equimolar mixture of the two targets, that T-lane probe binds almost as much target as does the A-lane probe in the same column set, whereas in the other column sets, the probes that do not have wild-type sequence do not bind target at all as well. Thus, that one column set, and in particular the T-lane probe within that set, detects the ΔF508 mutation under conditions that simulate the homozygous case and also conditions that simulate the heterozygous case.

Although in this example the sequence could not be reliably deduced near the ends of the target, where there is not enough overlap between target and probe to allow effective hybridization, and around the center of the target, where hybridization was weak for some other reason, perhaps high AT-content, the results show the method and the probes of the invention can be used to detect the mutation of interest. The mutant target gave a pattern of hybridization that was very similar to that of the wt508 target at the ends, where the two share a common sequence, and very different in the middle, where the deletion is located. As one scans the image from right to left, the intensity of hybridization of the target to the probes in the wild-type lane drops off much more rapidly near the center of the image for mu508 than for wt508; in addition, there is one probe in the T-lane that hybridizes intensely with mu508 and hardly at all with wt508. The results from the equimolar mixture of the two targets, which represents the case one would encounter in testing a heterozygous individual for the mutation, are a blend of the results for the separate targets, showing the power of the invention to distinguish a wild-type target sequence from one containing the ΔF508 mutation and to detect a mixture of the two sequences.

The results above clearly demonstrate how the DNA chips of the invention can be used to detect a deletion mutation, ΔF508; another model system was used to show that the chips can also be used to detect a point mutation as well. One mutation in the CFTR gene is G480C, which involves the replacement of the G in position 46 of exon 10 by a T, resulting in the substitution of a cysteine for the glycine normally in position #480 of the CFTR protein. The model target sequences included the 21-mer probe wt480 to represent the wild-type sequence at positions 37-55 of exon 10:

```
5'-CCTTCAGAGGGTAAAATTAAG (SEQ. ID. No. 115) and
the 21-mer probe mu480 to represent
the mutant sequence:

5'-CCTTCAGAGTGTAAAATTAAG (SEQ. ID. No. 116).
```

Figure 15A:
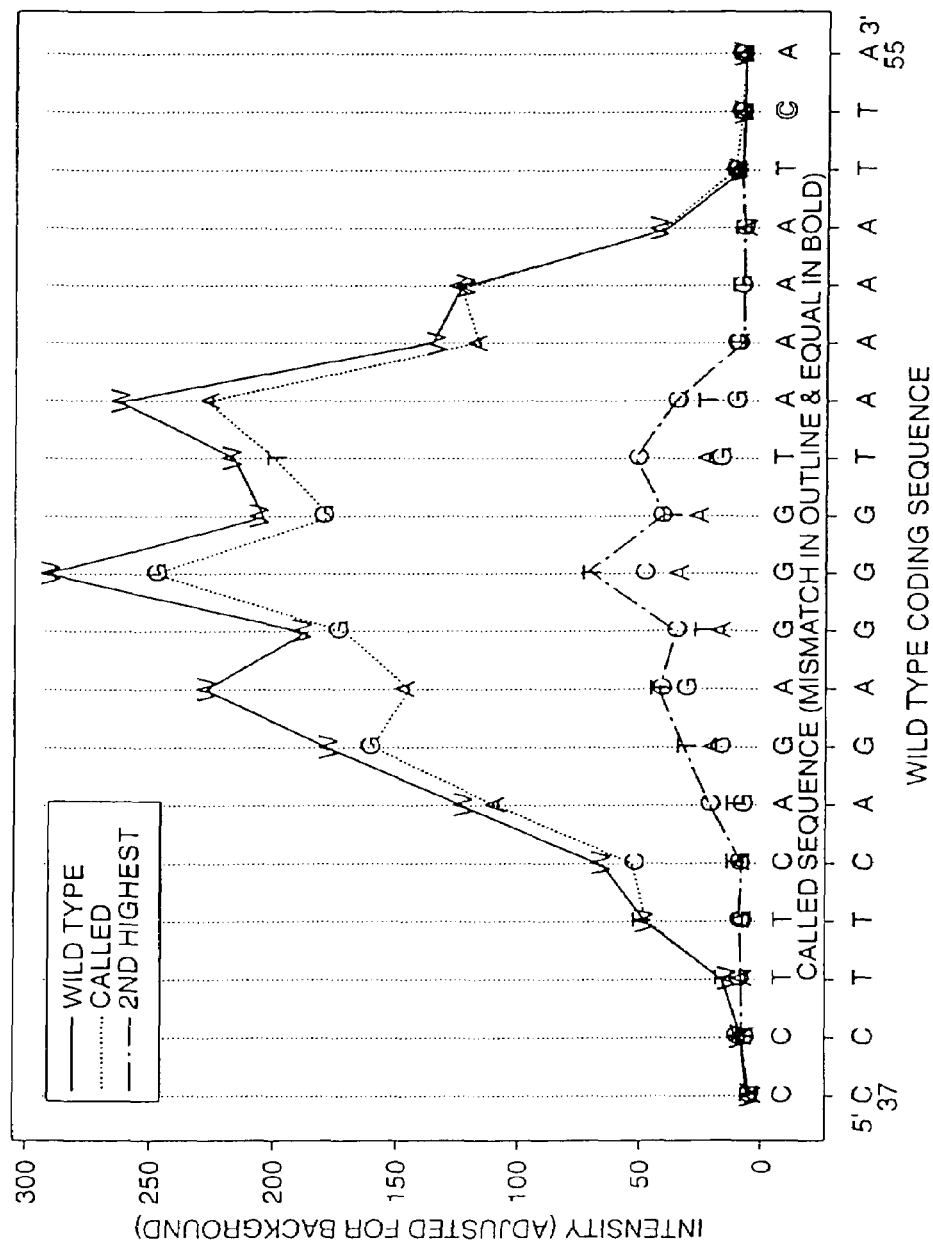
FIG. 15, in sheets 1-3, corresponding to panels A, B, and C of FIG. 14, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest"). Called (SEQ. ID. Nos. 228-230).
Figure 15B:
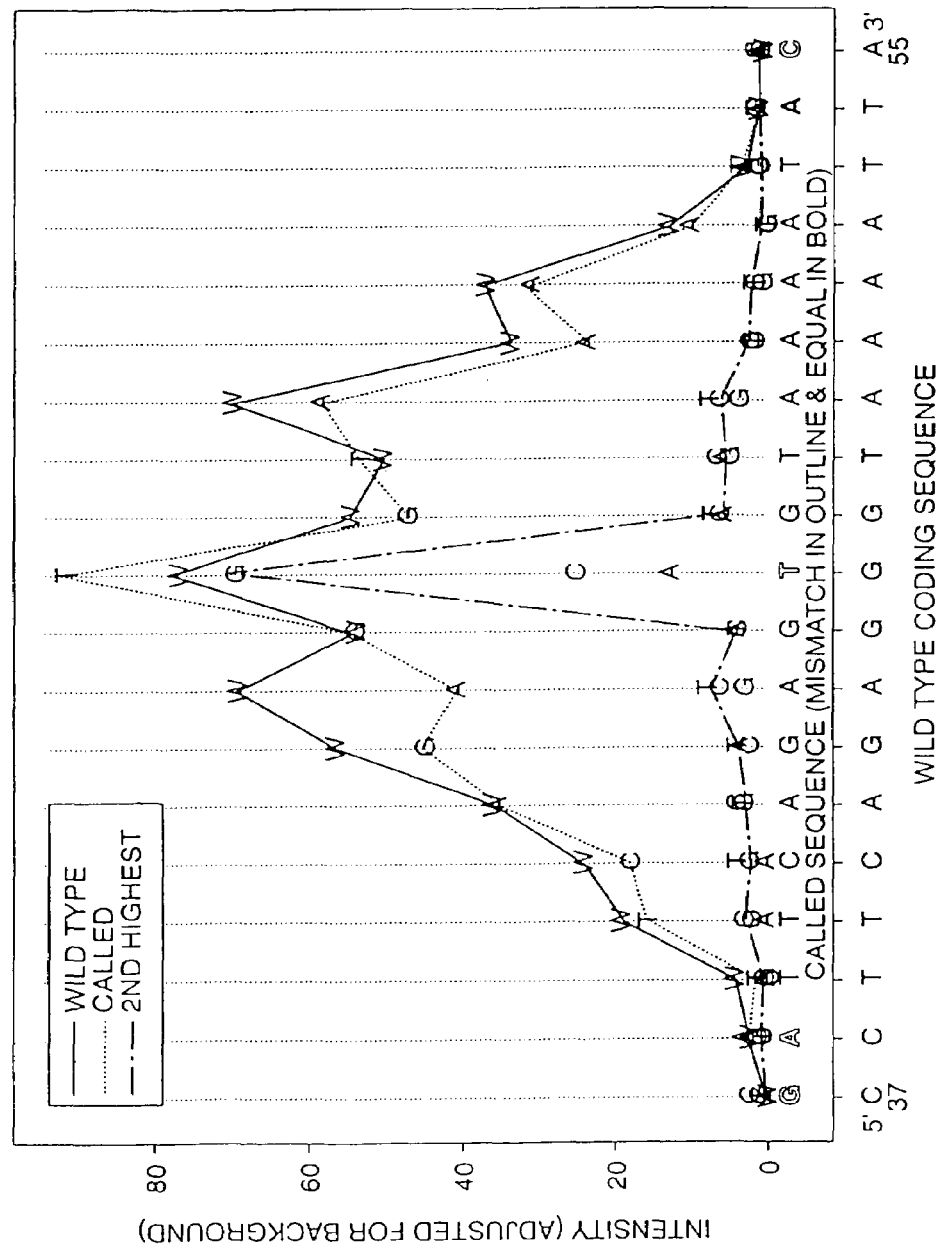
Figure 15C:
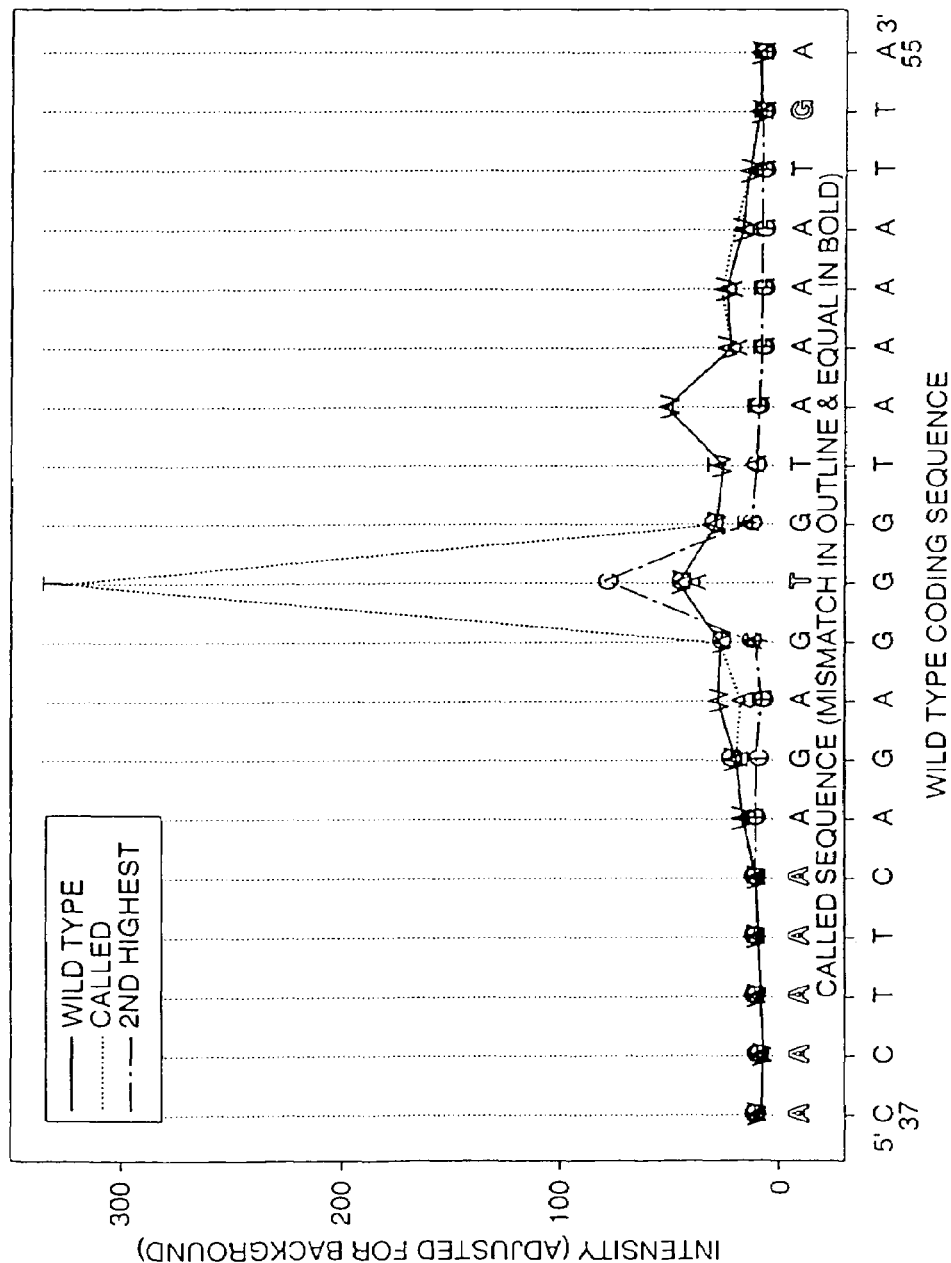

In separate experiments, a DNA chip was hybridized to each of the targets wt480 and mu480, respectively, and then scanned with a confocal microscope. FIG. 14, in panels A, B, and C, shows an image made from the region of a DNA chip containing CFTR exon 10 probes; in panel A, the chip was hybridized to the wt480 target; in panel C, the chip was hybridized to the mu480 target; and in panel B, the chip was hybridized to a mixture of the wild-type and mutant targets. FIG. 15, in sheets 1-3, corresponding to panels A, B, and C of FIG. 14, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest").

These figures show that the chip could be used to sequence a 16-base stretch from the center of the target wt480 and that discrimination against mismatches is quite good throughout the sequenced region. When the DNA chip was exposed to the target mu480, only one probe in the portion of the chip shown bound the target well: the probe in the set of probes devoted to identifying the base at position 46 in exon 10 and that has an A in the position of substitution and so is fully complementary to the central portion of the mutant target. All other probes in that region of the chip have at least one mismatch with the mutant target and therefore bind much less of it. In spite of that fact, the sequence of mu480 for several positions to both sides of the mutation can be read from the chip, albeit with much-reduced intensities from those observed with the wild-type target.

The results also show that, when the two targets were mixed together and exposed to the chip, the hybridization pattern observed was a combination of the other two patterns. The wild-type sequence could easily be read from the chip, but the probe that bound the mu480 target so well when only the mu480 target was present also bound it well when both the mutant and wild-type targets were present in a mixture, making the hybridization pattern easily distinguishable from that of the wild-type target alone. These results again show the power of the DNA chips of the invention to detect point mutations in both homo- and heterozygous individuals.

To demonstrate clinical application of the DNA chips of the invention, the chips were used to study and detect mutations in nucleic acids from genomic samples. Genomic samples from a individual carrying only the wild-type gene and an individual heterozygous for ΔF508 were amplified by PCR using exon 10 primers containing the promoter for T7 RNA polymerase. Illustrative primers of the invention are shown below (SEQ. ID. Nos. 117-122).

while the same probe binds little RNA from the wild-type individual. These results show that the DNA chips of the invention are capable of detecting the ΔF508 mutation in a heterozygous carrier.

(b) Exon 11 Chip

A further array was constructed according to the basic tiling strategy using the wildtype version of exon 11 as the reference sequence. The tiled array interrogates 107 nucleotides consisting of the 95 coding bases of CFTR exon 11, plus 1 nucleotide from the 5' intron and 11 nucleotides from the 3' intron. The array has 428 cells measuring 365 μm on each side. The array requires 50 photolysis/chemical coupling steps for synthesis. Each successive nucleotide in the target gene sequence is interrogated with a column of four probes, the probes in any one column offset from those in adjoining columns by one nucleotide.

Hybridization targets were prepared from normal human genomic DNA and from a synthetic R553X exon 11 generated by PCR. In this and subsequent experiments, typically, 100 ng of genomic DNA was amplified in a 50 μl reaction containing 0.4 μM of each primer, 50 μM each of dATP, dCTP, and dGTP, 40 μM TTP, 10 μM DUTP (all dNTPs from Pharmacia) and 2U Taq polymerase (Perkin-Elmer) in 10 mM Tris-Cl, pH 8.3, 50 mM KCl, 2.5 mM MgCl$_2$. The reactions were cycled 36 times in a Perkin-Elmer 9600 thermocycler

| Exon | Name | Sequence |
|---|---|---|
| 10 | CFi9-T7 | TAATACGACTCACTATAGGGAGatgacctaataatgatgggttt |
| 10 | CFi10c-T7 | TAATACGACTCACTATAGGGAGtagtgtgaagggttcatatgc |
| 10 | CFi10c-T3 | CTCGGAATTAACCCTCACTAAAGGtagtgtgaagggttcatatgc |
| 11 | CFi10-T7 | TAATACGACTCACTATAGGGAGagcatactaaaagtgactctc |
| 11 | CFi11c-T7 | TAATACGACTCACTATAGGGAGacatgaatgacatttacagcaa |
| 11 | CFi11c-T3 | CGGAATTAACCCTCACTAAAGGacatgaatgacatttacagcaa |

These primers can be used to amplify exon 10 or exon 11 sequences; in another embodiment, multiplex PCR is employed, using two or more pairs of primers to amplify more than one exon at a time.

Figure 16A:
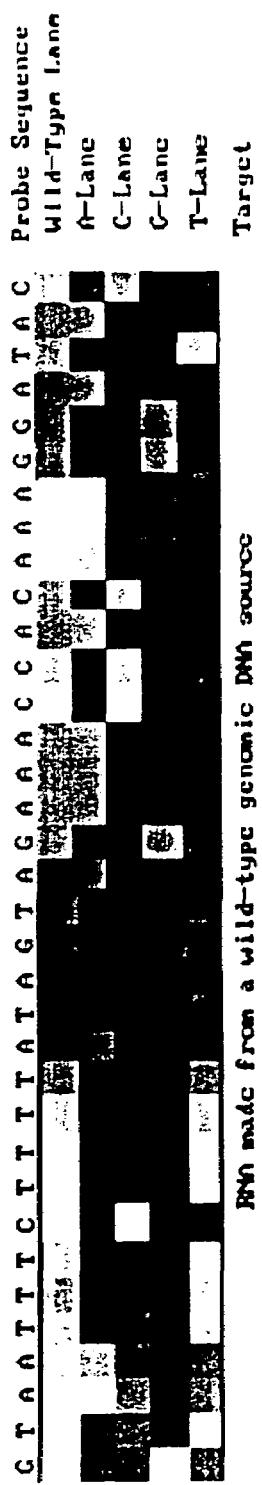
FIG. 16, in panels A and B, shows an image made from a region of a DNA chip containing CFTR exon 10 probes; in panel A, the chip was hybridized to nucleic acid derived from the genomic DNA of an individual with wild-type ΔF508 sequences (SEQ. ID. No. 231); in panel B, the target nucleic acid originated from a heterozygous (with respect to the ΔF508, mutation) individual.
Figure 16B:
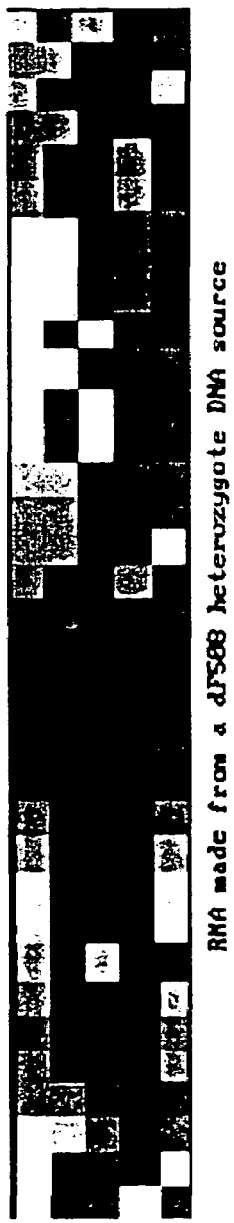
Figure 17:
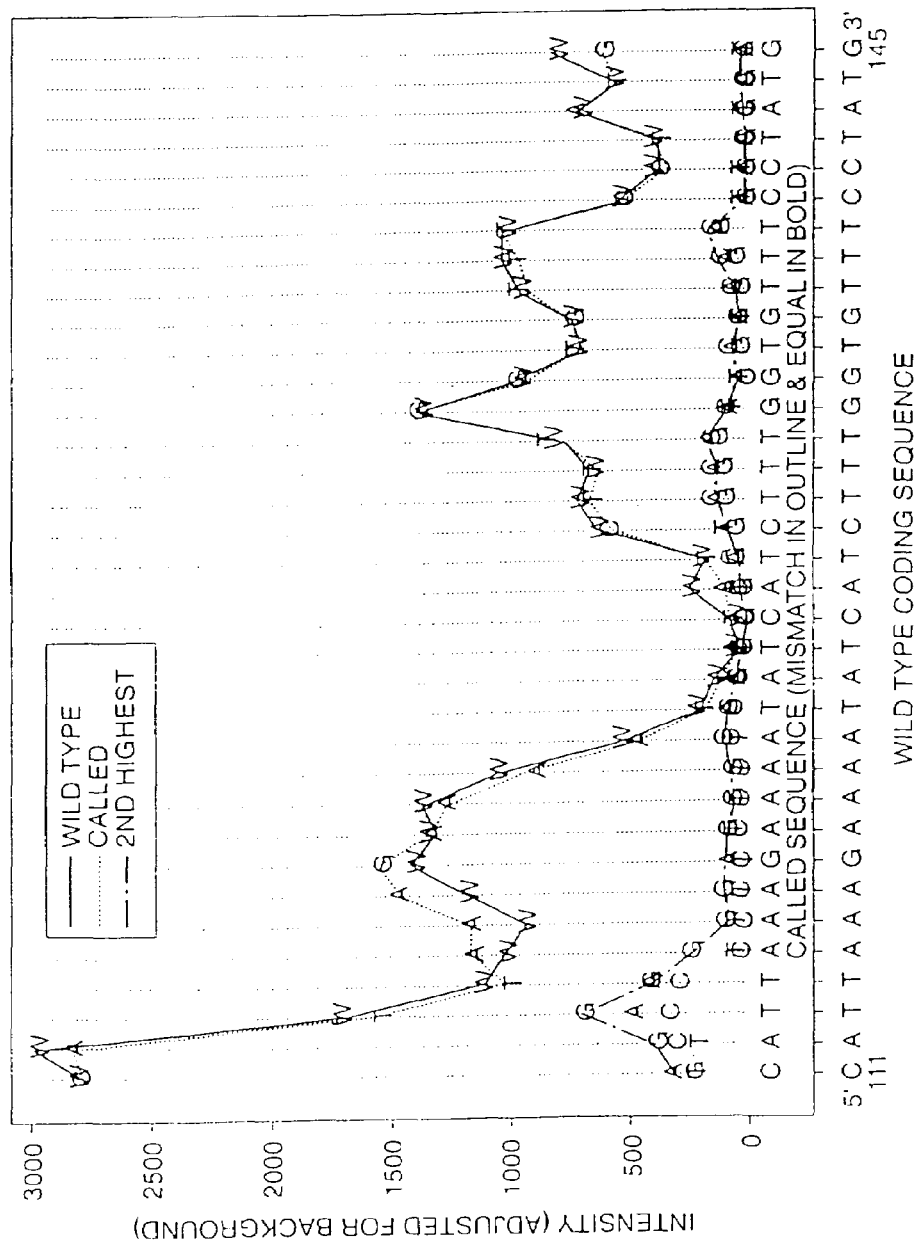
FIG. 17, in sheets 1 and 2 (SEQ. ID. No. 232), corresponding to panels A and B of FIG. 16, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest").
Figure 17:
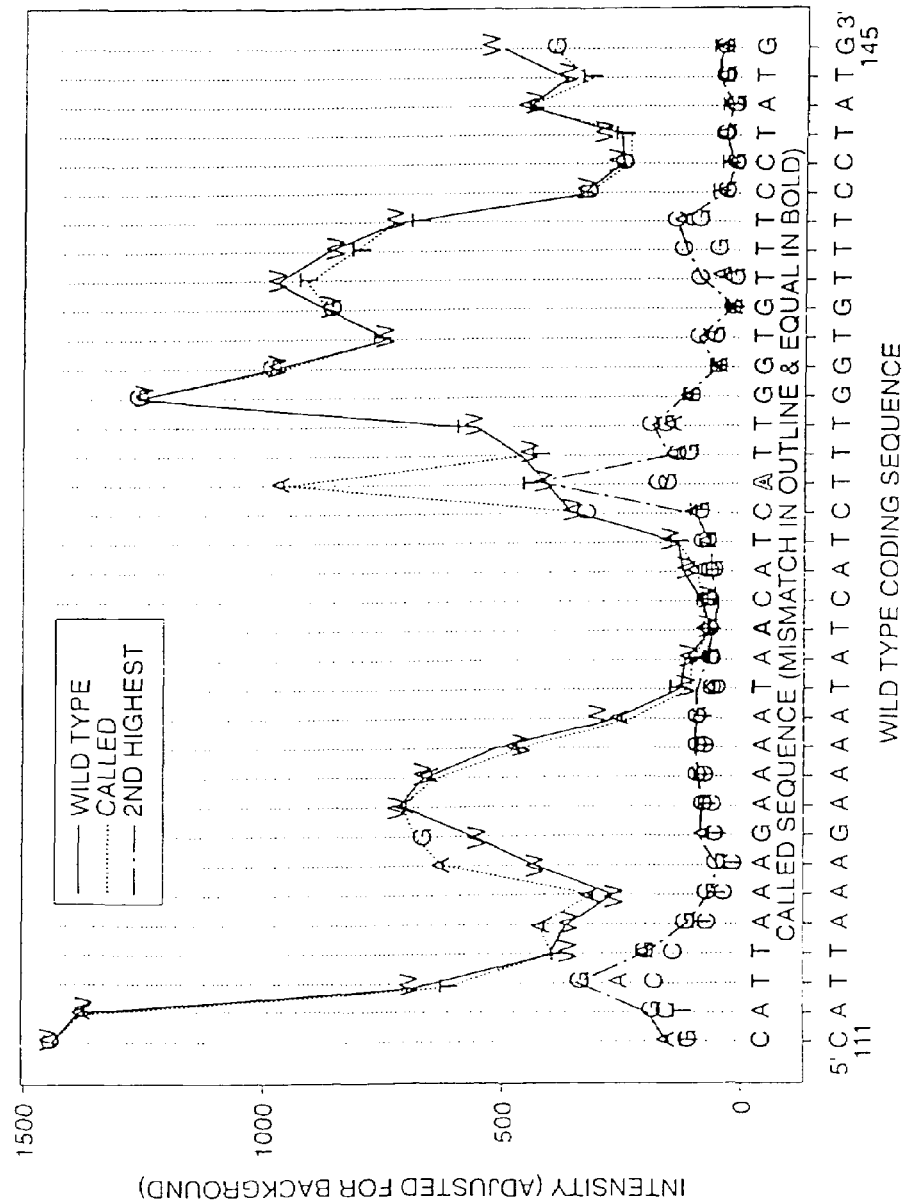

The product of amplification was then used as a template for the RNA polymerase, with fluoresceinated UTP present to label the RNA product. After sufficient RNA was made, it was fragmented and applied to an exon 10 DNA chip for 15 minutes, after which the chip was washed with hybridization buffer and scanned with the fluorescence microscope. A useful positive control included on many CF exon 10 chips is the 8-mer 3'-CGCCGCCG,-5'. FIG. 16, in panels A and B, shows an image made from a region of a DNA chip containing CFTR exon 10 probes; in panel A, the chip was hybridized to nucleic acid derived from the genomic DNA of an individual with wild-type ΔF508 sequences; in panel B, the target nucleic acid originated from a heterozygous (with respect to the ΔF508 mutation) individual. FIG. 17, in sheets 1 and 2, corresponding to panels A and B of FIG. 16, shows graphs of fluorescence intensity versus tiling position.

These figures show that the sequence of the wild-type RNA can be called for most of the bases near the mutation. In the case of the ΔF508 heterozygous carrier, one particular probe, the same one that distinguished so clearly between the wild-type and mutant oligonucleotide targets in the model system described above, in the T-lane binds a large amount of RNA, using the following temperatures and cycle times: 950° C., 10 sec., 55° C., 10 sec., 72° C., 30 sec. A 10 μl aliquot of this reaction product was introduced into a second, asymmetric PCR reaction, which produced a fluorescein-labeled, single stranded target for hybridization. Conditions for this 50 μl reaction included 1 mM asymmetric PCR primer, 50 μl each dATP and dCTP, 40 μM TTP, 10 μm dUTP, 25 μM dGTP, 25 μM fluorescein-12-dGTP (DuPont), and 0.5-1U Taq polymerase in 10 mM Tris-Cl, pH 9.1, 75 mM KCl 3.5 mM MgCl$_2$. The reaction was cycled 5 times using the following conditions: 95° C., 10 sec., 55° C., 1 min and 72° C., 1.5 min followed immediately by 20 of the following cycles: 95° C., 10 sec., 60° C., 10 sec., 72° C., 1.5 min The first five cycles allowed for standard PCR amplification of the original products, while the next 20 cycles allowed asymmetric PCR amplification from the longer, asymmetric PCR primer. Amplification products were fragmented by adding 2U of uracil-N-glycosylase (Gibco) and incubating at 37° C. for 30 min followed by heating the solution to 95° C. for 5 min (Lindahl et al., J. Biol. Chem. 252, 3286-3294 (1977); Longo et al., Gene 93, 125-128 (1990)). Labeled, fragmented PCR product (range=20 to 60 bases, average length=40 bases) was diluted 10 to 25 fold into 5×SSPE (750 mM NaCl, 50 mM NaPhosphate, 5 mM EDTA, pH 7.4) and 1 mM cetyltrimethylammonium bromide (CTAB, Sigma) and used directly in hybridizations.

Target was diluted into hybridization solution (10-40 nM final concentration, depending on PCR yield) and hybridization was carried out by agitating the DNA probe array in a 25 mm tissue culture dish placed in a temperature controlled shaker/incubator. Targets were hybridized separately in 1-3 ml of 5×SSPE with 10 mM CTAB at 30° C. for 30 minutes. The arrays were washed briefly (1-5 minutes) at 25° C.-30° C. with 5×SSPE and 0.01% SDS prior to imaging. A preliminary series of experiments established that 10 nM target begins to approach saturation of complementary probe hybridization sites within 30 minutes.

The hybridized DNA probe arrays were scanned using a confocal epifluorescent microscope and 488 nm argon ion laser excitation. Emitted light was collected through a band pass filter centered at 530 nm and detected with a photomultiplier tube equipped with photon counting electronics. For hybridization analysis the image file containing fluorescence intensity information was merged with a data file containing the probe sequence map.

Figure 18A:
FIG. 18 (SEQ. ID. Nos. 246-248): Image of the CFTR exon 11 tiled array hybridized with (A) wild-type and (B) mutant target.

FIG. 18A shows the image after hybridization of a wild-type target to the exon 11 array. The T, G, C, and A labels shown at the left side of FIG. 18A indicate the complement of the nucleotide occupying the interrogation position in the four lanes of probes running across the chip. This nucleotide is the same in each probe in the lane. In other words, all the probes in the lane to the right of the "T" have interrogation positions occupied by an A, all the probes in the lane to the right of the "G" have interrogation positions occupied by a C, and so forth. The letter at the base of each column identifies the complement of the nucleotide occupying the interrogation position in the probe having the highest hybridization intensity in that column. This is also the identity of the nucleotide occupying the corresponding position in the target sequence. Thus, comparison of each column of four probes identifies one base in the target sequence. Successive comparisons of successive columns reveal each base in the target sequence in the same order as the bases occur in the target.

The highest hybridization intensity in a column results from a perfect match of probe to target sequence. The weaker signals in a column result from lower stability duplexes formed with probes having imperfect complementarity (mismatches) with the target. The minimum acceptable signal for a base assignment to be made was a ratio of the highest raw signal to the next highest of the three remaining signals in each column of 1.3, although the ratio typically was >3.0. The relative fluorescence intensity range of all probes in the array was 144-1264.

Figure 18B:

FIG. 18B shows the same array hybridized with a homozygous R553X target. The arrow in the third row indicates the R553X C→T mutation position. The highest intensity signal at the arrow is now at the probe having an interrogation position complementary to T rather than C. Every other nucleotide assignment is the same as the wildtype sequence. The relative fluorescence intensity range was 400-1744.

c. Mutation-Specific Chips

Although the basic tiling strategy is generally satisfactory, it is evident from FIGS. 18A and 18B that signal intensities of perfect match hybridizations vary, as do mismatch probe signal intensities. This might occasionally cause some difficulties in interpretation, particularly with heterozygous genomic samples, in which wild type and mutant sequences are present in equal amounts and hybridize with similar intensity to their array complements, or with insertion and deletion mutations.

Figures 19A, 19B, 19C, 19D:
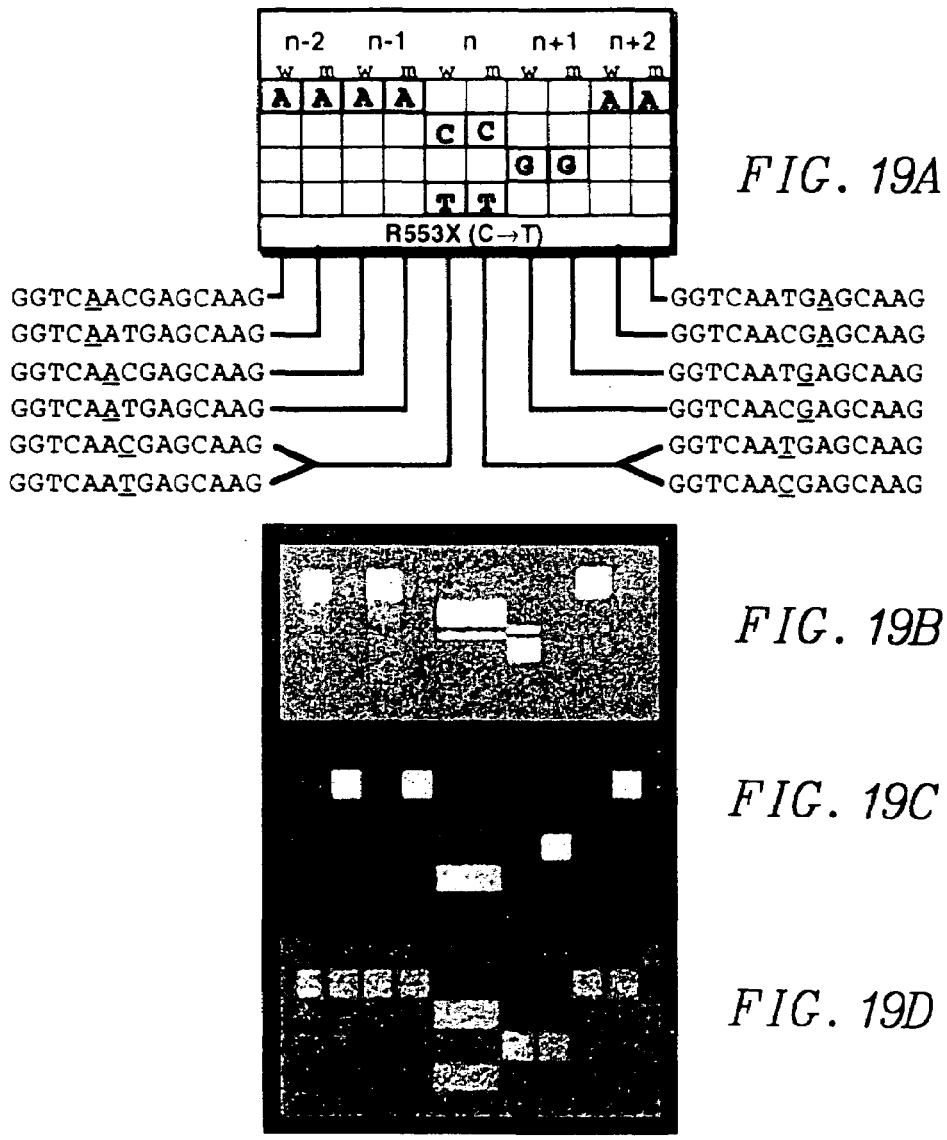
FIG. 19A: Probe array specific for the R553X mutation. w=wild type probes, m=mutant probes, n=mutation position.
FIG. 19B: fluorescence image of R553X array to wildtype target. Brightest signals correspond to shaded features in the "w" column (FIG. 19A), except in the "n" position where the probes complementary to C in both the "w" and "m" columns are bright.
FIG. 19C: Fluorescence image of a R553X array to an R553X mutant target sequence. Signals correspond to shaded features in the "m" columns (FIG. 19A), except in the "n" position where the probes complementary to T in both the "w" and "m" columns are bright.
FIG. 19D: fluorescence image of a hybridization with both wild type and R553X mutant oligonucleotide targets. Brightest signals correspond to the full set of shaded features in FIG. 19A. Note that at the "n" position, the probes complementary to both C and T are bright in both the "w" and "m" columns.

To address these problems a chip containing multiple specialized, compact tiling subarrays each specific for a different CFTR mutations was constructed. This array contains 1480 probes grouped into 37 mutation-specific subarrays of probes laid out as shown in FIG. 19A. The 14 and 15-mer nucleotide probes in these subarrays require 49 photolysis/chemical coupling steps for synthesis. In each subarray, probes are arranged into 10 columns. Columns 1, 3, 5, 7, and 9 contain probes tiled based on the wildtype sequence. Each column contains one perfectly matched probe, and three mismatched probes differing from the perfectly matched probe at an interrogation position. The interrogation position shifts by one nucleotide between columns. Columns 2, 4, 6, 8, and 10 contain probes similarly tiled except based on the mutant sequence. All probes in both tilings have a common 3' end.

Initially, each mutation-specific subarray was hybridized with fluorescein-labeled oligonucleotide targets to test the quality of discrimination between wild type and mutant CFTR sequences. FIGS. 19B-D show typical results from hybridizing oligonucleotide targets complementary to the wild type or mutant sequence or an equal mixture of both to a subarray specific for the exon 11 R553X (C→T) point mutation. Three fluorescence images are aligned with a diagram (FIG. 19A) of the array features and probe sequences diagnostic for these hybridization targets.

The wildtype and mutant tilings in FIG. 19A are interdigitated in 5 pairs of columns (n−2, n−1, n, n+1, n+2) and interrogate five target nucleotide positions. Shaded elements in the diagram indicate probes that are perfectly complementary with the wild type and mutant target sequences. Sequences listed below the diagram match shaded features. Respective probes in each pair of columns differ only at the mutant base (C→T). The four probes occupying each vertical column differ only by A, C, G, or T in the underlined interrogation position. There are two shaded features in each central column, one complementary to the wild type sequence and one to the mutant sequence.

The wild type oligonucleotide target (SEQ. ID. No. 233) (5'TGAGTGGAGGTCAACGAGCAAGA3') hybridizes to perfectly matched probes in five alternating columns (1, 3, 5, 7, 9) (FIG. 19B). The probes in the paired central columns, designated "n", interrogate the mutation position in the target. Because corresponding probes in these two columns are identical, hybridization results in a "doublet" in the center columns giving a total of six hybridized features for homozygous samples.

The relative fluorescence intensity range for perfect matches was 92-100 (mean=96). The highest mismatch intensity range was 22-33 (mean=25). To call a target nucleotide, perfectly complementary probes were required to have a fluorescence intensity at least 1.3 times as high as the second brightest feature in the same column. In addition, the average intensity of signals interpreted as perfected matches was required to be at least twice as high as the average of signals interpreted as single-base mismatches.

Hybridization with the mutant oligonucleotide (SEQ. ID. No. 234) (5' TGAGTGGAGGTCAATGAGCAAGA 3') target shown in FIG. 19C has two key differences from the wild type image in FIG. 19B. First, the hybridized features occur in probe columns offset by one (2, 4, 6, 8, 10) from those hybridized by the wild type target. Second, the central doublet occurs with the probes complementary to the mutant sequence (T), confirming the C to T base change in the mutant target. The relative fluorescence intensity range for perfect matches was 331-373 (mean=351). The highest mismatch intensity range was 83-121 (mean=96).

When both oligonucleotide targets were hybridized together, the heterozygous pattern shown in FIG. 19D resulted. The pattern of twelve hybridized features is the sum of the wild type and mutant hybridization patterns shown in FIGS. 19B and 25C. There is a positive feature in every column of the array plus two in each center ("n") column. In contrast to the basic tiled probe arrays in which sequence assignment is made on the basis of a single set of four probes, hybridization to specialized arrays is assessed with a total of forty probes, permitting a much more accurate genotype assignment. The relative fluorescence intensity range for perfect matches was 123-150 (mean=137). The highest mismatch intensity range was 30-41 (mean=36). The criteria for calling a heterozygote required that the averaged highest signals in columns 1, 3, 5, 7 and 9 agree with the averaged highest signals in columns 2, 4, 6, 8 and 10 within 40%.

(d) Genomic DNA Hybridizations to Block Tiling Arrays

FIG. 20 shows hybridization of fluorescein-labeled, single-stranded DNA targets generated from two different mutant genomic DNA samples to mutation-specific probe arrays. One sample was compound heterozygous for G480C (GT) in exon 10 and G551D (GA) in exon 11. The other was homozygous for ΔF508. Wild type and mutant target sequences are as follows (SEQ. ID. Nos. 235-238):

```
Wild Type:    5'GTGGAGGTCAACGA 3'
G551D:        5'GTGGAGATCAACGT 3'
Wild Type:    5'TCAGAGGGTAAAAT 3'
G480C:        5'TCAGAGTGTAAAAT 3'
```

The underlined sequences are those readable from the chip and the mutation (n) positions are shown in bold. In both cases, exon 10 and 11 targets were prepared in duplex PCR reactions and hybridized simultaneously.

FIG. 20A shows probe sets specific for the G480C and G551D mutations along with diagrams showing the expected heterozygote hybridization patterns. Both G551D and G480C subarrays have all of the expected elements of the heterozygous pattern noted above. Thirteen of the other subarrays on the chip were designed to hybridize with exon 10 and exon 11 targets, and all displayed wildtype hybridization patterns. The relative fluorescence intensity range for this image was 9-2410. As in FIG. 18, low intensity fluorescent signals due to labeled target hybridization to mismatched probes were evident at various locations within the array. In particular, hybridization with the C probes in the "n" column of the G480C array was evident. This was interpreted as mismatch hybridization because there were no confirmatory hybridizations in the remaining eight columns of probes. Low intensity hybridization signals in the n column without confirmatory signals in other columns are discarded during data analysis.

The image of the homozygous ΔF508 target hybridization in FIG. 20B shows some interesting contrasts to the heterozygote hybridization image in FIG. 20A. A diagram of the ΔF508 subarray beside the image indicates the relative positions of perfectly complementary probes. Relevant wildtype and mutant target sequences are as follow:

```
Wild Type       5' AAATATCATCTTTGGTGTT 3'
(SEQ. ID.
No. 239):

ΔF508:          5' AAATATCATctTTGGTGTT 3'

ΔF507:          5' AAATATcatCTTTGGTGTT 3'
```

```
F508C           5' AAATATCATCTGTGGTGTT 3'
(SEQ. ID.
No. 240):
```

Underlined bases are those read from the subarrays and deletions are in lower case letters. Unlike subarrays for base substitution mutations, those for insertion and deletion mutations do not contain common wild type and mutant probes at the "n" position; therefore no hybridization doublets occur. Instead, single positive features in each of five alternating mutant probe columns (2, 4, 6, 8, 10) characterize a ΔF508 homozygous mutant sample. A full set of ten features, one per column, characterizes a ΔF508 heterozygous target.

Another important aspect of this homozygous deletion mutant hybridization is the absence of hybridization patterns in the ΔI507 and F508C probe sets. As shown in FIG. 20A, full length exon 10 and 11 amplicon targets are expected to give informative hybridization patterns with 15 mutation specific probe sets. Although full-length exon 10/exon 11 targets were used in this experiment, the ΔF508 deletion, the ΔI507 deletion, and the F508C polymorphism all occur within the space of a six nucleotide sequence. Therefore, probe sets complementary to these targets overlap significantly. As a result, the ΔI507 and F508C sets do not contain any probes that are fully complementary with a ΔF508 target and a homozygous ΔF508 target will not hybridize significantly with any probes in these sets. This information can be used during data analysis to confirm the homozygous ΔF508 mutant assignment.

(e) Unknown Patient Samples

Ten genomic samples provided by Children's Hospital of Oakland (CHO) were analyzed in the CHO molecular genetics laboratory with a PCR-restriction enzyme digestion protocol and assigned a CFTR genotype. The analysis was then repeated with blinded samples using the specialized mutant-specific chip described above. Fluorescent CFTR exon 10/exon 11 hybridization targets were prepared in duplexed PCR reactions. Each duplex amplification product was hybridized to a separate probe array. The hybridized arrays were scanned and the images analyzed.

The following genotype assignments were made: Four samples had no exon 10 or exon 11 mutations; two samples had single exon 11 mutations, three samples had the ΔF508 mutation in exon 10 and a mutation in exon 11 and one sample had two exon 11 mutations. The results are summarized in Table 5. All assignment were in agreement with those provided by CHO.

Figure 21:
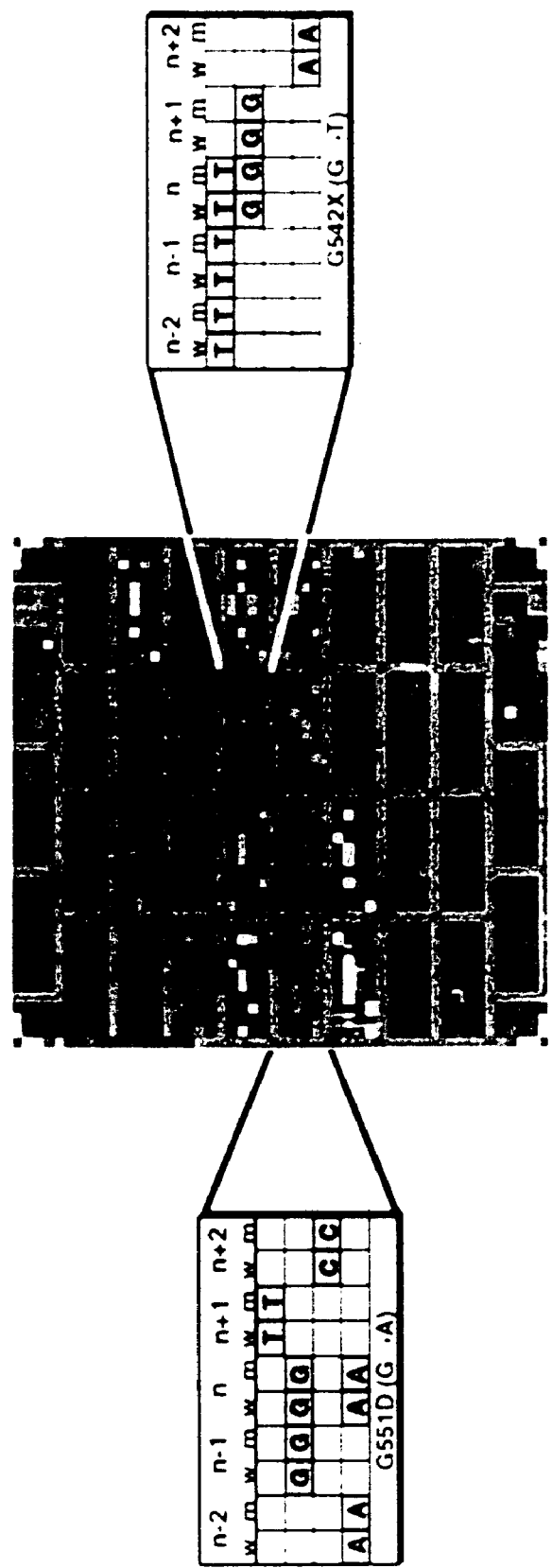
FIG. 21: Image of a specialized mutation specific array hybridized with exon 10 /exon 11 targets prepared from a compound heterozygote for exon 11 mutations G542X and G551D (Children's Hospital of Oakland sample 9). The expected hybridization patterns for these two mutations are diagrammed to the sides of the image. Each of the fifteen arrays specific for exon 10 and exon 11 mutations except G542X and G551D displayed homozygous wild type hybridization patterns. Relative fluorescence intensity range for this image=0-2667.

FIG. 21 shows a typical image from this experiment made from CHO sample nine which had two exon 11 mutations, G542X and G551D. The mutation specific probe sets for these two mutations are indicated and the hybridization patterns are diagrammed. Wild type and mutant sequences are as follow (SEQ. ID. Nos. 241-244):

```
Wild Type:    5' TAGTTCTTGGAGAAGGT 3'
G542X:        5' TAGTTCTTTGAGAAGGT 3'
Wild Type:    5' GAGTGGAGGTCAACGAG 3'
G551D:        5' GAGTGGAGATCAACGAG 3'
```

Bases read from the arrays are underlined and the mutation (n) positions are in bold. Hybridization in both mutation arrays was typical of heterozygous samples, and similar to the examples shown in FIGS. 19D and 20A.

TABLE 5

Results From Unknown Patient Sample CF Genotyping

| Sample | Exon 10 Genotype | Exon 11 Genotype |
| --- | --- | --- |
| CHO 1 | Wild Type | Wild Type |
| CHO 2 | ΔF508 | G542X |
| CHO 3 | Wild Type | Wild Type |
| CHO 4 | Wild Type | Wild Type |
| CHO 5 | ΔF508 | G551D |
| CHO 6 | Wild Type | R553X |
| CHO 7 | Wild Type | G542X |
| CHO 8 | ΔF508 | R553X |
| CHO 9 | Wild Type | G542X/G551D |
| CHO 10 | Wild Type | Wild Type |

(f) The CF745 Chip

The CF745 chip contains probes on a 2"×3" substrate. The cell size is 96 μm×93 μm. The chip contains two subarrays of probes for each of 64 mutations. The upper left zone has 64 subarrays tiled based on coding strand sequences, grouped 5' to 3' following the exon arrangement of the gene. The upper right zone is a 5' to 3' arrangement of subarrays with probes for the same 64 mutations tiled on the non-coding strand. Each subarray of probes is based on the same design as in the 37 mutation chip, except that an eleventh column is present containing control probes. The chip has been hybridized to a multiplex of exons 4, 10, 11, 20 and 21 from genomic DNA. This combination covers 31/64 (48%) of mutations on the chip and accounts for approximately 90% of all mutations.

III. Modes of Practicing the Invention

A. VLSIPS™ Technology

Figure 22:
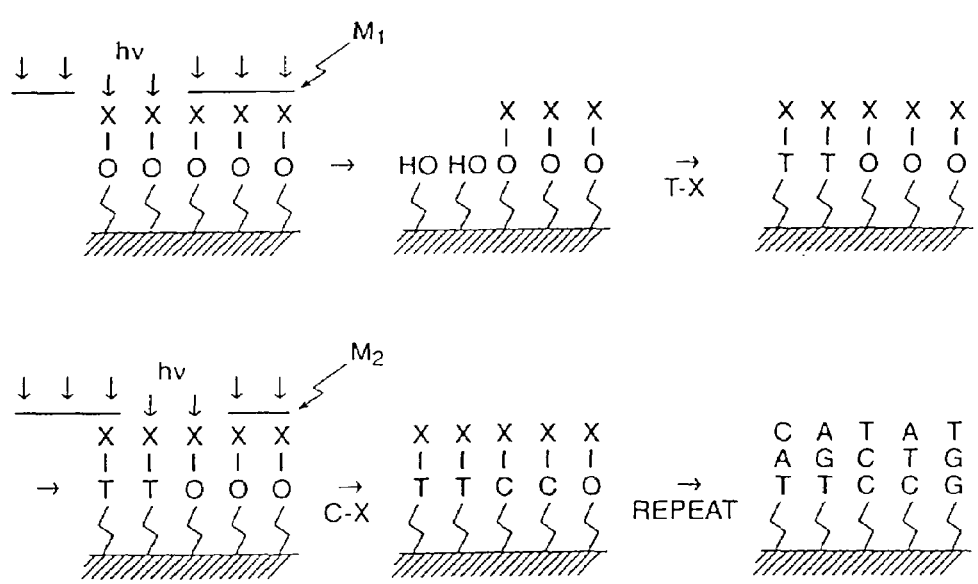
FIG. 22: VLSIPS™ technology applied to the light directed synthesis of oligonucleotides. Light (hv) is shone through a mask ($M_1$) to activate functional groups (—OH) on a surface by removal of a protecting group (X). Nucleoside building blocks protected with photoremovable protecting groups (T-X, C-X) are coupled to the activated areas. By repeating the irradiation and coupling steps, very complex arrays of oligonucleotides can be prepared.
Figure 23:
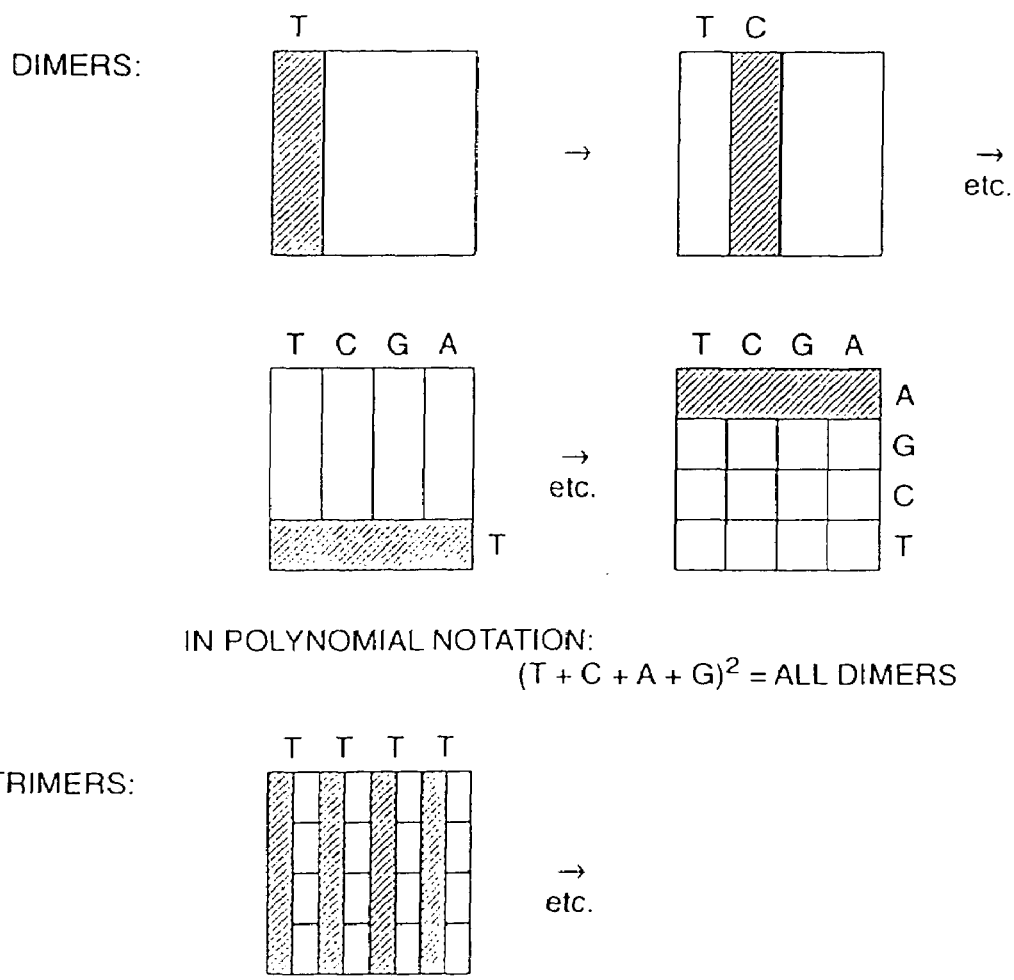
FIG. 23: Use of the VLSIPS™ process to prepare "nucleoside combinatorials" or oligonucleotides synthesized by coupling all four nucleosides to form dimers, trimers, and so forth.

As noted above, the VLSIPSυ technology is described in a number of patent publications and is preferred for making the oligonucleotide arrays of the invention. A brief description of how this technology can be used to make and screen DNA chips is provided in this Example and the accompanying Figures. In the VLSIPS™ method, light is shone through a mask to activate functional (for oligonucleotides, typically an —OH) groups protected with a photoremovable protecting group on a surface of a solid support. After light activation, a nucleoside building block, itself protected with a photoremovable protecting group (at the 5'—OH), is coupled to the activated areas of the support. The process can be repeated, using different masks or mask orientations and building blocks, to prepare very dense arrays of many different oligonucleotide probes. The process is illustrated in FIG. 22; FIG. 23 illustrates how the process can be used to prepare "nucleoside combinatorials" or oligonucleotides synthesized by coupling all four nucleosides to form dimers, trimers and so forth.

New methods for the combinatorial chemical synthesis of peptide, polycarbamate, and oligonucleotide arrays have recently been reported (see Fodor et al., 1991, Science 251: 767-773; Cho et al., 1993, Science 261: 1303-1305; and Southern et al., 1992, Genomics 13: 1008-10017, each of which is incorporated herein by reference). These arrays, or biological chips (see Fodor et al., 1993, Nature 364: 555-556, incorporated herein by reference), harbor specific chemical compounds at precise locations in a high-density, information rich format, and are a powerful tool for the study of biological recognition processes. A particularly exciting application of the array technology is in the field of DNA sequence analysis. The hybridization pattern of a DNA target to an array of shorter oligonucleotide probes is used to gain primary structure information of the DNA target. This format has important applications in sequencing by hybridization, DNA diagnostics and in elucidating the thermodynamic parameters affecting nucleic acid recognition.

Conventional DNA sequencing technology is a laborious procedure requiring electrophoretic size separation of labeled DNA fragments. An alternative approach, termed Sequencing By Hybridization (SBH), has been proposed (Lysov et al., 1988, Dokl. Akad. Nauk SSSR 303:1508-1511; Bains et al., 1988, J. Theor. Biol. 135:303-307; and Drmanac et al., 1989, Genomics 4:114-128, incorporated herein by reference and discussed in Description of Related Art, supra). This method uses a set of short oligonucleotide probes of defined sequence to search for complementary sequences on a longer target strand of DNA. The hybridization pattern is used to reconstruct the target DNA sequence. It is envisioned that hybridization analysis of large numbers of probes can be used to sequence long stretches of DNA. In immediate applications of this methodology, a small number of probes can be used to interrogate local DNA sequence. The strategy of SBH can be illustrated by the following example. A 12-mer target DNA sequence, AGCCTAGCTGAA (SEQ. ID. No. 245), is mixed with a complete set of octanucleotide probes. If only perfect complementarity is considered, five of the 65,536 octamer probes—TCGGATCG, CGGATCGA, GGATCGAC, GATC-GACT, and ATCGACTT will hybridize to the target. Alignment of the overlapping sequences from the hybridizing probes reconstructs the complement of the original 12-mer target:

TCGGATCG

CGGATCGA

GGATCGAC

GATCGACT

ATCGACTT

TCGGATCGACTT (SEQ. ID. No. 123)

Hybridization methodology can be carried out by attaching target DNA to a surface. The target is interrogated with a set of oligonucleotide probes, one at a time (see Strezoska et al., 1991, Proc. Natl. Acad. Sci. USA 88:10089-10093, and Drmanac et al., 1993, Science 260:1649-1652, each of which is incorporated herein by reference). This approach can be implemented with well established methods of immobilization and hybridization detection, but involves a large number of manipulations. For example, to probe a sequence utilizing a full set of octanucleotides, tens of thousands of hybridization reactions must be performed. Alternatively, SBH can be carried out by attaching probes to a surface in an array format where the identity of the probes at each site is known. The target DNA is then added to the array of probes. The hybridization pattern determined in a single experiment directly reveals the identity of all complementary probes.

As noted above, a preferred method of oligonucleotide probe array synthesis involves the use of light to direct the synthesis of oligonucleotide probes in high-density, miniaturized arrays. Photolabile 5'-protected N-acyl-deoxynucleoside phosphoramidites, surface linker chemistry, and versatile combinatorial synthesis strategies have been developed for this technology. Matrices of spatially-defined oligonucleotide probes have been generated, and the ability to use these arrays to identify complementary sequences has been demonstrated by hybridizing fluorescent labeled oligonucleotides to the DNA chips produced by the methods. The hybridization pattern demonstrates a high degree of base specificity and reveals the sequence of oligonucleotide targets.

The basic strategy for light-directed oligonucleotide synthesis (1) is outlined in FIG. 22. The surface of a solid support modified with photolabile protecting groups (X) is illuminated through a photolithographic mask, yielding reactive hydroxyl groups in the illuminated regions. A 3'-O-phosphoramidite activated deoxynucleoside (protected at the 5'-hydroxyl with a photolabile group) is then presented to the surface and coupling occurs at sites that were exposed to light. Following capping, and oxidation, the substrate is rinsed and the surface illuminated through a second mask, to expose additional hydroxyl groups for coupling. A second 5'-protected, 3'-O-phosphoramidite activated deoxynucleoside is presented to the surface. The selective photodeprotection and coupling cycles are repeated until the desired set of products is obtained.

Light directed chemical synthesis lends itself to highly efficient synthesis strategies which will generate a maximum number of compounds in a minimum number of chemical steps. For example, the complete set of $4^n$ polynucleotides (length n), or any subset of this set can be produced in only 4×n chemical steps. See FIG. 23. The patterns of illumination and the order of chemical reactants ultimately define the products and their locations. Because photolithography is used, the process can be miniaturized to generate high-density arrays of oligonucleotide probes. For an example of the nomenclature useful for describing such arrays, an array containing all possible octanucleotides of dA and dT is written as $(A+T)^8$. Expansion of this polynomial reveals the identity of all 256 octanucleotide probes from AAAAAAAA to TTTTTTTT. A DNA array composed of complete sets of dinucleotides is referred to as having a complexity of 2. The array given by $(A+T+C+G)8$ is the full 65,536 octanucleotide array of complexity four. Computer-aided methods of laying down predesigned arrays of probes using VLSIPS™ technology are described in commonly-assigned co-pending application U.S. Ser. No. 08/249,188, filed May 24, 1994 (incorporated by reference in its entirety for all purposes).

In a variation of the VLSIPSTM methods, multiple copies of an array of probes are synthesized simultaneously. The multiple copies are effectively stacked in a pile during the synthesis process in a manner such that each copy is accessible to irradiation. For example, synthesis can occur through the volume of a slab of polymer gel that is transparent to the source of radiation used to remove photoprotective groups. Suitable polymers are described in U.S. Ser. No. 08/431,196, filed Apr. 27, 1995 (incorporated by reference in its entirety for all purposes). For example, a polymer formed from a 90:10% w/w mixture of acylamide and N-2-aminoethylacrylamide is suitable.

After synthesis, the gel is sliced into thin layers (e.g., with a microtome). Each layer is attached to a glass substrate to constitute a separate chip. Alternatively, a pile can be formed from layers of gel separated by layers of a transparent substance that can be mechanically or chemically removed after synthesis has occurred. Using these methods, up to about 10, 100 or 1000 identical arrays can be synthesized simultaneously.

To carry out hybridization of DNA targets to the probe arrays, the arrays are mounted in a thermostatically controlled hybridization chamber. Fluorescein labeled DNA targets are injected into the chamber and hybridization is allowed to proceed for 5 min to 24 hr. The surface of the matrix is scanned in an epifluorescence microscope (Zeiss Axioscop 20) equipped with photon counting electronics using 50-100 μW of 488 nm excitation from an Argon ion laser (Spectra Physics Model 2020). Measurements may be made with the target solution in contact with the probe matrix or after washing. Photon counts are stored and image files are presented after conversion to an eight bit image format. See FIG. 27.

When hybridizing a DNA target to an oligonucleotide array, $N = Lt-(Lp-1)$ complementary hybrids are expected, where N is the number of hybrids, Lt is the length of the DNA target, and Lp is the length of the oligonucleotide probes on the array. For example, for an 11-mer target hybridized to an octanucleotide array, N=4. Hybridizations with mismatches at positions that are 2 to 3 residues from either end of the probes will generate detectable-signals. Modifying the above expression for N, one arrives at a relationship estimating the number of detectable hybridizations (Nd) for a DNA target of length Lt and an array of complexity C. Assuming an average of 5 positions giving signals above background:
$Nd(1+5(C-1))[Lt-(Lp-1)]$.

Arrays of oligonucleotides can be efficiently generated by light-directed synthesis and can be used to determine the identity of DNA target sequences. Because combinatorial strategies are used, the number of compounds increases exponentially while the number of chemical coupling cycles increases only linearly. For example, synthesizing the complete set of $4^8$ (65,536) octanucleotides will add only four hours to the synthesis for the 16 additional cycles. Furthermore, combinatorial synthesis strategies can be implemented to generate arrays of any desired composition. For example, because the entire set of dodecamers ($4^{12}$) can be produced in 48 photolysis and coupling cycles ($b^n$ compounds requires b×n cycles), any subset of the dodecamers (including any subset of shorter oligonucleotides) can be constructed with the correct lithographic mask design in 48 or fewer chemical coupling steps. In addition, the number of compounds in an array is limited only by the density of synthesis sites and the overall array size. Recent experiments have demonstrated hybridization to probes synthesized in 25 μm sites. At this resolution, the entire set of 65,536 octanucleotides can be placed in an array measuring 0.64 cm square, and the set of 1,048,576 dodecanucleotides requires only a 2.56 cm array.

Genome sequencing projects will ultimately be limited by DNA sequencing technologies. Current sequencing methodologies are highly reliant on complex procedures and require substantial manual effort. Sequencing by hybridization has the potential for transforming many of the manual efforts into more efficient and automated formats. Light-directed synthesis is an efficient means for large scale production of miniaturized arrays for SBH. The oligonucleotide arrays are not limited to primary sequencing applications. Because single base changes cause multiple changes in the hybridization pattern, the oligonucleotide arrays provide powerful means to check the accuracy of previously elucidated DNA sequence, or to scan for changes within a sequence. In the case of octanucleotides, a single base change in the target DNA results in the loss of eight complements, and generates eight new complements. Matching of hybridization patterns may be useful in resolving sequencing ambiguities from standard gel techniques, or for rapidly detecting DNA mutational events. The potentially very high information content of light-directed oligonucleotide arrays will change genetic diagnostic testing. Sequence comparisons of hundreds to thousands of different genes will be assayed simultaneously instead of the current one, or few at a time format. Custom arrays can also be constructed to contain genetic markers for the rapid identification of a wide variety of pathogenic organisms.

Oligonucleotide arrays can also be applied to study the sequence specificity of RNA or protein-DNA interactions. Experiments can be designed to elucidate specificity rules of nonWatson-Crick oligonucleotide structures or to investigate the use of novel synthetic nucleoside analogs for antisense or triple helix applications. Suitably protected RNA monomers may be employed for RNA synthesis. The oligonucleotide arrays should find broad application deducing the thermodynamic and kinetic rules governing formation and stability of oligonucleotide complexes.

Figure 24:
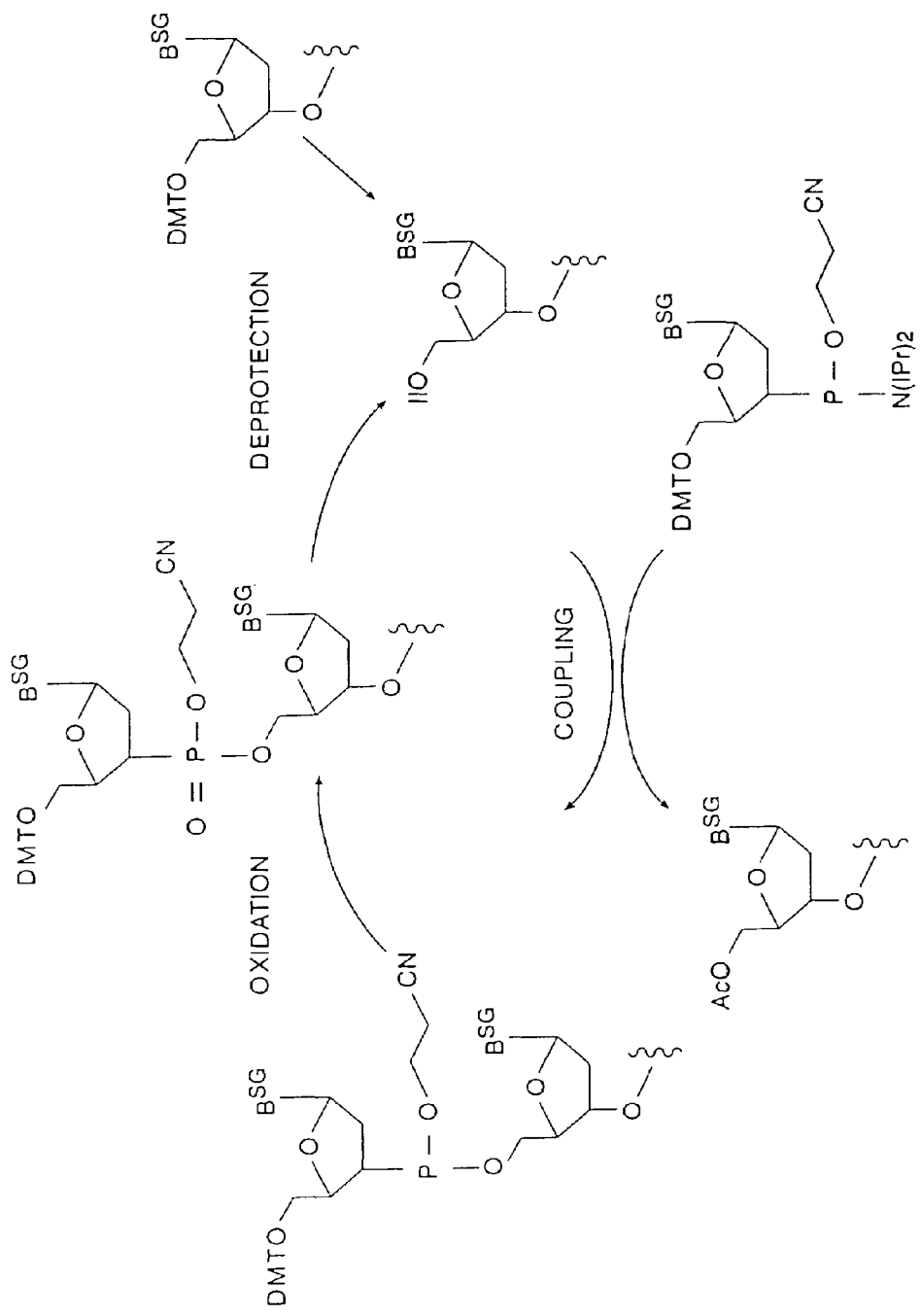
FIG. 24: Deprotection, coupling, and oxidation steps of a solid phase DNA synthesis method.
Figure 25:
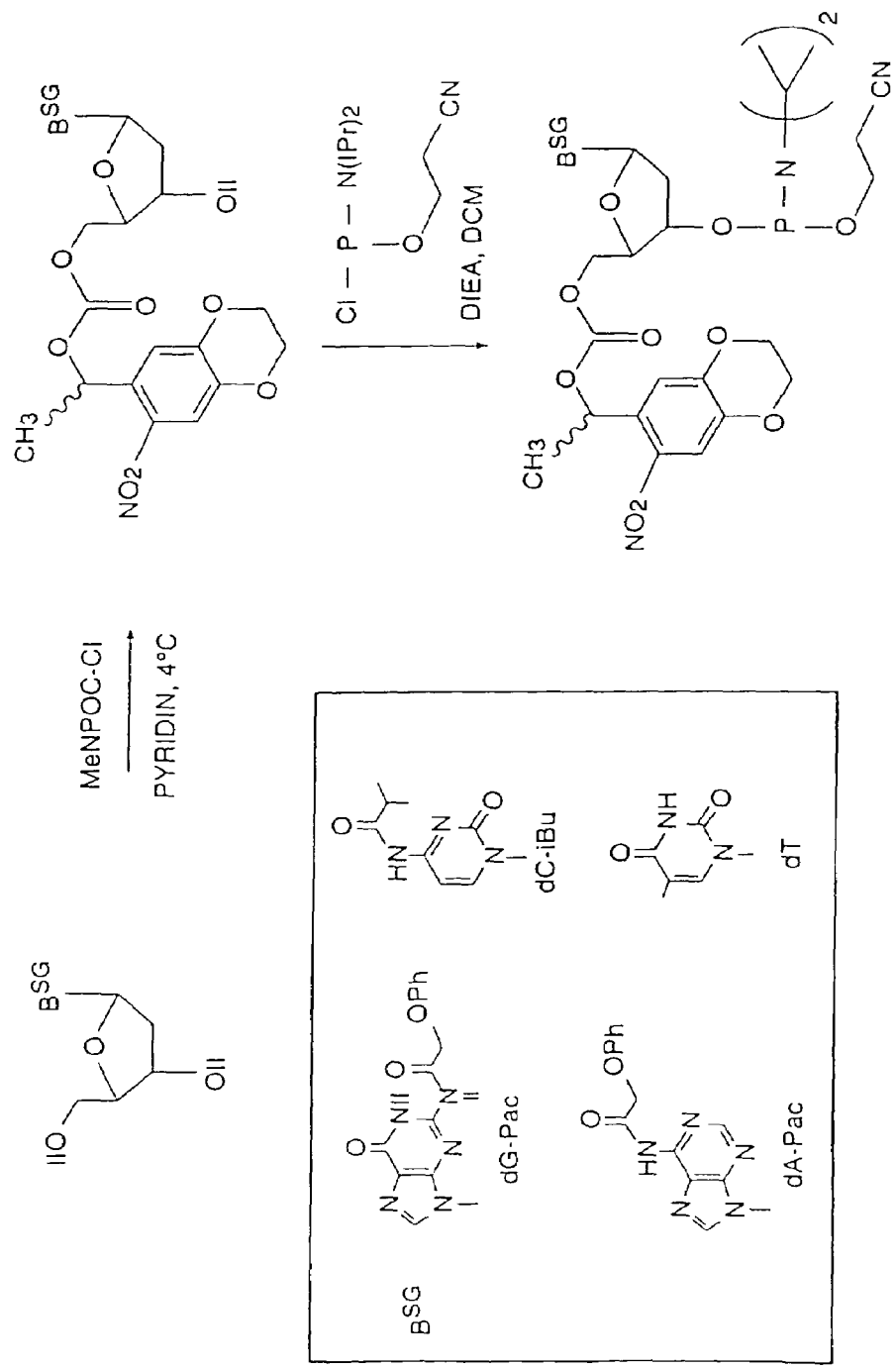
FIG. 25: An illustrative synthesis route for the nucleoside building blocks used in the VLSIPS™ method.
Figure 26:
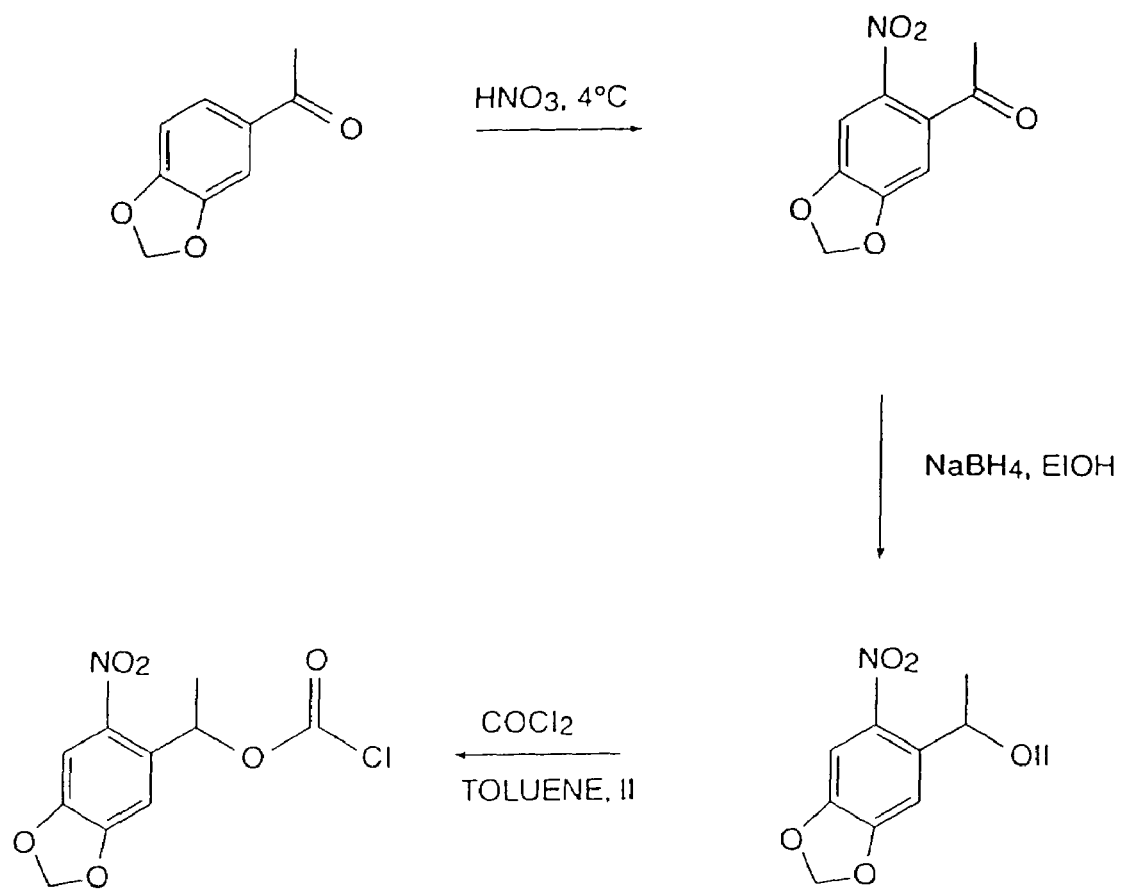
FIG. 26: A preferred photoremovable protecting group, MeNPOC, and preparation of the group in active form.

Other than the use of photoremovable protecting groups, the nucleoside coupling chemistry is very similar to that used routinely today for oligonucleotide synthesis. FIG. 24 shows the deprotection, coupling, and oxidation steps of a solid phase DNA synthesis method. FIG. 25 shows an illustrative synthesis route for the nucleoside building blocks used in the method. FIG. 26 shows a preferred photoremovable protecting group, MeNPOC, and how to prepare the group in active form. The procedures described below show how to prepare these reagents. The nucleoside building blocks are 5'-MeNPOC-THYMIDINE-3'-OCEP; 5'-MeNPOC-N$^4$-t-BUTYL PHENOXYACETYL-DEOXYCYTIDINE-3'-OCEP; 5'-MeNPOC-N$^4$-t-BUTYL PHENOXYACETYL-DEOXYGUANOSINE-3'-OCEP; and 5'-MeNPOC-N$^4$-t-BUTYL PHENOXYACETYL-DEOXYADENOSINE-3'-OCEP.

1. Preparation of 4.5-methylenedioxy-2-nit roacetophenone

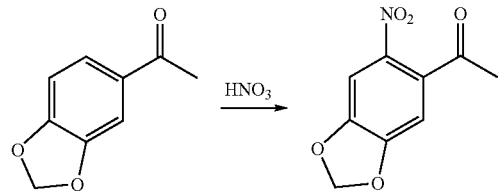

A solution of 50 g (0.305 mole) 3,4-methylenedioxy-acetophenone (Aldrich) in 200 mL glacial acetic acid was added dropwise over 30 minutes to 700 mL of cold (2-4° C.) 70% HNO$_3$ with stirring (NOTE: the reaction will overheat without external cooling from an ice bath, which can be dangerous and lead to side products). At temperatures below 0° C., however, the reaction can be sluggish. A temperature of 3-5° C. seems to be optimal). The mixture was left stirring for another 60 minutes at 3-5° C., and then allowed to approach ambient temperature. Analysis by TLC (25% EtOAc in hexane) indicated complete conversion of the starting material within 1-2 hr. When the reaction was complete, the mixture was poured into ~3 liters of crushed ice, and the resulting yellow solid was filtered off, washed with water and then suction-dried. Yield ~53 g (84%), used without further purification.

2. Preparation of 1-(4.5-Methylenedioxy-2-nitrophenyl) ethanol

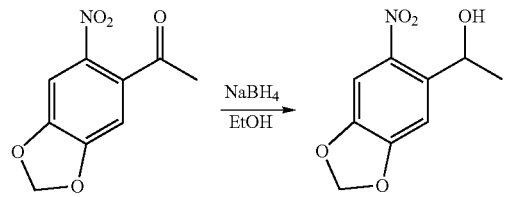

Sodium borohydride (10 g; 0.27 mol) was added slowly to a cold, stirring suspension of 53 g (0.25 mol) of 4,5-methylenedioxy-2-nitroacetophenone in 400 mL methanol. The temperature was kept below 10° C. by slow addition of the NaBH$_4$ and external cooling with an ice bath. Stirring was continued at ambient temperature for another two hours, at which time TLC (CH$_2$Cl$_2$) indicated complete conversion of the ketone. The mixture was poured into one liter of ice-water and the resulting suspension was neutralized with ammonium chloride and then extracted three times with 400 mL CH$_2$Cl$_2$ or EtOAc (the product can be collected by filtration and washed at this point, but it is somewhat soluble in water and this results in a yield of only ~60%). The combined organic extracts were washed with brine, then dried with MgSO$_4$ and evaporated. The crude product was purified from the main byproduct by dissolving it in a minimum volume of CH$_2$Cl$_2$ or THF (~175 ml) and then precipitating it by slowly adding hexane (1000 ml) while stirring (yield 51 g; 80% overall). It can also be recrystallized (e.g., toluene-hexane), but this reduces the yield.

3. Preparation of 1-(4.5-methylenedioxy-2-nitrophenyl) ethyl chloroformate (MeNPOC-Cl)

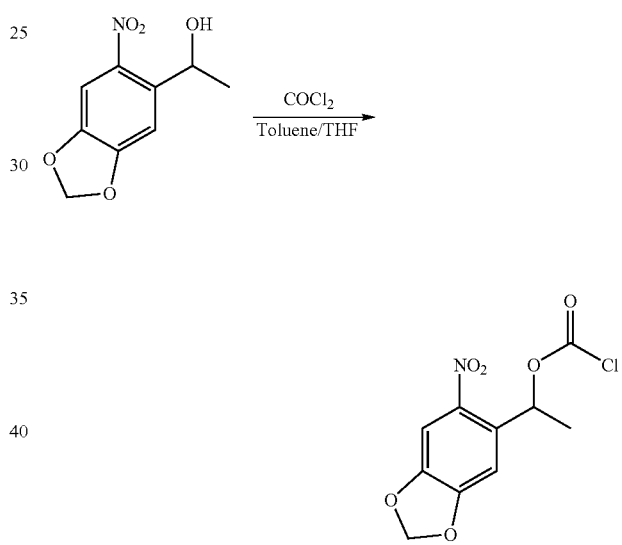

Phosgene (500 mL of 20% w/v in toluene from Fluka: 965 mmole; 4 eq.) was added slowly to a cold, stirring solution of 50 g (237 mmole; 1 eq.) of 1-(4,5-methylenedioxy-2-nitrophenyl) ethanol in 400 mL dry THF. The solution was stirred overnight at ambient temperature at which point TLC (20% Et$_2$O/hexane) indicated >95% conversion. The mixture was evaporated (an oil-less pump with downstream aqueous NaOH trap is recommended to remove the excess phosgene) to afford a viscous brown oil. Purification was effected by flash chromatography on a short (9×13 cm) column of silica gel eluted with 20% Et$_2$O/hexane. Typically 55 g (85%) of the solid yellow MeNPOC-Cl is obtained by this procedure. The crude material has also been recrystallized in 2-3 crops from 1:1 ether/hexane. On this scale, ~100 is used for the first crop, with a few percent THF added to aid dissolution, and then cooling overnight at −20° C. (this procedure has not been optimized). The product should be stored desiccated at −20° C.

4. Synthesis of 5'- Menpoc-2'-deoxynucleoside-3'-(N,N-diisopropyl 2-cyanoethyl phosphoramidites (a.) 5'-MeNPOC-Nucleosides

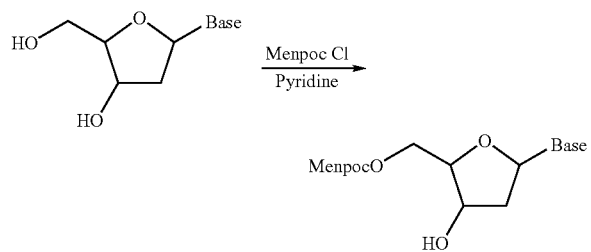

Base=THYMIDINE (T); N-4-ISOBUTYRYL 2'-DEOXY-CYTIDINE (ibu-dC); N-2-PHENOXYACETYL 2'DEOXYGUANOSINE (PAC-dG); and N-6-PHENOXYACETYL 2'DEOXYADENOSINE (PAC-dA)

All four of the 5'-MeNPOC nucleosides were prepared from the base-protected 2'-deoxynucleosides by the following procedure. The protected 2'-deoxynucleoside (90 mmole) was dried by co-evaporating twice with 250 mL anhydrous pyridine. The nucleoside was then dissolved in 300 mL anhydrous pyridine (or 1:1 pyridine/DMF, for the dG$^{PAC}$ nucleoside) under argon and cooled to ~2° C. in an ice bath. A solution of 24.6 g (90 mmole) MeNPOC-Cl in 100 mL dry THF was then added with stirring over 30 minutes. The ice bath was removed, and the solution allowed to stir overnight at room temperature (TLC: 5-10% MeOH in CH$_2$Cl$_2$; two diastereomers) After evaporating the solvents under vacuum, the crude material was taken up in 250 mL ethyl acetate and extracted with saturated aqueous NaHCO$_3$ and brine. The organic phase was then dried over Na$_2$SO$_4$, filtered and evaporated to obtain a yellow foam. The crude products were finally purified by flash chromatography (9×30 cm silica gel column eluted with a stepped gradient of 2%-6% MeOH in CH$_2$Cl$_2$). Yields of the purified diastereomeric mixtures are in the range of 65-75%.

(b.) 5'- Menpoc-2'-deoxynucleoside-3'-(N,N-diisopropyl 2-cyanoethyl phosphoramidites)

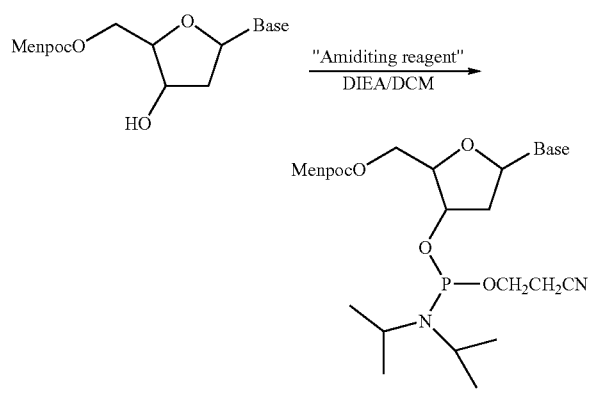

The four deoxynucleosides were phosphitylated using either 2-cyanoethyl-N,N-diisopropyl chlorophosphoramidite, or 2-cyanoethyl-N,N,N',N'-tetraisopropylphosphorodiamidite.

The following is a typical procedure. Add 16.6 g (17.4 ml; 55 mmole) of 2-cyanoethyl-N,N,N',N'-tetraisopropylphosphoro-diamidite to a solution of 50 mmole 5'- MeNPOC-nucleoside and 4.3 g (25 mmole) diisopropylammonium tetrazolide in 250 mL dry CH$_2$Cl$_2$ under argon at ambient temperature. Continue stirring for 4-16 hours (reaction monitored by TLC: 45:45:10 hexane/CH$_2$Cl$_2$/Et$_3$N). Wash the organic phase with saturated aqueous NaHCO$_3$ and brine, then dry over Na$_2$SO$_4$, and evaporate to dryness. Purify the crude amidite by flash chromatography (9×25 cm silica gel column eluted with hexane/CH$_2$Cl$_2$/TEA-45:45:10 for A, C, T; or 0:90:10 for G). The yield of purified amidite is about 90%.

B. Preparation of Labeled DNA/Hybridization to Array

1. PCR

PCR amplification reactions are typically conducted in a mixture composed of, per reaction: 1 µl genomic DNA; 10 µl each primer (10 pmol/µl stocks); 10 µl 10×PCR buffer (100 mM Tris.Cl pH 8.5, 500 mM KCl, 15 mM MgCl$_2$); 10 µl 2 mM dNTPs (made from 100 mM dNTP stocks); 2.5 U Taq polymerase (Perkin Elmer AmpliTaq™, 5 U/µl); and H$_2$O to 100 µl. The cycling conditions are usually 40 cycles (94° C. 45 sec, 55° C. 30 sec, 72° C. 60 sec) but may need to be varied considerably from sample type to sample type. These conditions are for 0.2 mL thin wall tubes in a Perkin Elmer 9600 thermocycler. See Perkin Elmer 1992/93 catalogue for 9600 cycle time information. Target, primer length and sequence composition, among other factors, may also affect parameters.

For products in the 200 to 1000 bp size range, check 2 µl of the reaction on a 1.5% 0.5×TBE agarose gel using an appropriate size standard (phiX174 cut with HaeIII is convenient). The PCR reaction should yield several picomoles of product. It is helpful to include a negative control (i.e., 1 µl TE instead of genomic DNA) to check for possible contamination. To avoid contamination, keep PCR products from previous experiments away from later reactions, using filter tips as appropriate. Using a set of working solutions and storing master solutions separately is helpful, so long as one does not contaminate the master stock solutions.

For simple amplifications of short fragments from genomic DNA it is, in general, unnecessary to optimize Mg$^{2+}$ concentrations. A good procedure is the following: make a master mix minus enzyme; dispense the genomic DNA samples to individual tubes or reaction wells; add enzyme to the master mix; and mix and dispense the master solution to each well, using a new filter tip each time.

2. Purification

Removal of unincorporated nucleotides and primers from PCR samples can be accomplished using the Promega Magic PCR Preps DNA purification kit. One can purify the whole sample, following the instructions supplied with the kit (proceed from section IIIB, 'Sample preparation for direct purification from PCR reactions'). After elution of the PCR product in 50 µl of TE or H$_2$O, one centrifuges the eluate for 20 sec at 12,000 rpm in a microfuge and carefully transfers 45 µl to a new microfuge tube, avoiding any visible pellet. Resin is sometimes carried over during the elution step. This transfer prevents accidental contamination of the linear amplification reaction with 'Magic PCR' resin. Other methods, e.g., size exclusion chromatography, may also be used.

3. Linear Amplification

In a 0.2 mL thin-wall PCR tube mix: 4 µl purified PCR product; 2 µl primer (10 pmol/µl); 4 µl 10×PCR buffer; 4 µl dNTPs (2 mM dA, dC, dG, 0.1 mM dT); 4 µl 0.1 mM dUTP; 1 µl 1 mM fluorescein dUTP (Amersham RPN 2121); 1 U Taq polymerase (Perkin Elmer, 5 U/μl); and add H2O to 40 μl. Conduct 40 cycles (92° C. 30 sec, 55° C. 30 sec, 72° C. 90 sec) of PCR. These conditions have been used to amplify a 300 nucleotide mitochondrial DNA fragment but are applicable to other fragments. Even in the absence of a visible product band on an agarose gel, there should still be enough product to give an easily detectable hybridization signal. If one is not treating the DNA with uracil DNA glycosylase (see Section 4), dUTP can be omitted from the reaction.

4. Fragmentation

Purify the linear amplification product using the Promega Magic PCR Preps DNA purification kit, as per Section 2 above. In a 0.2 mL thin-wall PCR tube mix: 40 μl purified labeled DNA; 4 μl 10×PCR buffer; and 0.5 μl uracil DNA glycosylase (BRL 1U/μl ). Incubate the mixture 15 min at 37° C., then 10 min at 97° C.; store at −20° C. until ready to use.

5. Hybridization, Scanning & Stripping

A blank scan of the slide in hybridization buffer only is helpful to check that the slide is ready for use. The buffer is removed from the flow cell and replaced with 1 ml of (fragmented) DNA in hybridization buffer and mixed well.

Optionally, standard hybridization buffer can be supplemented with tetramethylammonium chloride (TMACL) or betaine (N,N,N-trimethylglycine; $(CH_3)_3$ $N+CH_2COO^-$) to improve discrimination between perfectly matched targets and single-base mismatches. Betaine is zwitterionic at neutral pH and alters the composition-dependent stability of nucleic acids without altering their polyelectrolyte behavior. Betaine is preferably used at a concentration between 1 and 10 M and, optimally, at about 5 M. For example, 5 M betaine in 2×SSPE is suitable. Inclusion of betaine at this concentration lowers the average hybridization signal about four fold, but increases the discrimination between matched and mismatched probes.

Figure 27:
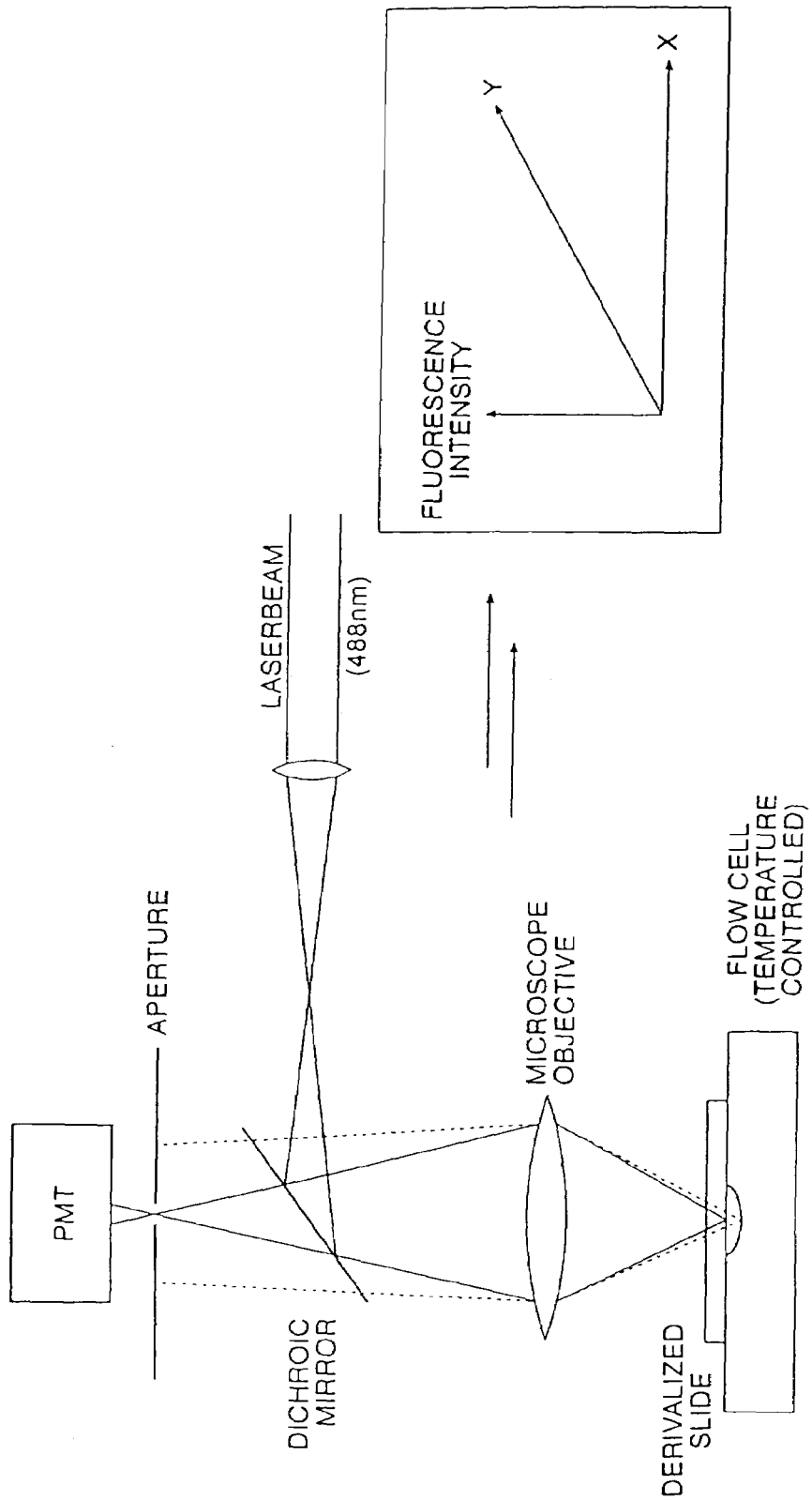
FIG. 27: Detection system for scanning a DNA chip.

The scan is performed in the presence of the labeled target. FIG. 27 illustrates an illustrative detection system for scanning a DNA chip. A series of scans at 30 min intervals using a hybridization temperature of 25° C. yields a very clear signal, usually in at least 30 min to two hours, but it may be desirable to hybridize longer, i.e., overnight. Using a laser power of 50 μW and 50 μm pixels, one should obtain maximum counts in the range of hundreds to low thousands/pixel for a new slide. When finished, the slide can be stripped using 50% formamide. Rinsing well in deionized $H_2O$, blowing dry, and storing at room temperature.

C. Preparation of Labeled RNA/Hybridization to Array

1. Tagged Primers

The primers used to amplify the target nucleic acid should have promoter sequences if one desires to produce RNA from the amplified nucleic acid. Suitable promoter sequences are shown below (SEQ. ID. Nos. 124-127) and include:

```
(1) the T3 promoter sequence:
5'-CGGAATTAACCCTCACTAAAGG

5'-AATTAACCCTCACTAAAGGGAG;

(2) the T7 promoter sequence:
5' TAATACGACTCACTATAGGGAG; and (3) the SP6 promoter sequence:
5' ATTTAGGTGACACTATAGAA.
```

The desired promoter sequence is added to the 5' end of the PCR primer. It is convenient to add a different promoter to each primer of a PCR primer pair so that either strand may be transcribed from a single PCR product.

Synthesize PCR primers so as to leave the DMT group on. DMT-on purification is unnecessary for PCR but appears to be important for transcription. Add 25 μl 0.5M NaOH to collection vial prior to collection of oligonucleotide to keep the DMT group on. Deprotect using standard chemistry—55° C. overnight is convenient.

HPLC purification is accomplished by drying down the oligonucleotides, resuspending in 1 mL 0.1 M TEAA (dilute 2.0 M stock in deionized water, filter through 0.2 micron filter) and filter through 0.2 micron filter. Load 0.5 mL on reverse phase HPLC (column can be a Hamilton PRP-1 semi-prep, #79426). The gradient is 0→50% $CH_3CN$ over 25 min (program 0.2 μmol.prep.0-50, 25 min). Pool the desired fractions, dry down, resuspend in 200 μl 80% HAc. 30 min RT. Add 200 μAl EtOH; dry down. Resuspend in 200 μl $H_2O$, plus 20 μl NaAc pH 5.5, 600 μl EtOH. Leave 10 min on ice; centrifuge 12,000 rpm for 10 min in microfuge. Pour off supernatant. Rinse pellet with 1 mL EtOH, dry, resuspend in 200 μl H2O. Dry, resuspend in 200 μl TE. Measure A260, prepare a 10 pmol/μl solution in TE (10 mM Tris.Cl pH 8.0, 0.1 mM EDTA). Following HPLC purification of a 42 mer, a yield in the vicinity of 15 nmol from a 0.2 μmol scale synthesis is typical.

2. Genomic DNA Preparation

Add 500 μl (10 mM Tris.Cl pH 8.0, 10 mM EDTA, 100 mM NaCl, 2% (w/v) SDS, 40 mM DTT, filter sterilized) to the sample. Add 1.25 μl 20 mg/ml proteinase K (Boehringer) Incubate at 55° C. for 2 hours, vortexing once or twice. Perform 2×0.5 mL 1:1 phenol:$CHCl_3$ extractions. After each extraction, centrifuge 12,000 rpm 5 min in a microfuge and recover 0.4 mL supernatant. Add 35 μl NaAc pH 5.2 plus 1 mL EtOH. Place sample on ice 45 min; then centrifuge 12,000 rpm 30 min, rinse, air dry 30 min, and resuspend in 100 μl TE.

3. PCR

PCR is performed in a mixture containing, per reaction: 1 μl genomic DNA; 4 μl each primer (10 pmol/μl stocks); 4 μl 10×PCR buffer (100 mM Tris.Cl pH 8.5, 500 mM KCl, 15 mM $MgCl_2$); 4 μl 2 mM dNTPs (made from 100 mM dNTP stocks); 1 U Taq polymerase (Perkin Elmer, 5 U/μl); $H_2O$ to 40 μl. About 40 cycles (94° C. 30 sec, 55° C. 30 sec, 72° C. 30 sec) are performed, but cycling conditions may need to be varied. These conditions are for 0.2 mL thin wall tubes in Perkin Elmer 9600. For products in the 200 to 1000 bp size range, check 2 μl of the reaction on a 1.5% 0.5×TBE agarose gel using an appropriate size standard. For larger or smaller volumes (20-100 μl), one can use the same amount of genomic DNA but adjust the other ingredients accordingly.

4. In Vitro Transcription

Mix: 3 μl PCR product; 4 μl 5× buffer; 2 μl DTT; 2.4 μl 10 mM rNTPs (100 mM solutions from Pharmacia); 0.48 μl 10 mM fluorescein-UTP (Fluorescein-12-UTP, 10 mM solution, from Boehringer Mannheim); 0.5 μl RNA polymerase (Promega T3 or T7 RNA polymerase); and add $H_2O$ to 20 μl. Incubate at 37° C. for 3 h. Check 2 μl of the reaction on a 1.5% 0.5×TBE agarose gel using a size standard. 5× buffer is 200 mM Tris pH 7.5, 30 mM $MgCl_2$, 10 mM spermidine, 50 mM NaCl, and 100 mM DTT (supplied with enzyme). The PCR product needs no purification and can be added directly to the transcription mixture. A 20 μl reaction is suggested for an initial test experiment and hybridization; a 100 μl reaction is considered "preparative" scale (the reaction can be scaled up to obtain more target).

The amount of PCR product to add is variable; typically a PCR reaction will yield several picomoles of DNA. If the PCR reaction does not produce that much target, then one should increase the amount of DNA added to the transcription reaction (as well as optimize the PCR). The ratio of fluorescein-UTP to UTP suggested above is 1:5, but ratios from 1:3 to 1:10—all work well. One can also label with biotin-UTP and detect with streptavidin-FITC to obtain similar results as with fluorescein-UTP detection.

For nondenaturing agarose gel electrophoresis of RNA, note that the RNA band will normally migrate somewhat faster than the DNA template band, although sometimes the two bands will comigrate. The temperature of the gel can effect the migration of the RNA band. The RNA produced from in vitro transcription is quite stable and can be stored for months (at least) at −20° C. without any evidence of degradation. It can be stored in unsterilized 6×SSPE 0.1% triton X-100 at −20° C. for days (at least) and reused twice (at least) for hybridization, without taking any special precautions in preparation or during use. RNase contamination should of course be avoided. When extracting RNA from cells, it is preferable to work very rapidly and to use strongly denaturing conditions. Avoid using glassware previously contaminated with RNases. Use of new disposable plasticware (not necessarily sterilized) is preferred, as new plastic tubes, tips, etc., are essentially RNase free. Treatment with DEPC or autoclaving is typically not necessary.

5. Fragmentation

Heat transcription mixture at 94 degrees for forty min. The extent of fragmentation is controlled by varying $Mg^{2+}$ concentration (30 mM is typical), temperature, and duration of heating.

6. Hybridization, Scanning, & Stripping

A blank scan of the slide in hybridization buffer only is helpful to check that the slide is ready for use. The buffer is removed from the flow cell and replaced with 1 mL of (hydrolysed) RNA in hybridization buffer and mixed well. Incubate for 15-30 min at 18° C. Remove the hybridization solution, which can be saved for subsequent experiments. Rinse the flow cell 4-5 times with fresh changes of 6×SSPE 0.1% Triton X-100, equilibrated to 18° C. The rinses can be performed rapidly, but it is important to empty the flow cell before each new rinse and to mix the liquid in the cell thoroughly. A series of scans at 30 min intervals using a hybridization temperature of 25° C. yields a very clear signal, usually in at least 30 min to two hours, but it may be desirable to hybridize longer, i.e., overnight. Using a laser power of 50 μW and 50 μm pixels, one should obtain maximum counts in the range of hundreds to low thousands/pixel for a new slide. When finished, the slide can be stripped using warm water.

These conditions are illustrative and assume a probe length of ~15 nucleotides. The stripping conditions suggested are fairly severe, but some signal may remain on the slide if the washing is not stringent. Nevertheless, the counts remaining after the wash should be very low in comparison to the signal in presence of target RNA. In some cases, much gentler stripping conditions are effective. The lower the hybridization temperature and the longer the duration of hybridization, the more difficult it is to strip the slide. Longer targets may be more difficult to strip than shorter targets.

7. Amplification of Signal

A variety of methods can be used to enhance detection of labelled targets bound to a probe on the array. In one embodiment, the protein MutS (from *E. coli*) or equivalent proteins such as yeast MSH1, MSH2, and MSH3; mouse Rep-3, and Streptococcus Hex-A, is used in conjunction with target hybridization to detect probe-target complex that contain mismatched base pairs. The protein, labeled directly or indirectly, can be added to the chip during or after hybridization of target nucleic acid, and differentially binds to homo- and heteroduplex nucleic acid. A wide variety of dyes and other labels can be used for similar purposes. For instance, the dye YOYO-1 is known to bind preferentially to nucleic acids containing sequences comprising runs of 3 or more G residues.

8. Detection of Repeat Sequences

In some circumstances, i.e., target nucleic acids with repeated sequences or with high G/C content, very long probes are sometimes required for optimal detection. In one embodiment for detecting specific sequences in a target nucleic acid with a DNA chip, repeat sequences are detected as follows. The chip comprises probes of length sufficient to extend into the repeat region varying distances from each end. The sample, prior to hybridization, is treated with a labelled oligonucleotide that is complementary to a repeat region but shorter than the full length of the repeat. The target nucleic is labelled with a second, distinct label. After hybridization, the chip is scanned for probes that have bound both the labelled target and the labelled oligonucleotide probe; the presence of such bound probes shows that at least two repeat sequences are present.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

TABLE 3

| Mutation | Exon | Exon size | Pop Freq | Location | Sequence Around Mutation Site (SEQ. ID. Nos. 128-191) | Amp PRIMERS | Sz. |
|---|---|---|---|---|---|---|---|
| 297 − 3C>T | 2 | 109 | Manchester | Sub C>T + 3 Exon 3 | CTTTTTATTC TTTTG(C>T)AGAG AATGGGATAG A | 787/788 | 297 |
| R75Q | 3 | 109 | Manchester | Substitute G>A at 60 | TAATGCCCTT CGGC(G>A)ATGTT TTTTGTGGA | 787/788 | 297 |
| 300 del A | 3 | 109 | Manchester | Delete A at 4 | ATTCTTTTGC AGAGAaTGGG ATAGAGAGCT GGCT | 787/788 | 297 |
| E60X | 3 | 109 | Manchester | Substitute G>T at 14 | GAATGGGATA GA(G>T)AGCTGGC TTCAAAGA | 787/788 | 297 |
| L88S | 3 | 109 | Manchester | Substitute T>C at 99 | CTATGGAATC TTTT(T>C)ATATT TAGGGGTAAG | 787/788 | 297 |
| G86E | 3 | 109 | 0.70% | Substitute G>A at 90 | TTATGTTCTA TG(G>A)AATCTTT TTATATTTAG | 787/788 | 297 |
| R117H | 4 | 216 | 0.80% | Substitute G>A at 77 | AACAAGGAGG AAC(G>A)CTCTAT CGCGATTTAT | 851/769 | 381 |
| R117C | 4 | 216 | rare | Substitute C>T at 76 | AACAAGGAGG AA(C>t)GCTCTAT CGCGATTTAT | 851/769 | 381 |

TABLE 3-continued

| Mutation | Exon | Exon size | Pop Freq | Location | Sequence Around Mutation Site (SEQ. ID. Nos. 128-191) | PRIMERS | Amp Sz. |
|---|---|---|---|---|---|---|---|
| Y122X | 4 | 216 | 0.30% | Substitute T>A at 93 | TATCGCGATT TA(T>A)CTAGGCA TAGGCTTATG | 851/769 | 381 |
| I148T | 4 | 216 | Fr Can (10%) | Substitute T>C at 170 | GGCCTTCATC ACA(T>C)TGGAAT GCAGATGAGA | 851/769 | 381 |
| 621 + 1G>T | 4 | 216 | 1.30% | Sub G>T after last base | GATTTATAAG AAG(G>T)TAATAC TTCCTTGCAC | 851/769 | 381 |
| 711 + 1G>T | 5 | 90 | 0.90% | Sub G>T after last base | CAAATTTGAT GAA(G>t)TATGTA CCTATTGATT | 887/888 | 289 |
| L206W | 6a | 164 | Fr Can (10%) | Substitute T>G at 38 | TGGATCGCTC CTT(T>G)GCAAGT GGCACTCCTC | 934/935 | 331 |
| 1138 ins G | 7 | 247 | Manchester | Insert G at 137 | AATCATCCTC CGGAAAgATA TTCACCACCA TCT | 789/790 | 404 |
| 1154 ins TC | 7 | 247 | Manchester | Insert TC at 153 | TATTCACCAC CATCTCtcAT TCTGCATTGT T | 789/790 | 404 |
| 1161 del C | 7 | 247 | Manchester | Delete C at 160 | CCACCATCTC ATTCTGcATT CTTCTGCGCA TGG | 789/790 | 404 |
| R334W | 7 | 247 | 0.40% | Substitute C>T at 131 | AAGGAATCAT CCTC(C>T)GGAAA ATATTCATTA | 789/790 | 404 |
| R347H | 7 | 247 | 0.10% | Substitute G>A at 171 | CTGCATTGTT CTGC(G>A)CATGG CGGTCACTCG | 789/790 | 404 |
| R347L | 7 | 247 | rare | Substitute G>T at 171 | CTGCATTGTT CTGC(G>T)CATGG CGGTCACTCG | 789/790 | 404 |
| R347P | 7 | 247 | 0.50% | Substitute G>C at 171 | CTGCATTGTT CTGC(G>c)CATGG CGGTCACTCG | 789/790 | 404 |
| 1078 del T | 7 | 247 | 1.10% | Delete T at 77 | CTTCTTCTCA GGGTTCTTGT GGTGTTTTTA TC | 789/790 | 404 |
| 1248 + 1G>A | 7 | 247 | Manchester | Sub G>A1 after Exon 7 | AAACAAAATA CAG(G>A)TAATGT ACCATAATG | 789/790 | 404 |
| A455E | 9 | 183 | 0.40% | Substitute C>A at 155 | AGGACAGTTG TTGG(c>a)GGTTG CTGGATCCA | 891/892 | 386 |
| G480C | 10 | 192 | rare | Substitute G>T at 46 | GGAGCCTTGA CAG(G>T)GTAAAA TTAAGCACA | 760/850 | 304 |
| O493X | 10 | 192 | 0.30% | Substitute C>T at 85 | TCATTCTGTT CT(C>T)AGTTTTC CTGGATTAT | 760/850 | 304 |
| DI507 | 10 | 192 | 0.50% | Delete 126, 127, 128 | ATTAAAGAAA ATATcatCTT TGGTGTTTCC TATG | 760/850 | 304 |
| F508C | 10 | 192 | rare | Substitute T>G at 131 | TAAAGAAAAT ATCATCT(T>g)TG GTGTTTCCTA | 760/850 | 304 |
| DF508 | 10 | 192 | 67.20% | Delete 129, 130, 131 | ATTAAAGAAA ATATCATcTG TGTTTCCTA TG | 760/850 | 304 |
| V520F | 10 | 192 | 0.20% | Substitute G>T at 166 | TAGATACAGA AGC(G>T)TCATCA AAGCATGCC | 760/850 | 304 |
| 1717 − 1G>A | 10 | 95 | 1.10% | Sub G>A at +1 Ex 11 | TATTTTTGGT AATA(G>a)GACAT CTCCAAGTTT | 762/763 | 233 |
| G542X | 11 | 95 | 3.40% | Substitute G>T at 40 | ACAATATAGT TCTT(G>T)GAGAA GGTGGAAT | 762/762 | 233 |
| S549N | 11 | 95 | rare | Substitute G>A at 62 | AGGTGGAATC ACACTGA(G>A)TG GAGGTCAACG | 762/763 | 233 |
| S549I | 11 | 95 | rare | Substitute G>T at 62 | AGGTGAATCA CACTGA(G>T)TGG AGGTCAACG | 762/763 | 233 |
| S549R (A>C) | 11 | 95 | rare | Substitute A>C at 61 | AGGTGGAATC ACACTG(A>c)GTG GAGGTCAACG | 762/763 | 233 |
| S549R (T>G) | 11 | 95 | 0.30% | Substitute T>G at 63 | AGGTGGAATC ACACTGAG(T>G)G GAGGTCAACG | 762/763 | 233 |
| G551D | 11 | 95 | 2.40% | Substitute G>A at 88 | ATCACACTGA GTGGAG(G>A)TCA ACGAGCAAGA | 762/763 | 233 |
| G551S | 11 | 95 | rare | Substitute G>A at 67 | ATCACACTGA GTGGA(G>A)GTCA ACGAGCAAGA | 762/763 | 233 |
| O552X | 11 | 95 | rare | Substitute C>T at 70 | ACACTGAGTG GAGGT(C>T)AACG AGCAAGAATT | 762/763 | 233 |
| R522Q | 11 | 95 | rare | Substitute G>A at 74 | TGAGTGGAGG TCAAC(G>A)AGCA AGAATTTCT | 762/763 | 233 |
| R563X | 11 | 95 | 1.30% | Substitute C>T at 73 | TGAGTGGAGG TCAA(C>t)GAGCA AGAATTTCTTT | 762/763 | 233 |
| A559T | 11 | 95 | rare | Substitute G>A at 91 | GCAAGAATTT CTTTA(G>A)CAAG GTGAATAAC | 762/763 | 233 |
| R560T | 11 | 95 | 0.40% | Substitute G>C at 95 | ATTTCTTTAG CAA(G>C)GTGAAT AACTAA | 762/763 | 233 |
| R560K | 11 | 95 | rare | Substitute G>A at 95 | GAATTTCTTT AGCAA(G>A)GTGA ATAACTAA | 762/763 | 233 |
| 1898 + 1G>A | 12 | 95 | 0.90% | Sub G>A after last Ex 12 | GAAATATTTG AAAG(G>A)TATGT TCTTTGAAT | 931/932 | 299 |

TABLE 3-continued

| Mutation | Exon | Exon size | Pop Freq | Location | Sequence Around Mutation Site (SEQ. ID. Nos. 128-191) | PRIMERS | Amp Sz. |
|---|---|---|---|---|---|---|---|
| D648V | 13 | 724 | Nst Am (63%) | Substitute A>T at 177 | AACTCATGGG ATGTG(A>T)TTCT TTCGACCAAT | 955/884 | 360 |
| 2184 del A | 13 | 724 | 0.70% | Delete A at 286 | GACGAAACAA AAAAaCAATC TTTTAAACAG AC | 955/884 | 360 |
| 2184 ins A | 13 | 724 | rare | Insert A after 286 | GACAGAAACA AAAAAaCAA TCTTTTAAAG CGAC | 955/884 | 360 |
| 2789 + 5G>A | 14b | 38 | 1.10% | Sub G>A 5 one after last | CTCCTTGGAA AGTGA(G>A)TATT CCATGTCCTA | 885/886 | 374 |
| 3272 − 26A>G | 17a | 228 | rare | Sub A>G 26 before 17b | TTTATGTTAT TTGCA(A>G)TGTT TTCTATGGAA A | 782/901 | 414 |
| 3272 − 93T>C | 17a | 228 | rare | Sub T>C 93 before 17b | ATTTGTGATA TGATTA(T>C)TCT AATTTAGTCT TT | 782/901 | 414 |
| R1066C | 17b | 228 | rare | Substitute C>T at 57 | AGGACTATGG ACACTT(C>T)GTG CCTTCGGACG GC | 782/901 | 414 |
| L1077P | 17b | 228 | rare | Substitute T>C at 91 | TTACTTTGAA ACTC(T>C)GTTCC ACAAAGCTC | 782/901 | 414 |
| Y1092X | 17b | 228 | 0.50% | Substitute C>A at 137 | CCAACTGGTT CTTGTA(C>A)CTG TCAACACTGC G | 782/901 | 414 |
| M1101K | 17b | 228 | Mut (65%) | Substitute T>A at 163 | TGCGCTGGTT CCAAA(T>A)GAGA ATAGAAATGA T | 782/901 | 414 |
| R1152X | 19 | 249 | 0.90% | Substitute C>T at 16 | ATGCGATCTG TGAGC(C>T)GAGT CTTTAAGTTC | 784/785 | 356 |
| 3659 del C | 19 | 249 | 0.80% | Delete C at 59 | AAGGTAAACC TACCAAGTCA ACCAAACCAT ACA | 784/785 | 356 |
| 3849 + 4A>G | 19 | 249 | 1.00% | Sub A>G 4 after last base | TCCTGGCCAG AGGGTG(A>G)GAT TGAACACT | 784/785 | 356 |
| 3849 10 kb | 19 | 10 kb | 1.40% | Sub C>T EcoR1 Fragment | ATAAAATGG(C>T)GAGTAAGACA | 792/791 | 450 |
| W1282R | 20 | 156 | rare | Substitute T>C at 127 | AATAACTTTG CAACAG(T>C)GGA GGAAAGCCTT T | 764/786 | 351 |
| W1282X | 20 | 156 | 2.10% | Substitute G>A at 129 | AATAACTTTG CAACAGTG(G>A)A GGAAAGCCTT T | 764/786 | 351 |
| 3905 ins T | 20 | 156 | 2.10% | Insert T at 58 | CTTTGTTATC AGCTTTTTTG AGAACTACTGA ACAC | 764/786 | 351 |
| 4005 + 1G>A | 20 | 156 | Manchester | Sub G>A after Exon 20 | AGTGATACCA CAG(G>A)TGAGCA AAAGGACTT | 764/786 | 351 |
| N1303K | 21 | 90 | 1.80% | Substitute C>G at 36 | CATTTAGAAA AAA(C>G)TTGGAT CCCTATGAAC | 756/793 | 396 |
| N1303H | 21 | 90 | rare | Substitute A>C at 34 | CATTTAGAAA A(A>C)ACTTGGAT CCCTATGAAC | | |

What is claimed is:

1. A method of comparing a target nucleic acid with a reference sequence comprising a predetermined sequence of nucleotides, the method comprising:
  (a) hybridizing a sample comprising the target nucleic acid to an array of oligonucleotide probes immobilized on a solid support, the array comprising:
    (1) a first probe set comprising a plurality of different probes, each probe exactly complementary to a subsequence of the reference sequence, the probe including a single interrogation position complementary to a corresponding nucleotide in the reference sequence, wherein the reference sequence is at least 50 bases, and the different probes of the first probe set are overlapping probes spanning the reference sequence;
    (2) a second probe set comprising a corresponding probe for each of the different probes in the first probe set, the corresponding probe in the second probe set being identical to the corresponding probe from the first probe set that includes the interrogation position, except that the one interrogation position is occupied by a different nucleotide in each of the two corresponding probes from the first and second probe sets;
  wherein the first probe set comprises at least three different interrogation positions corresponding to respective nucleotides in the reference sequence, the respective nucleotides forming at least three contiguous nucleotides in the reference sequence, and
  (b) detecting a hybridization pattern of the oligonucleotide probes to the target nucleic acid and determining from the hybridization pattern whether a nucleotide in the target sequence is the same or different from the corresponding nucleotide in the reference sequence.

2. The method of claim 1, wherein the determining comprises comparing the hybridization pattern to the target nucleic acid with a hybridization pattern of a nucleic acid having the reference sequence to the array of oligonucleotide probes.

3. The method of claim 1, wherein the determining step comprises:
  (1) comparing the relative specific binding of two corresponding probes from the first and second probe sets;
  (2) assigning a nucleotide in the target sequence as the complement of the interrogation position of the probe having the greater specific binding;
  (3) repeating (1) and (2) until each nucleotide of interest in the target sequence has been assigned.

4. The method of claim 1, wherein the probes are 6-30 nucleotides long.

5. A method of comparing a target nucleic acid with a reference sequence comprising a predetermined sequence of nucleotides, the method comprising:
  (a) hybridizing a sample comprising the target nucleic acid to an array of oligonucleotide probes immobilized on a solid support, the array comprising:
    (1) a first probe set comprising a plurality of different probes, each probe exactly complementary to a subsequence of the reference sequence, the probe including a single interrogation position complementary to a corresponding nucleotide in the reference sequence,
    (2) second, third and fourth probe sets, each comprising a corresponding probe for each of the different probes in the first probe set, the corresponding probes in the second, third and fourth probe sets being identical to the corresponding probe from the first probe set that includes the interrogation position, except that the interrogation position is occupied by a different nucleotide in each of the four corresponding probes from the first, second, third and fourth probe sets;
  wherein the first probe set comprises at least three different interrogation positions corresponding to respective nucleotides in the reference sequence, the respective nucleotides forming at least three contiguous nucleotides in the reference sequence, and
  (b) detecting a hybridization pattern of the oligonucleotide probes to the target nucleic acid and determining from the hybridization pattern whether a nucleotide in the target sequence is the same or different from the corresponding nucleotide in the reference sequence.

6. The method of claim 5, wherein the determining comprises comparing the hybridization pattern of the target nucleic acid with a hybridization pattern of a nucleic acid having the reference sequence to the oligonucleotide probes.

7. The method of claim 5, wherein the determining comprises:
  (1) comparing the relative specific binding of four corresponding probes from the first, second, third and fourth probe sets;
  (2) assigning a nucleotide in the target sequence as the complement of the interrogation position of the probe having the greatest specific binding;
  (3) repeating (1) and (2) until each nucleotide of interest in the target sequence has been assigned.

8. A method of comparing a target nucleic acid with a reference sequence comprising a predetermined sequence of nucleotides, the method comprising:
(a) hybridizing the target nucleic acid to an array of oligonucleotide probes immobilized on a solid support, the array comprising:
a perfectly matched probe exactly complementary to a subsequence of a reference sequence, the perfectly matched probe having a plurality of interrogation positions respectively corresponding to a plurality of nucleotides in the reference sequence,
for each interrogation position, three mismatched probes, each identical to the perfectly matched probe including the plurality of interrogation positions, except in the interrogation position, which is occupied by a different nucleotide in each of the three mismatched probes and the perfectly matched probe;
(b) for each interrogation position,
(1) comparing the relative specific binding of the three mismatched probes and the perfectly matched probe;
(2) assigning a nucleotide in the target sequence as the complement of the interrogation position of the probe having the greatest specific binding.

9. The method of claim 8, wherein the target sequence has an undetermined substitution relative to the reference sequence, and the method assigns a nucleotide to the substitution.

10. A method of comparing a target nucleic acid with a reference sequence comprising a predetermined sequence of nucleotides, the method comprising:
hybridizing the target sequence to an array of oligonucleotide probes immobilized on a solid support, the array comprising at least one pair of first and second probe groups, each group comprising a first and second sets of oligonucleotide probes,
the first probe set comprising a plurality of different probes, each probe exactly complementary to a subsequence of a reference sequence, and including a single interrogation position complementary to a corresponding nucleotide in the reference sequence, wherein the reference sequence is at least 50 bases, and the different probes of the first probe set are overlapping probes spanning the reference sequence;
the second probe set comprising a corresponding probe for each of the different probes in the first probe set, the corresponding probe in the second probe set being identical to the corresponding probe from the first probe set, except that the interrogation position is occupied by a different nucleotide in each of the two corresponding probes from the first and second probe sets;
the first probe set comprises at least three different interrogation positions corresponding to respective nucleotides in the reference sequence, the respective nucleotides forming at least three continguous nucleotides in the reference sequence;
wherein each of the different probes in the first probe set from the first group is exactly complementary to a subsequence of a first reference sequence and each of the different probes in the first probe set from the second group is exactly complementary to a subsequence from a second reference sequence;
determining which probes in the first group, relative to one another, hybridize to the target sequence, the relative specific binding of the probes indicating whether the target sequence is the same or different from the first reference sequence;
determining which probes in the second group, relative to one another, hybridize to the target sequence, the relative specific binding of the probes indicating whether the target sequence is the same or different from the second reference sequence.

11. The method of claim 10, wherein the hybridizing step comprising hybridizing the target sequence and a second target sequence to the array, and the relative specific binding of the probes from the first group indicates that the target is identical to the first reference sequence, and the relative specific binding of the probes from the second group indicates that the second target sequence is identical to the second reference sequence.

12. The method of claim 10, wherein the first and second target sequences are heterozygous alleles.

13. The method of claim 10, wherein the probes are 6-30 nucleotides long.

* * * * *

SEQUENCE LISTING (1) GENERAL INFORMATION:

(iii) NUMBER OF SEQUENCES: 250

(2) INFORMATION FOR SEQ ID NO: 1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (oligonucleotide)

(xi) SEQUENCE DESCRIPTION: SEQ ID NO: 1:

TAACCACTCA CGGGAGCA                                  18

(2) INFORMATION FOR SEQ ID NO: 2:

(i) SEQUENCE CHARACTERISTICS:

(A) LENGTH: 14 base pairs
          (B) TYPE: nucleic acid
          (C) STRANDEDNESS: single
          (D) TOPOLOGY: linear (ii) MOLECULE TYPE: DNA (oligonucleotide)

(xi) SEQUENCE DESCRIPTION: SEQ ID NO: 2:

ATTGGMGAGT GCCC                                                              14

(2) INFORMATION FOR SEQ ID NO: 3:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (ii) MOLECULE TYPE: DNA (oligonucleotide)

(xi) SEQUENCE DESCRIPTION: SEQ ID NO: 3:

ATTGGAGAGT GCCC                                                              14

(2) INFORMATION FOR SEQ ID NO: 4:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (ii) MOLECULE TYPE: DNA (oligonucleotide)

(xi) SEQUENCE DESCRIPTION: SEQ ID NO: 4:

ATTGGCGAGT GCCC                                                              14

(2) INFORMATION FOR SEQ ID NO: 5:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (ii) MOLECULE TYPE: DNA (oligonucleotide)

(xi) SEQUENCE DESCRIPTION: SEQ ID NO: 5:

ATTGGKGAGT GCCC                                                              14

(2) INFORMATION FOR SEQ ID NO: 6:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (ii) MOLECULE TYPE: DNA (oligonucleotide)

(xi) SEQUENCE DESCRIPTION: SEQ ID NO: 6:

ATTGGGGAGT GCCC                                                              14

(2) INFORMATION FOR SEQ ID NO: 7:

(i) SEQUENCE CHARACTERISTICS:
          (A) LENGTH: 14 base pairs
          (B) TYPE: nucleic acid
          (C) STRANDEDNESS: single
          (D) TOPOLOGY: linear -continued (ii) MOLECULE TYPE: DNA (oligonucleotide)

(xi) SEQUENCE DESCRIPTION: SEQ ID NO: 7:

ATTGGTGAGT GCCC                                                                14

(2) INFORMATION FOR SEQ ID NO: 8:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 8:

ATTGGRGAGT GCCC                                                                14

(2) INFORMATION FOR SEQ ID NO: 9:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 9:

TAACCCCTCA CGGGAGCA                                                            18

(2) INFORMATION FOR SEQ ID NO: 10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 10:

TAACCGCTCA CGGGAGCA                                                            18

(2) INFORMATION FOR SEQ ID NO: 11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 11:

TAACCTCTCA CGGGAGCA                                                            18

(2) INFORMATION FOR SEQ ID NO: 12:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 12:

ATTAACCACT CACGGGAGCT CT                                             22

(2) INFORMATION FOR SEQ ID NO: 13:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 13:

TGGTGNKYGC CCT                                                       13

(2) INFORMATION FOR SEQ ID NO: 14:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 14:

TGGTGAGCGC CCT                                                       13

(2) INFORMATION FOR SEQ ID NO: 15:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 15:

TGGTGCGCGC CCT                                                       13

(2) INFORMATION FOR SEQ ID NO: 16:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 16:

TGGTGGGCGC CCT                                                       13

(2) INFORMATION FOR SEQ ID NO: 17:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 17:

TGGTGTGCGC CCT                                                       13

```
(2) INFORMATION FOR SEQ ID NO: 18:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 18:

TGGTGATCGC CCT                                                         13

(2) INFORMATION FOR SEQ ID NO: 19:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 19:

TGGTGCTCGC CCT                                                         13

(2) INFORMATION FOR SEQ ID NO: 20:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 20:

TGGTGGTCGC CCT                                                         13

(2) INFORMATION FOR SEQ ID NO: 21:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 21:

TGGTGTTCGC CCT                                                         13

(2) INFORMATION FOR SEQ ID NO: 22:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 22:

TGGTGAGTGC CCT                                                         13

(2) INFORMATION FOR SEQ ID NO: 23:

(i) SEQUENCE CHARACTERISTICS:
        (A) LENGTH: 13 base pairs
```

```
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 23:

TGGTGCGTGC CCT                                                          13

(2) INFORMATION FOR SEQ ID NO: 24:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 24:

TGGTGCTCGC CCT                                                          13

(2) INFORMATION FOR SEQ ID NO: 25:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 25:

TGGTGTGTGC CCT                                                          13

(2) INFORMATION FOR SEQ ID NO: 26:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 26:

TGGTGATTGC CCT                                                          13

(2) INFORMATION FOR SEQ ID NO: 27:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 27:

TGGTGCTTGC CCT                                                          13

(2) INFORMATION FOR SEQ ID NO: 28:

(i) SEQUENCE CHARACTERISTICS:
        (A) LENGTH: 13 base pairs
        (B) TYPE: nucleic acid
        (C) STRANDEDNESS: single
        (D) TOPOLOGY: linear
```

```
    (ii) MOLECULE TYPE: DNA (oligonucleotide)

(xi) SEQUENCE DESCRIPTION: SEQ ID NO: 28:

TGGTGGTTGC CCT                                                            13

(2) INFORMATION FOR SEQ ID NO: 29:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 29:

TGGTGTTTGC CCT                                                            13

(2) INFORMATION FOR SEQ ID NO: 30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 30:

ATTAACCACT CCCGGGAGCT CT                                                  22

(2) INFORMATION FOR SEQ ID NO: 31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 31:

ATTAACCACT CGCGGGAGCT CT                                                  22

(2) INFORMATION FOR SEQ ID NO: 32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 32:

ATTAACCACT CTCGGGAGCT CT                                                  22

(2) INFORMATION FOR SEQ ID NO: 33:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 33:
```

TAATTNKYGA GTG                                                         13

(2) INFORMATION FOR SEQ ID NO: 34:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 34:

AATTGNKRAG TGC                                                         13

(2) INFORMATION FOR SEQ ID NO: 35:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 35:

ATTGGNKRGT GCC                                                         13

(2) INFORMATION FOR SEQ ID NO: 36:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 36:

TTGGTNMRTG CCC                                                         13

(2) INFORMATION FOR SEQ ID NO: 37:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 37:

GGTGANKRCC CTC                                                         13

(2) INFORMATION FOR SEQ ID NO: 38:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 38:

GTGAGNKYCC TCG                                                         13

(2) INFORMATION FOR SEQ ID NO: 39:

```
        (i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 39:

TGAGTNMYCT CGA                                                              13

(2) INFORMATION FOR SEQ ID NO: 40:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 40:

GAGTGNMYTC GAG                                                              13

(2) INFORMATION FOR SEQ ID NO: 41:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 41:

AGTGCNMYCG AGA                                                              13

(2) INFORMATION FOR SEQ ID NO: 42:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 42:

ATTNKYGAGT GCC                                                              13

(2) INFORMATION FOR SEQ ID NO: 43:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 43:

ATTGNKRAGT GCC                                                              13

(2) INFORMATION FOR SEQ ID NO: 44:

(i) SEQUENCE CHARACTERISTICS:
            (A) LENGTH: 13 base pairs
            (B) TYPE: nucleic acid
```

```
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 44:

ATTGGNKRGT GCC                                                      13

(2) INFORMATION FOR SEQ ID NO: 45:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 45:

ATTRGTNMGT GCC                                                      13

(2) INFORMATION FOR SEQ ID NO: 46:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 46:

ATTKRTGNGT GCC                                                      13

(2) INFORMATION FOR SEQ ID NO: 47:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 47:

TAAGCACTCA CGGGAGCA                                                 18

(2) INFORMATION FOR SEQ ID NO: 48:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 48:

TAATCACTCA CGGGAGCA                                                 18

(2) INFORMATION FOR SEQ ID NO: 49:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)
```

(xi) SEQUENCE DESCRIPTION: SEQ ID NO: 49:

TAAACACTCA CGGGAGCA                                                         18

(2) INFORMATION FOR SEQ ID NO: 50:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 50:

TAACGACTCA CGGGAGCA                                                         18

(2) INFORMATION FOR SEQ ID NO: 51:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 51:

TAACTACTCA CGGGAGCA                                                         18

(2) INFORMATION FOR SEQ ID NO: 52:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 52:

TAACAACTCA CGGGAGCA                                                         18

(2) INFORMATION FOR SEQ ID NO: 53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 53:

TAACCAGTCA CGGGAGCA                                                         18

(2) INFORMATION FOR SEQ ID NO: 54:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 54:

TAACCATTCA CGGGAGCA                                                         18

(2) INFORMATION FOR SEQ ID NO: 55:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 55:

TAACCAATCA CGGGAGCA                                             18

(2) INFORMATION FOR SEQ ID NO: 56:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 56:

TAACCACACA CGGGAGCA                                             18

(2) INFORMATION FOR SEQ ID NO: 57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 57:

TAACCACCCA CGGGAGCA                                             18

(2) INFORMATION FOR SEQ ID NO: 58:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 58:

TAACCACGCA CGGGAGCA                                             18

(2) INFORMATION FOR SEQ ID NO: 59:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 59:

CACGGGAGCA                                                      10

(2) INFORMATION FOR SEQ ID NO: 60:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 60:

ATTGNTNAGT GCCC                                                              14

(2) INFORMATION FOR SEQ ID NO: 61:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 61:

ATTGNANAGT GCCC                                                              14

(2) INFORMATION FOR SEQ ID NO: 62:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 62:

ATTGRYRHGT GCCC                                                              14

(2) INFORMATION FOR SEQ ID NO: 63:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 63:

ATTGKWKVGT GCCC                                                              14

(2) INFORMATION FOR SEQ ID NO: 64:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 64:

ATTGDHSMGT GCCC                                                              14

(2) INFORMATION FOR SEQ ID NO: 65:

(i) SEQUENCE CHARACTERISTICS:
            (A) LENGTH: 23 base pairs
            (B) TYPE: nucleic acid
            (C) STRANDEDNESS: single (D) TOPOLOGY: linear (ii) MOLECULE TYPE: DNA (oligonucleotide)

(xi) SEQUENCE DESCRIPTION: SEQ ID NO: 65:

TGGCTACGAG GAATCATCTG TTA                                              23

(2) INFORMATION FOR SEQ ID NO: 66:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 66:

GCTCCCCGAT                                                             10

(2) INFORMATION FOR SEQ ID NO: 67:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 67:

GCACCCCGAT                                                             10

(2) INFORMATION FOR SEQ ID NO: 68:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 68:

GCCCCCCGAT                                                             10

(2) INFORMATION FOR SEQ ID NO: 69:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 69:

GCGCCCCGAT                                                             10

(2) INFORMATION FOR SEQ ID NO: 70:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (oligonucleotide)

```
    (xi) SEQUENCE DESCRIPTION: SEQ ID NO: 70:

AGTACCAGAT CTCTAA                                                           16

(2) INFORMATION FOR SEQ ID NO: 71:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 71:

CATGGNCAGA GA                                                               12

(2) INFORMATION FOR SEQ ID NO: 72:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 72:

TCTCCTTGGA TATACTTGTG TGAATCAA                                              28

(2) INFORMATION FOR SEQ ID NO: 73:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 73:

TCACCAGATT TCGTAGTCTT TTCATA                                                26

(2) INFORMATION FOR SEQ ID NO: 74:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 74:

GTCTTGTGTT GAAATTCTCA GGGTAT                                                26

(2) INFORMATION FOR SEQ ID NO: 75:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 75:

CTTGTACCAG CTCACTACCT AAT                                                   23
```

(2) INFORMATION FOR SEQ ID NO: 76:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 76:

ACCTGAGAAG ATAGTAAGCT AGATGAA                                           27

(2) INFORMATION FOR SEQ ID NO: 77:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 77:

AACTCCGCCT TTCCAGTTGT AT                                               22

(2) INFORMATION FOR SEQ ID NO: 78:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 78:

TTAGTTTCTA GGGGTGGAAG ATACA                                             25

(2) INFORMATION FOR SEQ ID NO: 79:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 79:

TTAATGACAC TGAAGATCAC TGTTCTAT                                       28

(2) INFORMATION FOR SEQ ID NO: 80:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 80:

GCACATTTTT GCAAAGTTCA TTAGA                                             25

(2) INFORMATION FOR SEQ ID NO: 81:

(i) SEQUENCE CHARACTERISTICS:

(A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 81:

TCATGGGCCA TGTGCTTTTC AA                                              22

(2) INFORMATION FOR SEQ ID NO: 82:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 82:

ACCTTCCAGC ACTACAAACT AGAA                                            24

(2) INFORMATION FOR SEQ ID NO: 83:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 83:

CAAGTGAATC CTGAGCGTGA TTT                                             23

(2) INFORMATION FOR SEQ ID NO: 84:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 84:

GGTAGTGTGA AGGGTTCATA TGCATA                                          26

(2) INFORMATION FOR SEQ ID NO: 85:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 85:

GATTACATTA GAAGGAAGAT GTGCCTTT                                        28

(2) INFORMATION FOR SEQ ID NO: 86:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 86:

ACATGAATGA CATTTACAGC AAATGCTT                                              28

(2) INFORMATION FOR SEQ ID NO: 87:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 87:

GTGACCATAT TGTAATGCAT GTAGTGA                                               27

(2) INFORMATION FOR SEQ ID NO: 88:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 88:

ATGGTGAACA TATTTCTCAA GAGGTAA                                               27

(2) INFORMATION FOR SEQ ID NO: 89:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 89:

TGTCTCTGTA AACTGATGGC TAACA                                                 25

(2) INFORMATION FOR SEQ ID NO: 90:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 90:

TCGTATAGAG TTGATTGGAT TGAGAA                                                26

(2) INFORMATION FOR SEQ ID NO: 91:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 91:

```
CCATTAACTT AATGTGGTCT CATCACAA                                              28

(2) INFORMATION FOR SEQ ID NO: 92:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 92:

CTACCATAAT GCTTGGGAGA AATGAA                                                26

(2) INFORMATION FOR SEQ ID NO: 93:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 93:

TCAAAGAATG GCACCAGTGT GAAA                                                  24

(2) INFORMATION FOR SEQ ID NO: 94:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 94:

TGCTTAGCTA AAGTTAATGA GTTCAT                                                26

(2) INFORMATION FOR SEQ ID NO: 95:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 95:

AATTGTGAAA TTGTCTGCCA TTCTTAA                                               27

(2) INFORMATION FOR SEQ ID NO: 96:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 96:

GATTCACTTA CTGAACACAG TCTAACAA                                              28
```

(2) INFORMATION FOR SEQ ID NO: 97:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 97:

```
AGGCTTCTCA GTGATCTGTT G                                    21
```

(2) INFORMATION FOR SEQ ID NO: 98:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 98:

```
GAATCATTCA GTGGGTATAA GCA                                  23
```

(2) INFORMATION FOR SEQ ID NO: 99:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 99:

```
GCCATGGTAC CTATATGTCA CAGAA                                25
```

(2) INFORMATION FOR SEQ ID NO: 100:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 100:

```
TGCAGAGTAA TATGAATTTC TTGAGTACA                            29
```

(2) INFORMATION FOR SEQ ID NO: 101:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 101:

```
GGGACTCCAA ATATTGCTGT AGTAT                                25
```

(2) INFORMATION FOR SEQ ID NO: 102:

(i) SEQUENCE CHARACTERISTICS:
        (A) LENGTH: 23 base pairs (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 102:

GTACCTGTTG CTCCAGGTAT GTT                                              23

(2) INFORMATION FOR SEQ ID NO: 103:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 103:

TTTATANTAG AAACC                                                       15

(2) INFORMATION FOR SEQ ID NO: 104:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 104:

TTATAGNAGA AACCA                                                       15

(2) INFORMATION FOR SEQ ID NO: 105:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 105:

TATAGTNGAA ACCAC                                                       15

(2) INFORMATION FOR SEQ ID NO: 106:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 106:

ATAGTANAAA CCACA                                                       15

(2) INFORMATION FOR SEQ ID NO: 107:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 107:

TAGTAGNAAC CACAA                                                            15

(2) INFORMATION FOR SEQ ID NO: 108:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 108:

AGTAGANACC ACAAA                                                            15

(2) INFORMATION FOR SEQ ID NO: 109:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 109:

GTAGAANCCA CAAAG                                                            15

(2) INFORMATION FOR SEQ ID NO: 110:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 110:

TAGAAANCAC AAAGG                                                            15

(2) INFORMATION FOR SEQ ID NO: 111:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 111:

AGAAACNACA AAGAA                                                            15

(2) INFORMATION FOR SEQ ID NO: 112:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 112:

-continued

CATTAAAGAA AATATCATCT TTGGTGTTTC CTATGATGA                                     39

(2) INFORMATION FOR SEQ ID NO: 113:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 113:

CATTAAAGAA AATATCATTG GTGTTTCCTA TGATGA                                        36

(2) INFORMATION FOR SEQ ID NO: 114:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 114:

AACACCAATG ATGAT                                                              15

(2) INFORMATION FOR SEQ ID NO: 115:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 115:

CCTTCAGAGG GTAAAATTAA G                                                       21

(2) INFORMATION FOR SEQ ID NO: 116:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 116:

CCTTCAGAGT GTAAAATTAA G                                                       21

(2) INFORMATION FOR SEQ ID NO: 117:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 117:

TAATACGACT CACTATAGGG AGATGACCTA ATAATGATGG GTTT                               44

(2) INFORMATION FOR SEQ ID NO: 118:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO: 118:

TAATACGACT CACTATAGGG AGTAGTGTGA AGGGTTCATA TGC                          43

(2) INFORMATION FOR SEQ ID NO: 119:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO: 119:

CTCGGAATTA ACCCTCACTA AAGGTAGTGT GAAGGGTTCA TATGC                        45

(2) INFORMATION FOR SEQ ID NO: 120:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO: 120:

TAATACGACT CACTATAGGG AGAGCATACT AAAAGTGACT CTC                          43

(2) INFORMATION FOR SEQ ID NO: 121:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO: 121:

TAATACGACT CACTATAGGG AGACATGAAT GACATTTACA GCAA                         44

(2) INFORMATION FOR SEQ ID NO: 122:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO: 122:

CGGAATTAAC CCTCACTAAA GGACATGAAT GACATTTACA GCAA                         44

(2) INFORMATION FOR SEQ ID NO: 123:

(i) SEQUENCE CHARACTERISTICS:
            (A) LENGTH: 12 base pairs
            (B) TYPE: nucleic acid -continued

```
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 123:

TCGGATCGAC TT                                                      12

(2) INFORMATION FOR SEQ ID NO: 124:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 124:

CGGAATTAAC CCTCACTAAA GG                                           22

(2) INFORMATION FOR SEQ ID NO: 125:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 125:

AATTAACCCT CACTAAAGGG AG                                           22

(2) INFORMATION FOR SEQ ID NO: 126:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 126:

TAATACGACT CACTATAGGG AG                                           22

(2) INFORMATION FOR SEQ ID NO: 127:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 127:

ATTTAGGTGA CACTATAGAA                                              20

(2) INFORMATION FOR SEQ ID NO: 128:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (oligonucleotide)
```

(xi) SEQUENCE DESCRIPTION: SEQ ID NO: 128:

CTTTTTATTC TTTTGYAGAG AATGGGATAG A                    31

(2) INFORMATION FOR SEQ ID NO: 129:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 129:

TAATGCCCTT CGGCRATGTT TTTTCTGGA                       29

(2) INFORMATION FOR SEQ ID NO: 130:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 130:

ATTCTTTTGC AGAGATGGGA TAGAGAGCTG GCT                  33

(2) INFORMATION FOR SEQ ID NO: 131:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 131:

GAATGGGATA GAKAGCTGGC TTCAAAGA                        28

(2) INFORMATION FOR SEQ ID NO: 132:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 132:

CTATGGAATC TTTTYATATT TAGGGGTAAG                      30

(2) INFORMATION FOR SEQ ID NO: 133:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 133:

TTATGTTCTA TGRAATCTTT TTATATTTAG                      30

(2) INFORMATION FOR SEQ ID NO: 134:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 134:

```
AACAAGGAGG AACRCTCTAT CGCGATTTAT                                    30
```

(2) INFORMATION FOR SEQ ID NO: 135:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 135:

```
AACAAGGAGG AAYGCTCTAT CGCGATTTAT                                    30
```

(2) INFORMATION FOR SEQ ID NO: 136:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 136:

```
TATCGCGATT TAWCTAGGCA TAGGCTTATG                                    30
```

(2) INFORMATION FOR SEQ ID NO: 137:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 137:

```
GGCCTTCATC ACAYTGGAAT GCAGATGAGA                                    30
```

(2) INFORMATION FOR SEQ ID NO: 138:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 138:

```
GATTTATAAG AAGKTAATAC TTCCTTGCAC                                    30
```

(2) INFORMATION FOR SEQ ID NO: 139:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 139:

CAAATTTGAT GAAKTATGTA CCTATTGATT                                              30

(2) INFORMATION FOR SEQ ID NO: 140:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 140:

TGGATCGCTC CTTKGCAAGT GGCACTCCTC                                              30

(2) INFORMATION FOR SEQ ID NO: 141:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 141:

AATCATCCTC CGGAAAGATA TTCACCACCA TCT                                          33

(2) INFORMATION FOR SEQ ID NO: 142:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 142:

TATTCACCAC CATCTCTCAT TCTGCATTGT T                                            31

(2) INFORMATION FOR SEQ ID NO: 143:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 143:

CCACCATCTC ATTCTGATTG TTCTGCGCAT GG                                           32

(2) INFORMATION FOR SEQ ID NO: 144:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: DNA (oligonucleotide)

(xi) SEQUENCE DESCRIPTION: SEQ ID NO: 144:

AAGGAATCAT CCTCYGGAAA ATATTCATTA                                        30

(2) INFORMATION FOR SEQ ID NO: 145:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 145:

CTGCATTGTT CTGCRCATGG CGGTCACTCG                                        30

(2) INFORMATION FOR SEQ ID NO: 146:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 146:

CTGCATTGTT CTGCKCATGG CGGTCACTCG                                        30

(2) INFORMATION FOR SEQ ID NO: 147:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 147:

CTGCATTGTT CTGCSCATGG CGGTCACTCG                                        30

(2) INFORMATION FOR SEQ ID NO: 148:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 148:

CTTCTTCTCA GGGTTCTTGT GGTGTTTTTA TC                                     32

(2) INFORMATION FOR SEQ ID NO: 149:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

```
     (xi) SEQUENCE DESCRIPTION: SEQ ID NO: 149:

AAACAAAATA CAGRTAATGT ACCATAATG                                29

(2) INFORMATION FOR SEQ ID NO: 150:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 150:

AGGACAGTTG TTGGMGGTTG CTGGATCCA                                29

(2) INFORMATION FOR SEQ ID NO: 151:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 151:

GGAGCCTTCA GAGKGTAAAA TTAAGCACA                                29

(2) INFORMATION FOR SEQ ID NO: 152:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 152:

TCATTCTGTT CTYAGTTTTC CTGGATTAT                                29

(2) INFORMATION FOR SEQ ID NO: 153:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 153:

ATTAAAGAAA ATATCTTTGG TGTTTCCTAT G                             31

(2) INFORMATION FOR SEQ ID NO: 154:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 154:

TAAAGAAAAT ATCATCTKTG GTGTTTCCTA                               30
```

(2) INFORMATION FOR SEQ ID NO: 155:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 155:

ATTAAAGAAA ATATCATTGG TGTTTCCTAT G                                  31

(2) INFORMATION FOR SEQ ID NO: 156:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 156:

TAGATACAGA AGCKTCATCA AAGCATGCC                                     29

(2) INFORMATION FOR SEQ ID NO: 157:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 157:

TATTTTTGGT AATARGACAT CTCCAAGTTT                                    30

(2) INFORMATION FOR SEQ ID NO: 158:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 158:

ACAATATAGT TCTTKGAGAA GGTGGAAT                                      28

(2) INFORMATION FOR SEQ ID NO: 159:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 159:

AGGTGGAATC ACACTGARTG GAGGTCAACG                                    30

(2) INFORMATION FOR SEQ ID NO: 160:

(i) SEQUENCE CHARACTERISTICS:

(A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 160:

AGGTGGAATC ACACTGAKTG GAGGTCAACG                                              30

(2) INFORMATION FOR SEQ ID NO: 161:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 161:

AGGTGGAATC ACACTGMGTG GAGGTCAACG                                              30

(2) INFORMATION FOR SEQ ID NO: 162:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 162:

AGGTGGAATC ACACTGAGKG GAGGTCAACG                                              30

(2) INFORMATION FOR SEQ ID NO: 163:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 163:

ATCACACTGA GTGGAGRTCA ACGAGCAAGA                                              30

(2) INFORMATION FOR SEQ ID NO: 164:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 164:

ATCACACTGA GTGGARGTCA ACGAGCAAGA                                              30

(2) INFORMATION FOR SEQ ID NO: 165:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 165:

ACACTGAGTG GAGGTYAACG AGCAAGAATT                                    30

(2) INFORMATION FOR SEQ ID NO: 166:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 166:

TGAGTGGAGG TCAACRAGCA AGAATTTCT                                     29

(2) INFORMATION FOR SEQ ID NO: 167:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 167:

TGAGTGGAGG TCAAYGAGCA AGAATTTCTT T                                  31

(2) INFORMATION FOR SEQ ID NO: 168:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 168:

GCAAGAATTT CTTTARCAAG GTGAATAAC                                     29

(2) INFORMATION FOR SEQ ID NO: 169:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 169:

AATTTCTTTA GCAASGTGAA TAACTAA                                       27

(2) INFORMATION FOR SEQ ID NO: 170:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 170:

GAATTTCTTT AGCAARGTGA ATAACTAA                                          28

(2) INFORMATION FOR SEQ ID NO: 171:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 171:

GAAATATTTG AAAGRTATGT TCTTTGAAT                                         29

(2) INFORMATION FOR SEQ ID NO: 172:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 172:

AACTCATGGG ATGTGWTTCT TTCGACCAAT                                        30

(2) INFORMATION FOR SEQ ID NO: 173:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 173:

GACAGAAACA AAAACAATC TTTTAAACAG AC                                      32

(2) INFORMATION FOR SEQ ID NO: 174:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 174:

GACAGAAACA AAAAAACAA TCTTTTAAAC AGAC                                    34

(2) INFORMATION FOR SEQ ID NO: 175:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 175:

CTCCTTGGAA AGTGARTATT CCATGTCCTA                                        30

(2) INFORMATION FOR SEQ ID NO: 176:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 176:

TTTATGTTAT TGCARTGTT TTCTATGGAA A        31

(2) INFORMATION FOR SEQ ID NO: 177:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 177:

ATTTGTGATA TGATTAYTCT AATTTAGTCT TT        32

(2) INFORMATION FOR SEQ ID NO: 178:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 178:

AGGACTATGG ACACTTYGTG CCTTCGGACG GC        32

(2) INFORMATION FOR SEQ ID NO: 179:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 179:

TTACTTTGAA ACTCYGTTCC ACAAAGCTC        29

(2) INFORMATION FOR SEQ ID NO: 180:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 180:

CCAACTGGTT CTTGTAMCTG TCAACACTGC G        31

(2) INFORMATION FOR SEQ ID NO: 181:

(i) SEQUENCE CHARACTERISTICS:
        (A) LENGTH: 31 base pairs

-continued (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 181:

TGCGCTGGTT CCAAAWGAGA ATAGAAATGA T                              31

(2) INFORMATION FOR SEQ ID NO: 182:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 182:

ATGCGATCTG TGAGCYGAGT CTTTAAGTTC                                30

(2) INFORMATION FOR SEQ ID NO: 183:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 183:

AAGGTAAACC TACAAGTCAA CCAAACCATA CA                             32

(2) INFORMATION FOR SEQ ID NO: 184:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 184:

TCCTGGCCAG AGGGTGRGAT TTGAACACT                                 29

(2) INFORMATION FOR SEQ ID NO: 185:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 185:

ATAAAATGGY GAGTAAGACA                                           20

(2) INFORMATION FOR SEQ ID NO: 186:

(i) SEQUENCE CHARACTERISTICS:
        (A) LENGTH: 31 base pairs
        (B) TYPE: nucleic acid
        (C) STRANDEDNESS: single
        (D) TOPOLOGY: linear

```
        (ii) MOLECULE TYPE: DNA (oligonucleotide)

(xi) SEQUENCE DESCRIPTION: SEQ ID NO: 186:

AATAACTTTG CAACAGYGGA GGAAAGCCTT T                                   31

(2) INFORMATION FOR SEQ ID NO: 187:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 187:

AATAACTTTG CAACAGTGRA GGAAAGCCTT T                                   31

(2) INFORMATION FOR SEQ ID NO: 188:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 188:

CTTTGTTATC AGCTTTTTTG AGACTACTGA ACAC                                34

(2) INFORMATION FOR SEQ ID NO: 189:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 189:

AGTGATACCA CAGRTGAGCA AAAGGACTT                                      29

(2) INFORMATION FOR SEQ ID NO: 190:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 190:

CATTTAGAAA AAASTTGGAT CCCTATGAAC                                     30

(2) INFORMATION FOR SEQ ID NO: 191:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 191:
```

-continued

```
CATTTAGAAA AMACTTGGAT CCCTATGAAC                                    30

(2) INFORMATION FOR SEQ ID NO: 192:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 192:

ACTGTTAGCT AATTGG                                                   16

(2) INFORMATION FOR SEQ ID NO: 193:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 193:

GGGCAATCGA GGGGGG                                                   16

(2) INFORMATION FOR SEQ ID NO: 194:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 194:

AAAGAAAAAA GACAGTACTA AATGGA                                        26

(2) INFORMATION FOR SEQ ID NO: 195:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 195:

TACTGTATTT TTT                                                      13

(2) INFORMATION FOR SEQ ID NO: 196:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 196:

TACTGTCTTT TTT                                                      13

(2) INFORMATION FOR SEQ ID NO: 197:
```

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 197:

TACTGTGTTT TTT                                                              13

(2) INFORMATION FOR SEQ ID NO: 198:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 198:

TACTGTTTTT TTT                                                              13

(2) INFORMATION FOR SEQ ID NO: 199:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 199:

GTACTGACTT TTT                                                              13

(2) INFORMATION FOR SEQ ID NO: 200:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 200:

GTACTGCCTT TTT                                                              13

(2) INFORMATION FOR SEQ ID NO: 201:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 201:

GTACTGGCTT TTT                                                              13

(2) INFORMATION FOR SEQ ID NO: 202:

(i) SEQUENCE CHARACTERISTICS:
        (A) LENGTH: 13 base pairs
        (B) TYPE: nucleic acid (C) STRANDEDNESS: single
        (D) TOPOLOGY: linear (ii) MOLECULE TYPE: DNA (probe)

(xi) SEQUENCE DESCRIPTION: SEQ ID NO: 202:

GTACTGTCTT TTT                                                          13

(2) INFORMATION FOR SEQ ID NO: 203:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 203:

AGTACTATCT TTT                                                          13

(2) INFORMATION FOR SEQ ID NO: 204:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 204:

AGTACTCTCT TTT                                                          13

(2) INFORMATION FOR SEQ ID NO: 205:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 205:

AGTACTGTCT TTT                                                          13

(2) INFORMATION FOR SEQ ID NO: 206:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 206:

AGTACTTTCT TTT                                                          13

(2) INFORMATION FOR SEQ ID NO: 207:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 207:

GGGNCCCTTA A                                                11

(2) INFORMATION FOR SEQ ID NO: 208:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 208:

TAAAGTAAGA CATAAC                                           16

(2) INFORMATION FOR SEQ ID NO: 209:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 209:

GGCTGACGTC AGCAAT                                           16

(2) INFORMATION FOR SEQ ID NO: 210:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 210:

TTGCTGACAT CAGCC                                            15

(2) INFORMATION FOR SEQ ID NO: 211:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 211:

TTGCTGACCT CAGCC                                            15

(2) INFORMATION FOR SEQ ID NO: 212:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 212:

TTGCTGACGT CAGCC                                            15

(2) INFORMATION FOR SEQ ID NO: 213:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 213:

TTGCTGACTT CAGCC                                                          15

(2) INFORMATION FOR SEQ ID NO: 214:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 214:

ATTCCCGGGA TC                                                              12

(2) INFORMATION FOR SEQ ID NO: 215:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 215:

AGGTCAACGA GCAA                                                         14

(2) INFORMATION FOR SEQ ID NO: 216:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 216:

AGGTCAATGA GCAA                                                         14

(2) INFORMATION FOR SEQ ID NO: 217:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 217:

GTAATTTCTT TTATAGTAGA AACCACAAAG GATAC                     35

(2) INFORMATION FOR SEQ ID NO: 218:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: DNA (oligonucleotide)

(xi) SEQUENCE DESCRIPTION: SEQ ID NO: 218:

CATTAAAGAA AATATCATCT TTGGTGTTTC CTATG     35

(2) INFORMATION FOR SEQ ID NO: 219:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 219:

CATTAAAGAA AATATCATTG GTGTTTCCTA TG     32

(2) INFORMATION FOR SEQ ID NO: 220:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 220:

CATTAAAGAA AATATCAT     18

(2) INFORMATION FOR SEQ ID NO: 221:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 221:

TATTAAAGAA AATATCATCT TTGGTGTTTC CTATC     35

(2) INFORMATION FOR SEQ ID NO: 222:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 222:

CCTTAAAGAA AATATCATCT TTGGTGTTTC CTAAA     35

(2) INFORMATION FOR SEQ ID NO: 223:

(i) SEQUENCE CHARACTERISTICS:
        (A) LENGTH: 35 base pairs
        (B) TYPE: nucleic acid
        (C) STRANDEDNESS: single

```
        (D) TOPOLOGY: linear (ii) MOLECULE TYPE: DNA (oligonucletide)

(xi) SEQUENCE DESCRIPTION: SEQ ID NO: 223:

CTTTAAAGAA AATAAAAAAA TTGGTGTTTC CTAAA                                35

(2) INFORMATION FOR SEQ ID NO: 224:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 224:

GGAAGTCTCC CATTTTAATT                                                 20

(2) INFORMATION FOR SEQ ID NO: 225:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 225:

CCTTCAGAGG GTAAAATTAA                                                 20

(2) INFORMATION FOR SEQ ID NO: 226:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 226:

CCTTCAGAGK GTAAAATTAA                                                 20

(2) INFORMATION FOR SEQ ID NO: 227:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 227:

CCTTCAGAGT GTAAAATTAA                                                 20

(2) INFORMATION FOR SEQ ID NO: 228:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (probe)
```

(xi) SEQUENCE DESCRIPTION: SEQ ID NO: 228:

CCTTCAGAGG GTAAAATCA                                                    19

(2) INFORMATION FOR SEQ ID NO: 229:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 229:

GATTCAGAGT GTAAAATAC                                                    19

(2) INFORMATION FOR SEQ ID NO: 230:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 230:

AAAAAGAGT GTAAAATGA                                                     19

(2) INFORMATION FOR SEQ ID NO: 231:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 231:

GTAATTTCTT TTATAGTAGA AACCACAAAG GATAC                                  35

(2) INFORMATION FOR SEQ ID NO: 232:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 232:

CATTAAAGAA AATAACATCA TTGGTGTTTC CTATG                                  35

(2) INFORMATION FOR SEQ ID NO: 233:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 233:

TGAGTGGAGG TCAACGAGCA AGA                                               23

(2) INFORMATION FOR SEQ ID NO: 234:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 234:

TGAGTGGAGG TCAATGAGCA AGA                                   23

(2) INFORMATION FOR SEQ ID NO: 235:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 235:

GTGGAGGTCA ACGA                                              14

(2) INFORMATION FOR SEQ ID NO: 236:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 236:

GTGGAGATCA ACGT                                              14

(2) INFORMATION FOR SEQ ID NO: 237:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 237:

TCAGAGGGTA AAAT                                              14

(2) INFORMATION FOR SEQ ID NO: 238:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 238:

TCAGAGTGTA AAAT                                              14

(2) INFORMATION FOR SEQ ID NO: 239:

(i) SEQUENCE CHARACTERISTICS:

(A) LENGTH: 19 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 239:

AAATATCATC TTTGGTGTT                                            19

(2) INFORMATION FOR SEQ ID NO: 240:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 240:

AAATATCATC TGTGGTGTT                                            19

(2) INFORMATION FOR SEQ ID NO: 241:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 241:

TAGTTCTTGG AGAAGGT                                              17

(2) INFORMATION FOR SEQ ID NO: 242:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 242:

TAGTTCTTTG AGAAGGT                                              17

(2) INFORMATION FOR SEQ ID NO: 243:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 243:

GAGTGGAGGT CAACGAG                                              17

(2) INFORMATION FOR SEQ ID NO: 244:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 244:

GAGTGGAGAT CAACGAG                                                                    17

(2) INFORMATION FOR SEQ ID NO: 245:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 245:

AGCCTAGCTG AA                                                                         12

(2) INFORMATION FOR SEQ ID NO: 246:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 246:

GGACATCTCC AAGTTTGCAG AGAAAGACAA TATAG                                                35

(2) INFORMATION FOR SEQ ID NO: 247:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 247:

TTCTTGGAGA AGGTGGAATC ACACTGAGTG GAGGTC                                               36

(2) INFORMATION FOR SEQ ID NO: 248:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 248:

AACGAGCAAG AATTTCTTTA GCAAGGTGAA TAACTA                                               36

(2) INFORMATION FOR SEQ ID NO: 249:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 249:

-continued

```
GGTCAACGAG CAAG                                                    14

(2) INFORMATION FOR SEQ ID NO: 250:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 250:

GGTCAATGAG CAAG                                                    14
```